US010716515B2

(12) United States Patent
Gustafsson et al.

(10) Patent No.: US 10,716,515 B2
(45) Date of Patent: Jul. 21, 2020

(54) SYSTEMS, DEVICES, AND METHODS FOR TRACKING AND COMPENSATING FOR PATIENT MOTION DURING A MEDICAL IMAGING SCAN

(71) Applicant: Kineticor, Inc., Honolulu, HI (US)

(72) Inventors: Ulf Peter Gustafsson, San Diego, CA (US); Andreas Wilhelm Dreher, Escondido, CA (US)

(73) Assignee: Kineticor, Inc., Honolulu, HI (US)

( * ) Notice: Subject to any disclaimer, the term of this patent is extended or adjusted under 35 U.S.C. 154(b) by 907 days.

(21) Appl. No.: 15/356,323

(22) Filed: Nov. 18, 2016

(65) Prior Publication Data

US 2017/0143271 A1    May 25, 2017

Related U.S. Application Data

(60) Provisional application No. 62/333,023, filed on May 6, 2016, provisional application No. 62/332,402, filed (Continued)

(51) Int. Cl.
*A61B 5/05* (2006.01)
*A61B 5/00* (2006.01)
(Continued)

(52) U.S. Cl.
CPC .............. *A61B 5/721* (2013.01); *A61B 5/055* (2013.01); *A61B 5/0555* (2013.01);
(Continued)

(58) Field of Classification Search
CPC . G06T 5/003; G06T 5/50; G06T 2207/30016; G06T 2207/10081;
(Continued)

(56) References Cited

U.S. PATENT DOCUMENTS 3,811,213 A   5/1974  Eaves
4,689,999 A   9/1987  Shkedi
(Continued)

FOREIGN PATENT DOCUMENTS

CN   100563551   12/2009
CN   105392423    3/2016
(Continued)

OTHER PUBLICATIONS

Armstrong et al., RGR-6D: Low-cost, high-accuracy measurement of 6-DOF Pose from a Single Image. Publication date unknown.
(Continued)

*Primary Examiner* — Elmer M Chao
(74) *Attorney, Agent, or Firm* — Knobbe, Martens, Olson & Bear, LLP

(57) ABSTRACT

In some embodiments, a motion detection and correction system and/or device for tracking and compensating for patient motion during a medical imaging scan can be adapted to be integrated into a medical imaging scanner, such as an MRI scanner, or be adapted to retrofit a pre-existing medical imaging scanner. In certain embodiments, the motion detection system and/or device can comprise one or more mounting brackets and a motion correction device housing, which can further comprise one or more detector modules and a power unit. In further embodiments, the collected motion data can be further analyzed by an image processing unit of the motion tracking and/or correction system.

15 Claims, 22 Drawing Sheets

Related U.S. Application Data on May 5, 2016, provisional application No. 62/258,915, filed on Nov. 23, 2015.

(51) Int. Cl.

| | | |
|---|---|---|
| *A61B 5/11* | (2006.01) | |
| *A61B 5/055* | (2006.01) | |
| *A61N 5/10* | (2006.01) | |
| *G01R 33/565* | (2006.01) | |
| *G01R 33/28* | (2006.01) | |
| *A61B 5/042* | (2006.01) | |

(52) U.S. Cl.
CPC ........... *A61B 5/1114* (2013.01); *A61B 5/1127* (2013.01); *A61N 5/1049* (2013.01); *A61N 5/1067* (2013.01); *G01R 33/283* (2013.01); *G01R 33/56509* (2013.01); *A61B 5/042* (2013.01); *A61B 2560/0406* (2013.01); *A61B 2560/0443* (2013.01); *A61B 2562/182* (2013.01); *A61N 2005/1059* (2013.01)

(58) Field of Classification Search
CPC ........... G06T 2207/10088; G06T 7/292; A61B 6/5205; A61B 6/032; A61B 6/527; A61B 6/463; A61B 5/055; A61B 5/0013; A61B 5/721; A61B 5/003; A61B 5/50; A61B 2560/0475; A61B 2576/00
See application file for complete search history.

(56) References Cited

U.S. PATENT DOCUMENTS

| | | |
|---|---|---|
| 4,724,386 A | 2/1988 | Haacke et al. |
| 4,894,129 A | 1/1990 | Leiponen et al. |
| 4,923,295 A | 5/1990 | Sireul et al. |
| 4,953,554 A | 9/1990 | Zerhouni et al. |
| 4,988,886 A | 1/1991 | Palum et al. |
| 5,075,562 A | 12/1991 | Greivenkamp et al. |
| 5,318,026 A | 6/1994 | Pelc |
| 5,515,711 A | 5/1996 | Hinkle |
| 5,545,993 A | 8/1996 | Taguchi et al. |
| 5,615,677 A | 4/1997 | Pelc et al. |
| 5,687,725 A | 11/1997 | Wendt |
| 5,728,935 A | 3/1998 | Czompo |
| 5,802,202 A | 9/1998 | Yamada et al. |
| 5,808,376 A | 9/1998 | Gordon et al. |
| 5,835,223 A | 11/1998 | Zawemer et al. |
| 5,877,732 A | 3/1999 | Ziarati |
| 5,886,257 A | 3/1999 | Gustafson et al. |
| 5,889,505 A | 3/1999 | Toyama |
| 5,891,060 A | 4/1999 | McGregor |
| 5,936,722 A | 8/1999 | Armstrong et al. |
| 5,936,723 A | 8/1999 | Schmidt et al. |
| 5,947,900 A | 9/1999 | Derbyshire et al. |
| 5,987,349 A | 11/1999 | Schulz |
| 6,016,439 A | 1/2000 | Acker |
| 6,031,888 A | 2/2000 | Ivan et al. |
| 6,044,308 A | 3/2000 | Huissoon |
| 6,057,680 A | 5/2000 | Foo et al. |
| 6,061,644 A | 5/2000 | Leis |
| 6,088,482 A | 7/2000 | He |
| 6,144,875 A | 11/2000 | Schweikard et al. |
| 6,175,756 B1 | 1/2001 | Ferre |
| 6,236,737 B1 | 5/2001 | Gregson et al. |
| 6,246,900 B1 | 6/2001 | Cosman et al. |
| 6,279,579 B1 | 8/2001 | Riaziat et al. |
| 6,285,902 B1 | 9/2001 | Kienzle, III et al. |
| 6,289,235 B1 | 9/2001 | Webber |
| 6,292,683 B1 | 9/2001 | Gupta et al. |
| 6,298,262 B1 | 10/2001 | Franck et al. |
| 6,381,485 B1 | 4/2002 | Hunter et al. |
| 6,384,908 B1 | 5/2002 | Schmidt et al. |
| 6,390,982 B1 | 5/2002 | Bova et al. |
| 6,402,762 B2 | 6/2002 | Hunter et al. |
| 6,405,072 B1 | 6/2002 | Cosman |
| 6,421,551 B1 | 7/2002 | Kuth et al. |
| 6,467,905 B1 | 10/2002 | Stahl et al. |
| 6,474,159 B1 | 11/2002 | Foxlin et al. |
| 6,484,131 B1 | 11/2002 | Amoral-Moriya et al. |
| 6,490,475 B1 | 12/2002 | Seeley et al. |
| 6,501,981 B1 | 12/2002 | Schweikard et al. |
| 6,587,707 B2 | 7/2003 | Nehrke et al. |
| 6,621,889 B1 | 9/2003 | Mostafavi |
| 6,650,920 B2 | 11/2003 | Schaldach et al. |
| 6,662,036 B2 | 12/2003 | Cosman |
| 6,687,528 B2 | 2/2004 | Gupta et al. |
| 6,690,965 B1 | 2/2004 | Riaziat et al. |
| 6,711,431 B2 | 3/2004 | Sarin et al. |
| 6,731,970 B2 | 5/2004 | Schlossbauer et al. |
| 6,758,218 B2 | 7/2004 | Anthony |
| 6,771,997 B2 | 8/2004 | Schaffer |
| 6,794,869 B2 | 9/2004 | Brittain |
| 6,856,827 B2 | 2/2005 | Seeley et al. |
| 6,856,828 B2 | 2/2005 | Cossette et al. |
| 6,876,198 B2 | 4/2005 | Watanabe et al. |
| 6,888,924 B2 | 5/2005 | Claus et al. |
| 6,891,374 B2 | 5/2005 | Brittain |
| 6,892,089 B1 | 5/2005 | Prince et al. |
| 6,897,655 B2 | 5/2005 | Brittain et al. |
| 6,913,603 B2 | 7/2005 | Knopp et al. |
| 6,937,696 B1 | 8/2005 | Mostafavi |
| 6,959,266 B1 | 10/2005 | Mostafavi |
| 6,973,202 B2 | 12/2005 | Mostafavi |
| 6,980,679 B2 | 12/2005 | Jeung et al. |
| 7,007,699 B2 | 3/2006 | Martinelli et al. |
| 7,107,091 B2 | 9/2006 | Jutras et al. |
| 7,110,805 B2 | 9/2006 | Machida |
| 7,123,758 B2 | 10/2006 | Jeung et al. |
| 7,171,257 B2 | 1/2007 | Thomson |
| 7,173,426 B1 | 2/2007 | Bulumulla et al. |
| 7,176,440 B2 | 2/2007 | Cofer et al. |
| 7,191,100 B2 | 3/2007 | Mostafavi |
| 7,204,254 B2 | 4/2007 | Riaziat et al. |
| 7,209,777 B2 | 4/2007 | Saranathan et al. |
| 7,209,977 B2 | 4/2007 | Acharya et al. |
| 7,260,253 B2 | 8/2007 | Rahn et al. |
| 7,260,426 B2 | 8/2007 | Schweikard et al. |
| 7,295,007 B2 | 11/2007 | Dold |
| 7,313,430 B2 | 12/2007 | Urquhart et al. |
| 7,327,865 B2 | 2/2008 | Fu et al. |
| 7,348,776 B1 | 3/2008 | Aksoy et al. |
| 7,403,638 B2 | 7/2008 | Jeung et al. |
| 7,494,277 B2 | 2/2009 | Setala |
| 7,498,811 B2 | 3/2009 | Macfarlane et al. |
| 7,502,413 B2 | 3/2009 | Guillaume |
| 7,505,805 B2 | 3/2009 | Kuroda |
| 7,535,411 B2 | 5/2009 | Falco |
| 7,551,089 B2 | 6/2009 | Sawyer |
| 7,561,909 B1 | 7/2009 | Pai et al. |
| 7,567,697 B2 | 7/2009 | Mostafavi |
| 7,573,269 B2 | 8/2009 | Yao |
| 7,602,301 B1 | 10/2009 | Stirling et al. |
| 7,603,155 B2 | 10/2009 | Jensen |
| 7,623,623 B2 | 11/2009 | Raanes et al. |
| 7,657,300 B2 | 2/2010 | Hunter et al. |
| 7,657,301 B2 | 2/2010 | Mate et al. |
| 7,659,521 B2 | 2/2010 | Pedroni |
| 7,660,623 B2 | 2/2010 | Hunter et al. |
| 7,668,288 B2 | 2/2010 | Conwell et al. |
| 7,689,263 B1 | 3/2010 | Fung et al. |
| 7,702,380 B1 | 4/2010 | Dean |
| 7,715,604 B2 | 5/2010 | Sun et al. |
| 7,742,077 B2 | 6/2010 | Sablak et al. |
| 7,742,621 B2 | 6/2010 | Hammoud et al. |
| 7,742,804 B2 | 6/2010 | Faul et al. |
| 7,744,528 B2 | 6/2010 | Wallace et al. |
| 7,760,908 B2 | 7/2010 | Curtner et al. |
| 7,766,837 B2 | 8/2010 | Pedrizzetti et al. |
| 7,769,430 B2 | 8/2010 | Mostafavi |
| 7,772,569 B2 | 8/2010 | Bewersdorf et al. |
| 7,787,011 B2 | 8/2010 | Zhou et al. |
| 7,787,935 B2 | 8/2010 | Dumoulin et al. |
| 7,791,808 B2 | 9/2010 | French et al. |

(56) References Cited

U.S. PATENT DOCUMENTS

| | | | |
|---|---|---|---|
| 7,792,249 | B2 | 9/2010 | Gertner et al. |
| 7,796,154 | B2 | 9/2010 | Senior et al. |
| 7,798,730 | B2 | 9/2010 | Westerweck |
| 7,801,330 | B2 | 9/2010 | Zhang et al. |
| 7,805,987 | B1 | 10/2010 | Smith |
| 7,806,604 | B2 | 10/2010 | Bazakos et al. |
| 7,817,046 | B2 | 10/2010 | Coveley et al. |
| 7,817,824 | B2 | 10/2010 | Liang et al. |
| 7,819,818 | B2 | 10/2010 | Ghajar |
| 7,833,221 | B2 | 11/2010 | Voegele |
| 7,834,846 | B1 | 11/2010 | Bell |
| 7,835,783 | B1 | 11/2010 | Aletras |
| 7,839,551 | B2 | 11/2010 | Lee et al. |
| 7,840,253 | B2 | 11/2010 | Tremblay et al. |
| 7,844,094 | B2 | 11/2010 | Jeung et al. |
| 7,844,320 | B2 | 11/2010 | Shahidi |
| 7,850,526 | B2 | 12/2010 | Zalewski et al. |
| 7,860,301 | B2 | 12/2010 | Se et al. |
| 7,866,818 | B2 | 1/2011 | Schroeder et al. |
| 7,868,282 | B2 | 1/2011 | Lee et al. |
| 7,878,652 | B2 | 2/2011 | Chen et al. |
| 7,883,415 | B2 | 2/2011 | Larsen et al. |
| 7,889,907 | B2 | 2/2011 | Engelbart et al. |
| 7,894,877 | B2 | 2/2011 | Lewin et al. |
| 7,902,825 | B2 | 3/2011 | Bammer et al. |
| 7,907,987 | B2 | 3/2011 | Dempsey |
| 7,908,060 | B2 | 3/2011 | Basson et al. |
| 7,908,233 | B2 | 3/2011 | Angell et al. |
| 7,911,207 | B2 | 3/2011 | Macfarlane et al. |
| 7,912,532 | B2 | 3/2011 | Schmidt et al. |
| 7,920,250 | B2 | 4/2011 | Robert et al. |
| 7,920,911 | B2 | 4/2011 | Hoshino et al. |
| 7,925,066 | B2 | 4/2011 | Ruohonen et al. |
| 7,925,549 | B2 | 4/2011 | Looney et al. |
| 7,931,370 | B2 | 4/2011 | Prat Bartomeu |
| 7,944,354 | B2 | 5/2011 | Kangas et al. |
| 7,944,454 | B2 | 5/2011 | Zhou et al. |
| 7,945,304 | B2 | 5/2011 | Feinberg |
| 7,946,921 | B2 | 5/2011 | Ofek et al. |
| 7,962,197 | B2 | 6/2011 | Rioux et al. |
| 7,971,999 | B2 | 7/2011 | Zinser |
| 7,977,942 | B2 | 7/2011 | White |
| 7,978,925 | B1 | 7/2011 | Souchard |
| 7,988,288 | B2 | 8/2011 | Donaldson |
| 7,990,365 | B2 | 8/2011 | Marvit et al. |
| 8,005,571 | B2 | 8/2011 | Sutherland et al. |
| 8,009,198 | B2 | 8/2011 | Alhadef |
| 8,019,170 | B2 | 9/2011 | Wang et al. |
| 8,021,231 | B2 | 9/2011 | Walker et al. |
| 8,022,982 | B2 | 9/2011 | Thorn |
| 8,024,026 | B2 | 9/2011 | Groszmann |
| 8,031,909 | B2 | 10/2011 | Se et al. |
| 8,031,933 | B2 | 10/2011 | Se et al. |
| 8,036,425 | B2 | 10/2011 | Hou |
| 8,041,077 | B2 | 10/2011 | Bell |
| 8,041,412 | B2 | 10/2011 | Glossop et al. |
| 8,048,002 | B2 | 11/2011 | Ghajar |
| 8,049,867 | B2 | 11/2011 | Bridges et al. |
| 8,055,020 | B2 | 11/2011 | Meuter et al. |
| 8,055,049 | B2 | 11/2011 | Stayman et al. |
| 8,060,185 | B2 | 11/2011 | Hunter et al. |
| 8,063,929 | B2 | 11/2011 | Kurtz et al. |
| 8,073,197 | B2 | 12/2011 | Xu et al. |
| 8,077,914 | B1 | 12/2011 | Kaplan |
| 8,085,302 | B2 | 12/2011 | Zhang et al. |
| 8,086,026 | B2 | 12/2011 | Schulz |
| 8,086,299 | B2 | 12/2011 | Adler et al. |
| RE43,147 | E | 1/2012 | Aviv |
| 8,094,193 | B2 | 1/2012 | Peterson |
| 8,095,203 | B2 | 1/2012 | Wright et al. |
| 8,095,209 | B2 | 1/2012 | Flaherty |
| 8,098,889 | B2 | 1/2012 | Zhu et al. |
| 8,113,991 | B2 | 2/2012 | Kutliroff |
| 8,116,527 | B2 | 2/2012 | Sabol |
| 8,121,356 | B2 | 2/2012 | Friedman |
| 8,121,361 | B2 | 2/2012 | Ernst et al. |
| 8,134,597 | B2 | 3/2012 | Thorn |
| 8,135,201 | B2 | 3/2012 | Smith et al. |
| 8,139,029 | B2 | 3/2012 | Boillot |
| 8,139,896 | B1 | 3/2012 | Ahiska |
| 8,144,118 | B2 | 3/2012 | Hildreth |
| 8,144,148 | B2 | 3/2012 | El Dokor |
| 8,150,063 | B2 | 4/2012 | Chen |
| 8,150,498 | B2 | 4/2012 | Gielen et al. |
| 8,160,304 | B2 | 4/2012 | Rhoads |
| 8,165,844 | B2 | 4/2012 | Luinge et al. |
| 8,167,802 | B2 | 5/2012 | Baba et al. |
| 8,172,573 | B2 | 5/2012 | Sonenfeld et al. |
| 8,175,332 | B2 | 5/2012 | Herrington |
| 8,179,604 | B1 | 5/2012 | Prada Gomez et al. |
| 8,180,428 | B2 | 5/2012 | Kaiser et al. |
| 8,180,432 | B2 | 5/2012 | Sayeh |
| 8,187,097 | B1 | 5/2012 | Zhang |
| 8,189,869 | B2 | 5/2012 | Bell |
| 8,189,889 | B2 | 5/2012 | Pearlstein et al. |
| 8,189,926 | B2 | 5/2012 | Sharma |
| 8,190,233 | B2 | 5/2012 | Dempsey |
| 8,191,359 | B2 | 6/2012 | White et al. |
| 8,194,134 | B2 | 6/2012 | Furukawa |
| 8,195,084 | B2 | 6/2012 | Xiao |
| 8,199,983 | B2 | 6/2012 | Qureshi |
| 8,206,219 | B2 | 6/2012 | Shum |
| 8,207,967 | B1 | 6/2012 | El Dokor |
| 8,208,758 | B2 | 6/2012 | Wang |
| 8,213,693 | B1 | 7/2012 | Li |
| 8,214,012 | B2 | 7/2012 | Zuccolotto et al. |
| 8,214,016 | B2 | 7/2012 | Lavallee et al. |
| 8,216,016 | B2 | 7/2012 | Yamagishi et al. |
| 8,218,818 | B2 | 7/2012 | Cobb |
| 8,218,819 | B2 | 7/2012 | Cobb |
| 8,218,825 | B2 | 7/2012 | Gordon |
| 8,221,399 | B2 | 7/2012 | Amano |
| 8,223,147 | B1 | 7/2012 | El Dokor |
| 8,224,423 | B2 | 7/2012 | Faul |
| 8,226,574 | B2 | 7/2012 | Whillock |
| 8,229,163 | B2 | 7/2012 | Coleman |
| 8,229,166 | B2 | 7/2012 | Teng |
| 8,229,184 | B2 | 7/2012 | Benkley |
| 8,232,872 | B2 | 7/2012 | Zeng |
| 8,235,529 | B1 | 8/2012 | Raffle |
| 8,235,530 | B2 | 8/2012 | Maad |
| 8,241,125 | B2 | 8/2012 | Hughes |
| 8,243,136 | B2 | 8/2012 | Aota |
| 8,243,269 | B2 | 8/2012 | Matousek |
| 8,243,996 | B2 | 8/2012 | Steinberg |
| 8,248,372 | B2 | 8/2012 | Saila |
| 8,249,691 | B2 | 8/2012 | Chase et al. |
| 8,253,770 | B2 | 8/2012 | Kurtz |
| 8,253,774 | B2 | 8/2012 | Huitema |
| 8,253,778 | B2 | 8/2012 | Atsushi |
| 8,259,109 | B2 | 9/2012 | El Dokor |
| 8,260,036 | B2 | 9/2012 | Hamza et al. |
| 8,279,288 | B2 | 10/2012 | Son |
| 8,284,157 | B2 | 10/2012 | Markovic |
| 8,284,847 | B2 | 10/2012 | Adermann |
| 8,287,373 | B2 | 10/2012 | Marks et al. |
| 8,289,390 | B2 | 10/2012 | Aggarwal |
| 8,289,392 | B2 | 10/2012 | Senior et al. |
| 8,290,208 | B2 | 10/2012 | Kurtz |
| 8,290,229 | B2 | 10/2012 | Qureshi |
| 8,295,573 | B2 | 10/2012 | Bredno et al. |
| 8,301,226 | B2 | 10/2012 | Csavoy et al. |
| 8,306,260 | B2 | 11/2012 | Zhu |
| 8,306,267 | B1 | 11/2012 | Gossweiler, III |
| 8,306,274 | B2 | 11/2012 | Grycewicz |
| 8,306,663 | B2 | 11/2012 | Wickham |
| 8,310,656 | B2 | 11/2012 | Zalewski |
| 8,310,662 | B2 | 11/2012 | Mehr |
| 8,311,611 | B2 | 11/2012 | Csavoy et al. |
| 8,314,854 | B2 | 11/2012 | Yoon |
| 8,315,691 | B2 | 11/2012 | Sumanaweera et al. |
| 8,316,324 | B2 | 11/2012 | Boillot |
| 8,320,621 | B2 | 11/2012 | McEldowney |
| 8,320,709 | B2 | 11/2012 | Arartani et al. |

(56) References Cited

U.S. PATENT DOCUMENTS

| | | |
|---|---|---|
| 8,323,106 B2 | 12/2012 | Zalewski |
| 8,325,228 B2 | 12/2012 | Mariadoss |
| 8,330,811 B2 | 12/2012 | Maguire, Jr. |
| 8,330,812 B2 | 12/2012 | Maguire, Jr. |
| 8,331,019 B2 | 12/2012 | Cheong |
| 8,334,900 B2 | 12/2012 | Qu et al. |
| 8,339,282 B2 | 12/2012 | Noble |
| 8,351,651 B2 | 1/2013 | Lee |
| 8,368,586 B2 | 2/2013 | Mohamadi |
| 8,369,574 B2 | 2/2013 | Hu |
| 8,374,393 B2 | 2/2013 | Cobb |
| 8,374,411 B2 | 2/2013 | Ernst et al. |
| 8,374,674 B2 | 2/2013 | Gertner |
| 8,376,226 B2 | 2/2013 | Dennard |
| 8,376,827 B2 | 2/2013 | Cammegh |
| 8,379,927 B2 | 2/2013 | Taylor |
| 8,380,284 B2 | 2/2013 | Saranathan et al. |
| 8,386,011 B2 | 2/2013 | Wieczorek |
| 8,390,291 B2 | 3/2013 | Macfarlane et al. |
| 8,390,729 B2 | 3/2013 | Long |
| 8,395,620 B2 | 3/2013 | El Dokor |
| 8,396,654 B1 | 3/2013 | Simmons et al. |
| 8,400,398 B2 | 3/2013 | Schoen |
| 8,400,490 B2 | 3/2013 | Apostolopoulos |
| 8,405,491 B2 | 3/2013 | Fong |
| 8,405,656 B2 | 3/2013 | El Dokor |
| 8,405,717 B2 | 3/2013 | Kim |
| 8,406,845 B2 | 3/2013 | Komistek et al. |
| 8,411,931 B2 | 4/2013 | Zhou |
| 8,427,538 B2 | 4/2013 | Ahiska |
| 8,428,319 B2 | 4/2013 | Tsin et al. |
| 8,571,293 B2 | 10/2013 | Ernst et al. |
| 8,600,213 B2 | 12/2013 | Mestha et al. |
| 8,615,127 B2 | 12/2013 | Fitzpatrick |
| 8,617,081 B2 | 12/2013 | Mestha et al. |
| 8,744,154 B2 | 6/2014 | Van Den Brink |
| 8,747,382 B2 | 6/2014 | D'Souza |
| 8,768,438 B2 | 7/2014 | Mestha et al. |
| 8,790,269 B2 | 7/2014 | Xu et al. |
| 8,792,969 B2 | 7/2014 | Bernal et al. |
| 8,805,019 B2 | 8/2014 | Jeanne et al. |
| 8,848,977 B2 | 9/2014 | Bammer et al. |
| 8,855,384 B2 | 10/2014 | Kyal et al. |
| 8,862,420 B2 | 10/2014 | Ferran et al. |
| 8,873,812 B2 | 10/2014 | Larlus-Larrondo et al. |
| 8,953,847 B2 | 2/2015 | Moden |
| 8,971,985 B2 | 3/2015 | Bernal et al. |
| 8,977,347 B2 | 3/2015 | Mestha et al. |
| 8,995,754 B2 | 3/2015 | Wu et al. |
| 8,996,094 B2 | 3/2015 | Schouenborg et al. |
| 9,020,185 B2 | 4/2015 | Mestha et al. |
| 9,036,877 B2 | 5/2015 | Kyal et al. |
| 9,076,212 B2 | 7/2015 | Ernst et al. |
| 9,082,177 B2 | 7/2015 | Sebok |
| 9,084,629 B1 | 7/2015 | Rosa |
| 9,103,897 B2 | 8/2015 | Herbst et al. |
| 9,138,175 B2 | 9/2015 | Ernst et al. |
| 9,173,715 B2 | 11/2015 | Baumgartner |
| 9,176,932 B2 | 11/2015 | Baggen et al. |
| 9,194,929 B2 | 11/2015 | Siegert et al. |
| 9,226,691 B2 | 1/2016 | Bernal et al. |
| 9,305,365 B2 | 4/2016 | Lovberg et al. |
| 9,318,012 B2 | 4/2016 | Johnson |
| 9,336,594 B2 | 5/2016 | Kyal et al. |
| 9,395,386 B2 | 7/2016 | Corder et al. |
| 9,433,386 B2 | 9/2016 | Mestha et al. |
| 9,436,277 B2 | 9/2016 | Furst et al. |
| 9,443,289 B2 | 9/2016 | Xu et al. |
| 9,451,926 B2 | 9/2016 | Kinahan et al. |
| 9,453,898 B2 | 9/2016 | Nielsen et al. |
| 9,504,426 B2 | 11/2016 | Kyal et al. |
| 9,606,209 B2 | 3/2017 | Ernst et al. |
| 9,607,377 B2 | 3/2017 | Lovberg et al. |
| 9,629,595 B2 | 4/2017 | Walker |
| 9,693,710 B2 | 7/2017 | Mestha et al. |
| 9,734,589 B2 | 8/2017 | Yu et al. |
| 9,779,502 B1 | 10/2017 | Lovberg et al. |
| 2002/0082496 A1 | 6/2002 | Kuth |
| 2002/0087101 A1 | 7/2002 | Barrick et al. |
| 2002/0091422 A1 | 7/2002 | Greenberg et al. |
| 2002/0115931 A1 | 8/2002 | Strauss et al. |
| 2002/0180436 A1 | 12/2002 | Dale et al. |
| 2002/0188194 A1 | 12/2002 | Cosman |
| 2003/0063292 A1 | 4/2003 | Mostafavi |
| 2003/0088177 A1 | 5/2003 | Totterman et al. |
| 2003/0116166 A1 | 6/2003 | Anthony |
| 2003/0130574 A1 | 7/2003 | Stoyle |
| 2003/0195526 A1 | 10/2003 | Vilsmeir |
| 2004/0071324 A1 | 4/2004 | Norris et al. |
| 2004/0116804 A1 | 6/2004 | Mostafavi |
| 2004/0140804 A1 | 7/2004 | Polzin et al. |
| 2004/0171927 A1 | 9/2004 | Lowen et al. |
| 2005/0027194 A1 | 2/2005 | Adler et al. |
| 2005/0054910 A1 | 3/2005 | Tremblay et al. |
| 2005/0070784 A1 | 3/2005 | Komura et al. |
| 2005/0105772 A1 | 5/2005 | Voronka et al. |
| 2005/0107685 A1 | 5/2005 | Seeber |
| 2005/0137475 A1 | 6/2005 | Dold et al. |
| 2005/0148845 A1 | 7/2005 | Dean et al. |
| 2005/0148854 A1 | 7/2005 | Ito et al. |
| 2005/0265516 A1* | 12/2005 | Haider ............... A61B 5/0555 378/20 |
| 2005/0283068 A1 | 12/2005 | Zuccoloto et al. |
| 2006/0004281 A1 | 1/2006 | Saracen |
| 2006/0045310 A1 | 3/2006 | Tu et al. |
| 2006/0074292 A1 | 4/2006 | Thomson et al. |
| 2006/0241405 A1 | 10/2006 | Leitner et al. |
| 2007/0049794 A1 | 3/2007 | Glassenberg et al. |
| 2007/0093709 A1 | 4/2007 | Abernathie |
| 2007/0206836 A1 | 9/2007 | Yoon |
| 2007/0239169 A1 | 10/2007 | Plaskos et al. |
| 2007/0280508 A1 | 12/2007 | Ernst et al. |
| 2008/0039713 A1 | 2/2008 | Thomson et al. |
| 2008/0181358 A1 | 7/2008 | Van Kampen et al. |
| 2008/0183074 A1 | 7/2008 | Carls et al. |
| 2008/0212835 A1 | 9/2008 | Tavor |
| 2008/0221442 A1 | 9/2008 | Tolowsky et al. |
| 2008/0273754 A1 | 11/2008 | Hick et al. |
| 2008/0287728 A1 | 11/2008 | Hassan et al. |
| 2008/0287780 A1 | 11/2008 | Chase et al. |
| 2008/0317313 A1 | 12/2008 | Goddard et al. |
| 2009/0028411 A1 | 1/2009 | Pfeuffer |
| 2009/0052760 A1 | 2/2009 | Smith et al. |
| 2009/0185663 A1 | 7/2009 | Gaines, Jr. et al. |
| 2009/0187112 A1 | 7/2009 | Meir et al. |
| 2009/0209846 A1 | 8/2009 | Bammer |
| 2009/0253985 A1 | 10/2009 | Shachar et al. |
| 2009/0304297 A1 | 12/2009 | Adabala et al. |
| 2009/0306499 A1 | 12/2009 | Van Vorhis et al. |
| 2010/0054579 A1 | 3/2010 | Okutomi |
| 2010/0057059 A1 | 3/2010 | Makino |
| 2010/0059679 A1 | 3/2010 | Albrecht |
| 2010/0069742 A1 | 3/2010 | Partain et al. |
| 2010/0091089 A1 | 4/2010 | Cromwell et al. |
| 2010/0099981 A1 | 4/2010 | Fishel |
| 2010/0125191 A1 | 5/2010 | Sahin |
| 2010/0137709 A1 | 6/2010 | Gardner et al. |
| 2010/0148774 A1 | 6/2010 | Kamata |
| 2010/0149099 A1 | 6/2010 | Elias |
| 2010/0149315 A1 | 6/2010 | Qu |
| 2010/0160775 A1 | 6/2010 | Pankratov |
| 2010/0164862 A1 | 7/2010 | Sullivan |
| 2010/0165293 A1 | 7/2010 | Tanassi et al. |
| 2010/0167246 A1 | 7/2010 | Ghajar |
| 2010/0172567 A1 | 7/2010 | Prokoski |
| 2010/0177929 A1 | 7/2010 | Kurtz |
| 2010/0178966 A1 | 7/2010 | Suydoux |
| 2010/0179390 A1 | 7/2010 | Davis |
| 2010/0179413 A1 | 7/2010 | Kadour et al. |
| 2010/0183196 A1 | 7/2010 | Fu et al. |
| 2010/0191631 A1 | 7/2010 | Weidmann |
| 2010/0194879 A1 | 8/2010 | Pasveer |
| 2010/0198067 A1 | 8/2010 | Mahfouz |
| 2010/0198101 A1 | 8/2010 | Song |

(56) References Cited

U.S. PATENT DOCUMENTS

| | | |
|---|---|---|
| 2010/0198112 A1 | 8/2010 | Maad |
| 2010/0199232 A1 | 8/2010 | Mistry |
| 2010/0210350 A9 | 8/2010 | Walker |
| 2010/0214267 A1 | 8/2010 | Radivojevic |
| 2010/0231511 A1 | 9/2010 | Henty |
| 2010/0231692 A1 | 9/2010 | Perlman |
| 2010/0245536 A1 | 9/2010 | Huitema |
| 2010/0245593 A1 | 9/2010 | Kim |
| 2010/0251924 A1 | 10/2010 | Taylor |
| 2010/0253762 A1 | 10/2010 | Cheong |
| 2010/0268072 A1 | 10/2010 | Hall et al. |
| 2010/0277571 A1 | 11/2010 | Xu |
| 2010/0282902 A1 | 11/2010 | Rajasingham |
| 2010/0283833 A1 | 11/2010 | Yeh |
| 2010/0284119 A1 | 11/2010 | Coakley |
| 2010/0289899 A1 | 11/2010 | Hendron |
| 2010/0290668 A1 | 11/2010 | Friedman |
| 2010/0292841 A1 | 11/2010 | Wickham |
| 2010/0295718 A1 | 11/2010 | Mohamadi |
| 2010/0296701 A1 | 11/2010 | Hu |
| 2010/0302142 A1 | 12/2010 | French |
| 2010/0303289 A1 | 12/2010 | Polzin |
| 2010/0311512 A1 | 12/2010 | Lock |
| 2010/0321505 A1 | 12/2010 | Kokubun |
| 2010/0328055 A1 | 12/2010 | Fong |
| 2010/0328201 A1 | 12/2010 | Marbit |
| 2010/0328267 A1 | 12/2010 | Chen |
| 2010/0330912 A1 | 12/2010 | Saila |
| 2011/0001699 A1 | 1/2011 | Jacobsen |
| 2011/0006991 A1 | 1/2011 | Elias |
| 2011/0007939 A1 | 1/2011 | Teng |
| 2011/0007946 A1 | 1/2011 | Liang |
| 2011/0008759 A1 | 1/2011 | Usui |
| 2011/0015521 A1 | 1/2011 | Faul |
| 2011/0019001 A1 | 1/2011 | Rhoads |
| 2011/0025853 A1 | 2/2011 | Richardson |
| 2011/0038520 A1 | 2/2011 | Yui |
| 2011/0043631 A1 | 2/2011 | Marman |
| 2011/0043759 A1 | 2/2011 | Bushinsky |
| 2011/0050562 A1 | 3/2011 | Schoen |
| 2011/0050569 A1 | 3/2011 | Marvit |
| 2011/0050947 A1 | 3/2011 | Marman |
| 2011/0052002 A1 | 3/2011 | Cobb |
| 2011/0052003 A1 | 3/2011 | Cobb |
| 2011/0052015 A1 | 3/2011 | Saund |
| 2011/0054870 A1 | 3/2011 | Dariush |
| 2011/0057816 A1 | 3/2011 | Noble |
| 2011/0058020 A1 | 3/2011 | Dieckmann |
| 2011/0064290 A1 | 3/2011 | Punithakaumar |
| 2011/0069207 A1 | 3/2011 | Steinberg |
| 2011/0074675 A1 | 3/2011 | Shiming |
| 2011/0081000 A1 | 4/2011 | Gertner |
| 2011/0081043 A1 | 4/2011 | Sabol |
| 2011/0085704 A1 | 4/2011 | Han |
| 2011/0092781 A1 | 4/2011 | Gertner |
| 2011/0102549 A1 | 5/2011 | Takahashi |
| 2011/0105883 A1 | 5/2011 | Lake et al. |
| 2011/0105893 A1 | 5/2011 | Akins et al. |
| 2011/0115793 A1 | 5/2011 | Grycewicz |
| 2011/0115892 A1 | 5/2011 | Fan |
| 2011/0116683 A1 | 5/2011 | Kramer et al. |
| 2011/0117528 A1 | 5/2011 | Marciello et al. |
| 2011/0118032 A1 | 5/2011 | Zalewski |
| 2011/0133917 A1 | 6/2011 | Zeng |
| 2011/0142411 A1 | 6/2011 | Camp |
| 2011/0150271 A1 | 6/2011 | Lee |
| 2011/0157168 A1 | 6/2011 | Bennett |
| 2011/0157358 A1 | 6/2011 | Bell |
| 2011/0157370 A1 | 6/2011 | Livesey |
| 2011/0160569 A1 | 6/2011 | Cohen et al. |
| 2011/0172060 A1 | 7/2011 | Morales |
| 2011/0172521 A1 | 7/2011 | Zdeblick et al. |
| 2011/0175801 A1 | 7/2011 | Markovic |
| 2011/0175809 A1 | 7/2011 | Markovic |
| 2011/0175810 A1 | 7/2011 | Markovic |
| 2011/0176723 A1 | 7/2011 | Ali et al. |
| 2011/0180695 A1 | 7/2011 | Li |
| 2011/0181893 A1 | 7/2011 | MacFarlane |
| 2011/0182472 A1 | 7/2011 | Hansen |
| 2011/0187640 A1 | 8/2011 | Jacobsen |
| 2011/0193939 A1 | 8/2011 | Vassigh |
| 2011/0199461 A1 | 8/2011 | Horio |
| 2011/0201916 A1 | 8/2011 | Duyn et al. |
| 2011/0201939 A1 | 8/2011 | Hubschman et al. |
| 2011/0202306 A1 | 8/2011 | Eng |
| 2011/0205358 A1 | 8/2011 | Aota |
| 2011/0207089 A1 | 8/2011 | Lagettie |
| 2011/0208437 A1 | 8/2011 | Teicher |
| 2011/0216002 A1 | 9/2011 | Weising |
| 2011/0216180 A1 | 9/2011 | Pasini |
| 2011/0221770 A1 | 9/2011 | Kruglick |
| 2011/0229862 A1 | 9/2011 | Parikh |
| 2011/0230755 A1 | 9/2011 | MacFarlane et al. |
| 2011/0234807 A1 | 9/2011 | Jones |
| 2011/0234834 A1 | 9/2011 | Sugimoto |
| 2011/0235855 A1 | 9/2011 | Smith |
| 2011/0237933 A1 | 9/2011 | Cohen |
| 2011/0242134 A1 | 10/2011 | Miller |
| 2011/0244939 A1 | 10/2011 | Cammegh |
| 2011/0250929 A1 | 10/2011 | Lin |
| 2011/0251478 A1 | 10/2011 | Wieczorek |
| 2011/0255845 A1 | 10/2011 | Kikuchi |
| 2011/0257566 A1 | 10/2011 | Burdea |
| 2011/0260965 A1 | 10/2011 | Kim |
| 2011/0262002 A1 | 10/2011 | Lee |
| 2011/0267427 A1 | 11/2011 | Goh |
| 2011/0267456 A1 | 11/2011 | Adermann |
| 2011/0275957 A1 | 11/2011 | Bhandari |
| 2011/0276396 A1 | 11/2011 | Rathod |
| 2011/0279663 A1 | 11/2011 | Fan |
| 2011/0285622 A1 | 11/2011 | Marti |
| 2011/0286010 A1 | 11/2011 | Kusik et al. |
| 2011/0291925 A1 | 12/2011 | Israel |
| 2011/0293143 A1 | 12/2011 | Narayanan et al. |
| 2011/0293146 A1 | 12/2011 | Grycewicz |
| 2011/0298708 A1 | 12/2011 | Hsu |
| 2011/0298824 A1 | 12/2011 | Lee |
| 2011/0300994 A1 | 12/2011 | Verkaaik |
| 2011/0301449 A1 | 12/2011 | Maurer, Jr. |
| 2011/0301934 A1 | 12/2011 | Tardis |
| 2011/0303214 A1 | 12/2011 | Welle |
| 2011/0304541 A1 | 12/2011 | Dalal |
| 2011/0304650 A1 | 12/2011 | Campillo |
| 2011/0304706 A1 | 12/2011 | Porter |
| 2011/0306867 A1 | 12/2011 | Gopinadhan |
| 2011/0310220 A1 | 12/2011 | McEldowney |
| 2011/0310226 A1 | 12/2011 | McEldowney |
| 2011/0316994 A1 | 12/2011 | Lemchen |
| 2011/0317877 A1 | 12/2011 | Bell |
| 2012/0002112 A1 | 1/2012 | Huang |
| 2012/0004791 A1 | 1/2012 | Buelthoff |
| 2012/0007839 A1 | 1/2012 | Tsao et al. |
| 2012/0019645 A1 | 1/2012 | Maltz |
| 2012/0020524 A1 | 1/2012 | Ishikawa |
| 2012/0021806 A1 | 1/2012 | Naltz |
| 2012/0027226 A1 | 2/2012 | Desenberg |
| 2012/0029345 A1 | 2/2012 | Mahfouz et al. |
| 2012/0032882 A1 | 2/2012 | Schlachta |
| 2012/0033083 A1 | 2/2012 | Horvinger |
| 2012/0035462 A1 | 2/2012 | Maurer, Jr. et al. |
| 2012/0039505 A1 | 2/2012 | Vastide |
| 2012/0044363 A1 | 2/2012 | Lu |
| 2012/0045091 A1 | 2/2012 | Kaganovich |
| 2012/0049453 A1 | 3/2012 | Morichau-Beauchant et al. |
| 2012/0051588 A1 | 3/2012 | McEldowney |
| 2012/0051664 A1 | 3/2012 | Gopalakrishnan et al. |
| 2012/0052949 A1 | 3/2012 | Weitzner |
| 2012/0056982 A1 | 3/2012 | Katz |
| 2012/0057640 A1 | 3/2012 | Shi |
| 2012/0065492 A1 | 3/2012 | Gertner et al. |
| 2012/0065494 A1 | 3/2012 | Gertner et al. |
| 2012/0072041 A1 | 3/2012 | Miller |
| 2012/0075166 A1 | 3/2012 | Marti |
| 2012/0075177 A1 | 3/2012 | Jacobsen |

(56) References Cited

U.S. PATENT DOCUMENTS

| | | |
|---|---|---|
| 2012/0076369 A1 | 3/2012 | Abramovich |
| 2012/0081504 A1 | 4/2012 | Ng |
| 2012/0083314 A1 | 4/2012 | Ng |
| 2012/0083960 A1 | 4/2012 | Zhu |
| 2012/0086778 A1 | 4/2012 | Lee |
| 2012/0086809 A1 | 4/2012 | Lee |
| 2012/0092445 A1 | 4/2012 | McDowell |
| 2012/0092502 A1 | 4/2012 | Knasel |
| 2012/0093481 A1 | 4/2012 | McDowell |
| 2012/0098938 A1 | 4/2012 | Jin |
| 2012/0101388 A1 | 4/2012 | Tripathi |
| 2012/0105573 A1 | 5/2012 | Apostolopoulos |
| 2012/0106814 A1 | 5/2012 | Gleason et al. |
| 2012/0108909 A1 | 5/2012 | Slobounov et al. |
| 2012/0113140 A1 | 5/2012 | Hilliges |
| 2012/0113223 A1 | 5/2012 | Hilliges |
| 2012/0116202 A1 | 5/2012 | Bangera |
| 2012/0119999 A1 | 5/2012 | Harris |
| 2012/0120072 A1 | 5/2012 | Se |
| 2012/0120237 A1 | 5/2012 | Trepess |
| 2012/0120243 A1 | 5/2012 | Chien |
| 2012/0120277 A1 | 5/2012 | Tsai |
| 2012/0121124 A1 | 5/2012 | Bammer |
| 2012/0124604 A1 | 5/2012 | Small |
| 2012/0127319 A1 | 5/2012 | Rao |
| 2012/0133616 A1 | 5/2012 | Nishihara |
| 2012/0133889 A1 | 5/2012 | Bergt |
| 2012/0143029 A1 | 6/2012 | Silverstein |
| 2012/0143212 A1 | 6/2012 | Madhani |
| 2012/0147167 A1 | 6/2012 | Manson |
| 2012/0154272 A1 | 6/2012 | Hildreth |
| 2012/0154511 A1 | 6/2012 | Hsu |
| 2012/0154536 A1 | 6/2012 | Stoker |
| 2012/0154579 A1 | 6/2012 | Hanpapur |
| 2012/0156661 A1 | 6/2012 | Smith |
| 2012/0158197 A1 | 6/2012 | Hinman |
| 2012/0162378 A1 | 6/2012 | El Dokor et al. |
| 2012/0165964 A1 | 6/2012 | Flaks |
| 2012/0167143 A1 | 6/2012 | Longet |
| 2012/0169841 A1 | 7/2012 | Chemali |
| 2012/0176314 A1 | 7/2012 | Jeon |
| 2012/0184371 A1 | 7/2012 | Shum |
| 2012/0188237 A1 | 7/2012 | Han |
| 2012/0188371 A1 | 7/2012 | Chen |
| 2012/0194422 A1 | 8/2012 | El Dokor |
| 2012/0194517 A1 | 8/2012 | Izadi et al. |
| 2012/0194561 A1 | 8/2012 | Grossinger |
| 2012/0195466 A1 | 8/2012 | Teng |
| 2012/0196660 A1 | 8/2012 | El Dokor et al. |
| 2012/0197135 A1 | 8/2012 | Slatkine |
| 2012/0200676 A1 | 8/2012 | Huitema |
| 2012/0201428 A1 | 8/2012 | Joshi et al. |
| 2012/0206604 A1 | 8/2012 | Jones |
| 2012/0212594 A1 | 8/2012 | Nick Barns |
| 2012/0218407 A1 | 8/2012 | Chien |
| 2012/0218421 A1 | 8/2012 | Chien |
| 2012/0220233 A1 | 8/2012 | Teague |
| 2012/0224666 A1 | 9/2012 | Speller |
| 2012/0224743 A1 | 9/2012 | Rodriguez |
| 2012/0225718 A1 | 9/2012 | Zhang |
| 2012/0229643 A1 | 9/2012 | Chidanand |
| 2012/0229651 A1 | 9/2012 | Takizawa |
| 2012/0230561 A1 | 9/2012 | Qureshi |
| 2012/0235896 A1 | 9/2012 | Jacobsen |
| 2012/0238337 A1 | 9/2012 | French |
| 2012/0242816 A1 | 9/2012 | Cruz |
| 2012/0249741 A1 | 10/2012 | Maciocci |
| 2012/0253201 A1 | 10/2012 | Reinhold |
| 2012/0253241 A1 | 10/2012 | Levital et al. |
| 2012/0262540 A1 | 10/2012 | Rondinelli |
| 2012/0262558 A1 | 10/2012 | Boger |
| 2012/0262583 A1 | 10/2012 | Bernal |
| 2012/0268124 A1 | 10/2012 | Herbst et al. |
| 2012/0275649 A1 | 11/2012 | Cobb |
| 2012/0276995 A1 | 11/2012 | Lansdale |
| 2012/0277001 A1 | 11/2012 | Lansdale |
| 2012/0281093 A1 | 11/2012 | Fong |
| 2012/0281873 A1 | 11/2012 | Brown |
| 2012/0288142 A1 | 11/2012 | Gossweiler, III |
| 2012/0288143 A1 | 11/2012 | Ernst |
| 2012/0288852 A1 | 11/2012 | Willson |
| 2012/0289334 A9 | 11/2012 | Mikhailov |
| 2012/0289822 A1 | 11/2012 | Shachar et al. |
| 2012/0293412 A1 | 11/2012 | El Dokor |
| 2012/0293506 A1 | 11/2012 | Vertucci |
| 2012/0293663 A1 | 11/2012 | Liu |
| 2012/0294511 A1 | 11/2012 | Datta |
| 2012/0300961 A1 | 11/2012 | Moeller |
| 2012/0303839 A1 | 11/2012 | Jackson |
| 2012/0304126 A1 | 11/2012 | Lavigne |
| 2012/0307075 A1 | 12/2012 | Margalit |
| 2012/0307207 A1 | 12/2012 | Abraham |
| 2012/0314066 A1 | 12/2012 | Lee |
| 2012/0315016 A1 | 12/2012 | Fung |
| 2012/0319946 A1 | 12/2012 | El Dokor |
| 2012/0319989 A1 | 12/2012 | Argiro |
| 2012/0320178 A1 | 12/2012 | Siegert et al. |
| 2012/0320219 A1 | 12/2012 | David |
| 2012/0326966 A1 | 12/2012 | Rauber |
| 2012/0326976 A1 | 12/2012 | Markovic |
| 2012/0326979 A1 | 12/2012 | Geisert |
| 2012/0327241 A1 | 12/2012 | Howe |
| 2012/0327246 A1 | 12/2012 | Senior et al. |
| 2013/0002866 A1 | 1/2013 | Hampapur |
| 2013/0002879 A1 | 1/2013 | Weber |
| 2013/0002900 A1 | 1/2013 | Gossweiler, III |
| 2013/0009865 A1 | 1/2013 | Valik |
| 2013/0010071 A1 | 1/2013 | Valik |
| 2013/0013452 A1 | 1/2013 | Dennard |
| 2013/0016009 A1 | 1/2013 | Godfrey |
| 2013/0016876 A1 | 1/2013 | Wooley |
| 2013/0021434 A1 | 1/2013 | Ahiska |
| 2013/0021578 A1 | 1/2013 | Chen |
| 2013/0024819 A1 | 1/2013 | Rieffel |
| 2013/0030283 A1 | 1/2013 | Vortman et al. |
| 2013/0033640 A1 | 2/2013 | Lee |
| 2013/0033700 A1 | 2/2013 | Hallil |
| 2013/0035590 A1 | 2/2013 | Ma et al. |
| 2013/0035612 A1 | 2/2013 | Mason |
| 2013/0040720 A1 | 2/2013 | Cammegh |
| 2013/0041368 A1 | 2/2013 | Cunninghan |
| 2013/0049756 A1 | 2/2013 | Ernst et al. |
| 2013/0053683 A1 | 2/2013 | Hwang et al. |
| 2013/0057702 A1 | 3/2013 | Chavan |
| 2013/0064426 A1 | 3/2013 | Watkins, Jr. |
| 2013/0064427 A1 | 3/2013 | Picard |
| 2013/0065517 A1 | 3/2013 | Svensson |
| 2013/0066448 A1 | 3/2013 | Alonso |
| 2013/0066526 A1 | 3/2013 | Mondragon |
| 2013/0069773 A1 | 3/2013 | Li |
| 2013/0070201 A1 | 3/2013 | Shahidi |
| 2013/0070257 A1 | 3/2013 | Wong |
| 2013/0072787 A1 | 3/2013 | Wallace et al. |
| 2013/0076863 A1 | 3/2013 | Rappel |
| 2013/0076944 A1 | 3/2013 | Kosaka |
| 2013/0077823 A1 | 3/2013 | Mestha |
| 2013/0079033 A1 | 3/2013 | Gupta |
| 2013/0084980 A1 | 4/2013 | Hammontree |
| 2013/0088584 A1 | 4/2013 | Malhas |
| 2013/0093866 A1 | 4/2013 | Ohlhues et al. |
| 2013/0096439 A1 | 4/2013 | Lee |
| 2013/0102879 A1 | 4/2013 | MacLaren et al. |
| 2013/0102893 A1 | 4/2013 | Vollmer |
| 2013/0108979 A1 | 5/2013 | Daon |
| 2013/0113791 A1 | 5/2013 | Isaacs et al. |
| 2013/0211421 A1 | 8/2013 | Abovitz et al. |
| 2013/0281818 A1 | 10/2013 | Vija et al. |
| 2014/0073908 A1 | 3/2014 | Biber |
| 2014/0088410 A1 | 3/2014 | Wu |
| 2014/0148685 A1 | 5/2014 | Liu et al. |
| 2014/0159721 A1 | 6/2014 | Grodzki |
| 2014/0171784 A1 | 6/2014 | Ooi et al. |
| 2014/0343344 A1* | 11/2014 | Saunders ............ A61N 5/107 600/1 |

(56) References Cited

U.S. PATENT DOCUMENTS

| | | |
|---|---|---|
| 2014/0378816 A1 | 12/2014 | Oh et al. |
| 2015/0085072 A1 | 3/2015 | Yan |
| 2015/0094597 A1 | 4/2015 | Mestha et al. |
| 2015/0094606 A1 | 4/2015 | Mestha et al. |
| 2015/0212182 A1 | 7/2015 | Nielsen et al. |
| 2015/0245787 A1 | 9/2015 | Kyal et al. |
| 2015/0257661 A1 | 9/2015 | Mestha et al. |
| 2015/0265187 A1 | 9/2015 | Bernal et al. |
| 2015/0265220 A1 | 9/2015 | Ernst et al. |
| 2015/0297120 A1 | 10/2015 | Son et al. |
| 2015/0297314 A1 | 10/2015 | Fowler |
| 2015/0316635 A1 | 11/2015 | Stehning et al. |
| 2015/0323637 A1 | 11/2015 | Beck et al. |
| 2015/0331078 A1 | 11/2015 | Speck et al. |
| 2015/0359464 A1 | 12/2015 | Oleson |
| 2015/0366527 A1 | 12/2015 | Yu et al. |
| 2016/0000383 A1 | 1/2016 | Lee et al. |
| 2016/0000411 A1 | 1/2016 | Raju et al. |
| 2016/0035108 A1 | 2/2016 | Yu et al. |
| 2016/0045112 A1 | 2/2016 | Weissler et al. |
| 2016/0073962 A1 | 3/2016 | Yu et al. |
| 2016/0091592 A1 | 3/2016 | Beall et al. |
| 2016/0166205 A1 | 6/2016 | Ernst et al. |
| 2016/0189372 A1 | 6/2016 | Lovberg et al. |
| 2016/0198965 A1 | 7/2016 | Mestha et al. |
| 2016/0228005 A1 | 8/2016 | Bammer et al. |
| 2016/0249984 A1 | 9/2016 | Janssen |
| 2016/0256713 A1 | 9/2016 | Saunders et al. |
| 2016/0262663 A1 | 9/2016 | MacLaren et al. |
| 2016/0287080 A1 | 10/2016 | Olesen et al. |
| 2016/0310093 A1* | 10/2016 | Chen ............... A61B 6/032 |
| 2016/0310229 A1 | 10/2016 | Bammer et al. |
| 2016/0313432 A1 | 10/2016 | Feiweier et al. |
| 2017/0032538 A1 | 2/2017 | Ernst et al. |
| 2017/0038449 A1 | 2/2017 | Voigt et al. |
| 2017/0303859 A1 | 10/2017 | Robertson et al. |
| 2017/0319143 A1 | 11/2017 | Yu et al. |
| 2017/0345145 A1 | 11/2017 | Nempont et al. |

FOREIGN PATENT DOCUMENTS

| | | |
|---|---|---|
| CN | 106572810 | 4/2017 |
| CN | 106714681 | 5/2017 |
| DE | 29519078 | 3/1996 |
| DE | 102004024470 | 12/2005 |
| EP | 0904733 | 3/1991 |
| EP | 1319368 | 6/2003 |
| EP | 1354564 | 10/2003 |
| EP | 1524626 | 4/2005 |
| EP | 2515139 | 10/2012 |
| EP | 2948056 | 12/2015 |
| EP | 2950714 | 12/2015 |
| JP | 03023838 | 5/1991 |
| WO | WO 96/17258 | 6/1996 |
| WO | WO 99/38449 | 8/1999 |
| WO | WO 00/72039 | 11/2000 |
| WO | WO 03/003796 | 1/2003 |
| WO | WO 2004/023783 | 3/2004 |
| WO | WO 2005/077293 | 8/2005 |
| WO | WO 2007/025301 | 3/2007 |
| WO | WO 2007/085241 A1 | 8/2007 |
| WO | WO 2007/136745 | 11/2007 |
| WO | WO 2009/101566 | 8/2009 |
| WO | WO 2009/129457 A1 | 10/2009 |
| WO | WO 2010/066824 | 6/2010 |
| WO | WO 2011/047467 A1 | 4/2011 |
| WO | WO 2011/113441 A2 | 9/2011 |
| WO | WO 2012/046202 A1 | 4/2012 |
| WO | WO 2013/032933 A2 | 3/2013 |
| WO | WO 2014/005178 | 1/2014 |
| WO | WO 2014/116868 | 7/2014 |
| WO | WO 2014/120734 | 8/2014 |
| WO | WO 2015/022684 | 2/2015 |
| WO | WO 2015/042138 | 3/2015 |
| WO | WO 2015/092593 | 6/2015 |
| WO | WO 2015/148391 | 10/2015 |
| WO | WO 2016/014718 | 1/2016 |
| WO | WO2017/091479 | 6/2017 |
| WO | WO2017/189427 | 11/2017 |

OTHER PUBLICATIONS

Hoff et al., "Analysis of Head Pose Accuracy in Augmented Reality", IEEE Transactions on Visualization and Computer Graphics 6, No. 4 (Oct.-Dec. 2000): 319-334.

Katsuki, et al., "Design of an Artificial Mark to Determine 3D Pose by Monocular Vision", 2003 IEEE International Conference on Robotics and Automation (Cat. No. 03CH37422), Sep. 14-19, 2003, pp. 995-1000 vol. 1.

Kiebel et al., "MRI and PET coregistration-a cross validation of statistical parametric mapping and automated image registration", Neuroimage 5(4):271-279 (1997).

Lerner, "Motion correction in fmri images", Technion-Israel Institute of Technology, Faculty of Computer Science (Feb. 2006).

Speck, et al., "Prospective real-time slice-by-slice Motion Correction for fMRI in Freely Moving Subjects", Magnetic Resonance Materials in Physics, Biology and Medicine, 19(2), 55-61, published May 9, 2006.

Yeo, et al. Motion correction in fMRI by mapping slice-to-volume with concurrent field-inhomogeneity correction:, International Conference on Medical Image Computing and Computer-Assisted Intervention, pp. 752-760 (2004).

Ashouri, H., L. et al., Unobtrusive Estimation of Cardiac Contractility and Stroke vol. Changes Using Ballistocardiogram Measurements on a High Bandwidth Force Plate, Sensors 2016, 16, 787; doi:10.3390/s16060787.

Benchoff, Brian, "Extremely Precise Positional Tracking", https://hackaday.com/2013/10/10/extremely-precise-positional-tracking/, printed on Sep. 16, 2017, in 7 pages.

Communication pursuant to Article 94(3) EPC for application No. 14743670.3, which is an EP application related to the present application, dated Feb. 6, 2018.

Extended Europen Search Report for application No. 14743670.3 which is a EP application related to the present application, dated Aug. 17, 2017.

Extended Europen Search Report for application No. 15769296.3 which is a EP application related to the present application, dated Dec. 22, 2017.

Extended European Search Report for application No. 15824707.2 which is a EP application related to the present dated Apr. 16, 2018.

Gordon, J. W. Certain molar movements of the human body produced by the circulation of the blood. J. Anat. Physiol. 11, 533-536 (1877).

Herbst et al., "Reproduction of Motion Artifacts for Performance Analysis of Prospective Motion Correction in MRI", Magnetic Resonance in Medicine., vol. 71, No. 1, p. 182-190 (Feb. 25, 2013).

Jochen Triesch, et al."Democratic Integration: Self-Organized Integration of Adaptive Cues", Neural Computation., vol. 13, No. 9, dated Sep. 1, 2001, pp. 2049-2074.

Kim, Chang-Sei et al. "Ballistocardiogram: Mechanism and Potential for Unobtrusive Cardiovascular Health Monitoring", Scientific Reports, Aug. 9, 2016.

Maclaren et al., "Prospective Motion Correction in Brain Imaging: A Review" Online Magnetic Resonance in Medicine, vol. 69, No. 3, pp. 621-636 (Mar. 1, 2013.

Olesen et al., "Structured Light 3D Tracking System for Measuring Motions in PET Brain Imaging", Proceedings of SPIE, The International Society for Optical Engineering (ISSN: 0277-786X), vol. 7625:76250X (2010).

Olesen et al., "Motion Tracking in Narrow Spaces: A Structured Light Approach", Lecture Notes in Computer Science (ISSN: 0302-9743)vol. 6363:253-260 (2010).

Olesen et al., "Motion Tracking for Medical Imaging: A Nonvisible Structured Light Tracking Approach", IEEE Transactions on Medical Imaging, vol. 31(1), Jan. 2012.

(56) References Cited

OTHER PUBLICATIONS

Tarvainen, M.P. et al., "An advanced de-trending method with application to HRV analysis," IEEE Trans. Biomed. Eng., vol. 49, No. 2, pp. 172-175, Feb. 2002.
Wilm et al., "Accurate and Simple Calibration of DLP Projector Systems", Proceedings of SPIE, The International Society for Optical Engineering (ISSN: 0277786X), vol. 8979 (2014).
Wilm et al., "Correction of Motion Artifacts for Real-Time Structured Light", R.R. Paulsen and K.S. Pedersen (Eds.): SCIA 2015, LNCS 9127, pp. 142-151 (2015).
US 7,906,604, 10/2010, Bazakos (withdrawn)
Aksoy et al., "Hybrid Prospective and Retrospective Head Motion Correction to Mitigate Cross-Calibration Errors", NIH Publication, Nov. 2012.
Aksoy et al., "Real-Time Optical Motion Correction for Diffusion Tensor Imaging, Magnetic Resonance in Medicine" (Mar. 22, 2011) 66 366-378.
Andrews et al., "Prospective Motion Correction for Magnetic Resonance Spectroscopy Using Single Camera Retro-Grate Reflector Optical Tracking, Journal of Magnetic Resonance Imaging" (Feb. 2011) 33(2): 498-504.
Angeles et al., "The Online Solution of the Hand-Eye Problem", IEEE Transactions on Robotics and Automation, 16(6): 720-731 (Dec. 2000).
Anishenko et al., "A Motion Correction System for Brain Tomography Based on Biologically Motivated Models." 7th IEEE International Conference on Cybernetic Intelligent Systems, dated Sep. 9, 2008, in 9 pages.
Armstrong et al., "RGR-3D: Simple, cheap detection of 6-DOF pose for tele-operation, and robot programming and calibration", In Proc. 2002 Int. Conf. on Robotics and Automation, IEEE, Washington (May 2002).
Bandettini, Peter A., et al., "Processing Strategies for Time-Course Data Sets in Functional MRI of the Human Breain", Magnetic Resonance in Medicine 30: 161-173 (1993).
Barmet et al, Spatiotemporal Magnetic Field Monitoring for MR, Magnetic Resonance in Medicine (Feb. 1, 2008) 60: 187-197.
Bartels, LW, et al., "Endovascular interventional magnetic resonance imaging", Physics in Medicine and Biology 48: R37-R64 (2003).
Carranza-Herrezuelo et al, "Motion estimation of tagged cardiac magnetic resonance images using variational techniques" Elsevier, Computerized Medical Imaging and Graphics 34 (2010), pp. 514-522.
Chou, Jack C. K., et al., "Finding the Position and Orientation of a Sensor on a Robot Manipulator Using Quaternions", The International Journal of Robotics Research, 10(3): 240-254 (Jun. 1991).
Cofaru et al "Improved Newton-Raphson digital image correlation method for full-field displacement and strain calculation," Department of Materials Science and Engineering, Ghent University St-Pietersnieuwstraat, Nov. 20, 2010.
Ernst et al., "A Novel Phase and Frequency Navigator for Proton Magnetic Resonance Spectroscopy Using Water-Suppression Cycling, Magnetic Resonance in Medicine" (Jan. 2011) 65(1): 13-7.
Eviatar et al., "Real time head motion correction for functional MRI", In: Proceedings of the International Society for Magnetic Resonance in Medicine (1999) 269.
Forbes, Kristen P. N., et al., "Propeller MRI: Clinical Testing of a Novel Technique for Quantification and Compensation of Head Motion", Journal of Magnetic Resonance Imaging 14: 215-222 (2001).
Fulton et al., "Correction for Head Movements in Positron Emission Tomography Using an Optical Motion-Tracking System", IEEE Transactions on Nuclear Science, vol. 49(1):116-123 (Feb. 2002).
Glover, Gary H., et al., "Self-Navigated Spiral fMRI: Interleaved versus Single-shot", Magnetic Resonance in Medicine 39: 361-368 (1998).
Gumus et al., "Elimination of DWI signal dropouts using blipped gradients for dynamic restoration of gradient moment", ISMRM 20th Annual Meeting & Exhibition, May 7, 2012.
Herbst et al., "Preventing Signal Dropouts in DWI Using Continous Prospective Motion Correction", Proc. Intl. Soc. Mag. Reson. Med. 19 (May 2011) 170.
Herbst et al., "Prospective Motion Correction With Continuous Gradient Updates in Diffusion Weighted Imaging, Magnetic Resonance in Medicine" (2012) 67:326-338.
Horn, Berthold K. P., "Closed-form solution of absolute orientation using unit quaternions", Journal of the Optical Society of America, vol. 4, p. 629-642 (Apr. 1987).
International Preliminary Report on Patentability for Application No. PCT/US2015/022041, dated Oct. 6, 2016, in 8 pages.
International Preliminary Report on Patentability for Application No. PCT/US2007/011899, dated Jun. 8, 2008, in 13 pages.
International Search Report and Written Opinion for Application No. PCT/US2007/011899, dated Nov. 14, 2007.
International Search Report and Written Opinion for Application No. PCT/US2014/012806, dated May 15, 2014, in 15 pages.
International Search Report and Written Opinion for Application No. PCT/US2015/041615, dated Oct. 29, 2015, in 13 pages.
International Preliminary Report on Patentability for Application No. PCT/US2014/013546, dated Aug. 4, 2015, in 9 pages.
International Search Report and Written Opinion for Application No. PCT/US2015/022041, dated Jun. 29, 2015, in 9 pages.
Josefsson et al. "A flexible high-precision video system for digital recording of motor acts through lightweight reflect markers", Computer Methods and Programs in Biomedicine, vol. 49:111-129 (1996).
Kiruluta et al., "Predictive Head Movement Tracking Using a Kalman Filter", IEEE Trans. On Systems, Man, and Cybernetics—Part B: Cybernetics, 27(2):326-331 (Apr. 1997).
Maclaren et al., "Combined Prospective and Retrospective Motion Correction to Relax Navigator Requirements", Magnetic Resonance in Medicine (Feb. 11, 2011) 65:1724-1732.
MacLaren et al., "Navigator Accuracy Requirements for Prospective Motion Correction", Magnetic Resonance in Medicine (Jan. 2010) 63(1): 162-70.
MacLaren, "Prospective Motion Correction in MRI Using Optical Tracking Tape", Book of Abstracts, ESMRMB (2009).
Maclaren et al., "Measurement and correction of microscopic head motion during magnetic resonance imaging of the brain", PLOS One, vol. 7(11):1-9 (2012).
McVeigh et al., "Real-time, Interactive MRI for Cardiovascular Interventions", Academic Radiology, 12(9): 1121-1127 (2005).
Nehrke et al., "Prospective Correction of Affine Motion for Arbitrary MR Sequences on a Clinical Scanner", Magnetic Resonance in Medicine (Jun. 28, 2005) 54:1130-1138.
Norris et al., "Online motion correction for diffusion-weighted imaging using navigator echoes: application to RARE imaging without sensitivity loss", Magnetic Resonance in Medicine, vol. 45:729-733 (2001).
Ooi et al., "Prospective Real-Time Correction for Arbitrary Head Motion Using Active Markers", Magnetic Resonance in Medicine (Apr. 15, 2009) 62(4): 943-54.
Orchard et al., "MRI Reconstruction using real-time motion tracking: A simulation study", Signals, Systems and Computers, 42nd Annual Conference IEEE, Piscataway, NJ, USA (Oct. 26, 2008).
Park, Frank C. and Martin, Bryan J., "Robot Sensor Calibration: Solving AX-XB on the Euclidean Group", IEEE Transaction on Robotics and Automation, 10(5): 717-721 (Oct. 1994).
PCT Search Report from the International Searching Authority, dated Feburary 28, 2013, in 16 pages, regarding International Application No. PCT/US2012/052349.
Qin et al., "Prospective Head-Movement Correction for High-Resolution MRI Using an In-Bore Optical Tracking System", Magnetic Resonance in Medicine (Apr. 13, 2009) 62: 924-934.
Schulz et al., "First Embedded In-Bore System for Fast Optical Prospective Head Motion-Correction in MRI", Proceedings of the 28th Annual Scientific Meeting of the ESMRMB (Oct. 8, 2011) 369.
Shiu et al., "Calibration of Wrist-Mounted Robotic Sensors by Solving Homogeneous Transform Equations of the Form AX=XB", IEEE Transactions on Robotics and Automation, 5(1): 16-29 (Feb. 1989).

(56) References Cited

OTHER PUBLICATIONS

Tremblay et al., "Retrospective Coregistration of Functional Magnetic Resonance Imaging Data using External monitoring", Magnetic Resonance in Medicine 53:141-149 (2005).
Tsai et al., "A New Technique for Fully Autonomous and Efficient 3D Robotics Hand/Eye Calibration", IEEE Transaction on Robotics and Automation, 5(3): 345-358 (Jun. 1989).
Wang, Ching-Cheng, "Extrinsic Calibration of a Vision Sensor Mounted on a Robot", IEEE Transactions on Robotics and Automation, 8(2):161-175 (Apr. 1992).
Ward et al., "Prospective Multiaxial Motion Correction for fMRI", Magnetic Resonance in Medicine 43:459-469 (2000).
Welch at al., "Spherical Navigator Echoes for Full 3D Rigid Body Motion Measurement in MRI", Magnetic Resonance in Medicine 47:32-41 (2002).
Zaitsev, M., et al., "Prospective Real-Time Slice-by-Slice 3D Motion Correction for EPI Using an External Optical Motion Tracking System", Proc.Intl.Soc.Mag.Reson.Med.11:517(2004).
Zeitsev et al., "Magnetic resonance imaging of freely moving objects: Prospective real-time motion correction using an external optical motion tracking system", NeuroImage 31 (Jan. 29, 2006) 1038-1050.

\* cited by examiner

SYSTEMS, DEVICES, AND METHODS FOR TRACKING AND COMPENSATING FOR PATIENT MOTION DURING A MEDICAL IMAGING SCAN

CROSS-REFERENCE TO RELATED APPLICATIONS

The present application claims the benefit under 35 U.S.C. §119(e) of U.S. Provisional Application No. 62/258,915, filed Nov. 23, 2015, and entitled "SENSORS FOR MOTION COMPENSATION IN MEDICAL IMAGING SCANS," U.S. Provisional Application No. 62/332,402, filed May 5, 2016, and entitled "SYSTEMS, DEVICES, AND METHODS FOR TRACKING AND COMPENSATING FOR PATIENT MOTION DURING A MEDICAL IMAGING SCAN, and U.S. Provisional Application No. 62/333,023, filed May 6, 2016, and entitled "SYSTEMS, DEVICES, AND METHODS FOR TRACKING AND COMPENSATING FOR PATIENT MOTION DURING A MEDICAL IMAGING SCAN." The foregoing applications are hereby incorporated herein by reference in their entirety under 37 C.F.R. §1.57.

BACKGROUND

The disclosure relates generally to the field of motion tracking, and more specifically to systems, devices, and methods for tracking and compensating for patient motion during a medical imaging scan.

There are various modalities for performing medical imaging of patients. For example, magnetic resonance imaging (MRI) is a medical imaging technique used in radiology to visualize internal structures of the body in detail. An MRI scanner is a device in which the patient or a portion of the patient's body is positioned within a powerful magnet where a magnetic field is used to align the magnetization of some atomic nuclei (usually hydrogen nuclei—protons) and radio frequency magnetic fields are applied to systematically alter the alignment of this magnetization. This causes the nuclei to produce a rotating magnetic field detectable by the scanner and this information is recorded to construct an image of the scanned region of the body. These scans typically take several minutes (up to about 40 minutes in some scanners) and in some devices any significant movement can ruin the images and require the scan to be repeated.

Additionally, there are various radiation therapies, proton therapies, and other therapies that can be applied to patients. For example, radiation therapy can be applied to a targeted tissue region. In some systems, radiation therapy can be dynamically applied in response to patient movements. However, in many such systems, the tracking of patient movements does not have a high degree of accuracy. Accordingly, the use of such systems can result in the application of radiation therapy to non-targeted tissue regions, thereby unintentionally harming healthy tissue while intentionally affecting diseased tissue. The foregoing is also true for proton therapies and other therapies.

SUMMARY

An accurate and reliable method of determining the dynamic position and orientation of a patient's head or other body portion during MRI scanning or therapeutic procedures is a requirement in any attempt to compensate for subject motion during such procedures. Toward this end, disclosed herein are systems, devices, and methods for tracking and compensating for patient motion during a medical imaging scan and/or therapeutic procedures, such as during a magnetic resonance imaging (MRI) scan and/or radiation therapy.

In some embodiments, a motion detection and correction system and/or device for tracking and correcting or compensating for patient motion during a medical imaging scan can be adapted to be integrated into a medical imaging scanner, such as an MRI scanner, or be adapted to retrofit a pre-existing medical imaging scanner. In certain embodiments, the motion detection system and/or device can comprise one or more carriers and a motion correction device housing, which can further comprise one or more camera modules or detectors and a power unit. In further embodiments, motion data of a subject collected and detected by a motion detection and correction device can be further analyzed by an image processing unit of the motion tracking and/or correction system.

In some embodiments, a motion correction device for a medical imaging scanner comprises: a device housing, wherein the device housing comprises an arcuate surface, and wherein the device housing comprises: one or more optics openings on the arcuate surface; one or more camera modules or detectors configured to detect motion of a subject of the medical imaging scanner through the one or more optics openings, wherein each of the one or more camera modules or detectors further comprises: a camera module or detector housing; and a sensor module placed within the camera module or detector housing, wherein the sensor module is configured to be removably coupled to the camera module or detector housing; a power unit configured to regulate power to the one or more camera module or detector; and one or more wires configured to connect the one or more camera module or detectors to the power unit, wherein the device housing is configured to be removably coupled to a top inner surface of a bore of the medical imaging scanner.

In certain embodiments, the device is configured to be removably coupled to a plurality of medical imaging scanners, wherein each of the plurality of medical imaging scanners comprises a bore of a different size. In some embodiments, the device is configured to detect motion of the subject of the medical imaging scanner and transmit the detected motion to a motion tracking system for processing the detected motion. In certain embodiments, the device is configured to be removed and reattached to the medical imaging scanner without losing alignment of the one or more camera modules or detectors.

In some embodiments, the one or more optics openings comprises indium tin oxide coated glass. In certain embodiments, the one or more optics openings protrude from the arcuate surface at an angle. In some embodiments, the device housing further comprises one or more radiofrequency chokes. In certain embodiments, the device housing further comprises one or more mounting clips, wherein the one or more mounting clips are configured to be removably attached to a mounting bracket, wherein the mounting bracket is attached to the top inner surface of the bore. In some embodiments, the camera module or detector housing is flash plated with a material configured to delay oxidation.

In certain embodiments, the camera module or detector housing comprises a top cover and a bottom cover, wherein the top cover comprises one or more non-parallel walls to eliminate standing waves. In some embodiments, the top cover comprises copper and/or nickel. In certain embodiments, an optics module is mechanically fixated to a sensor module within the camera module or detector housing. In some embodiments, the optics module comprises an optics and a sensor. In some embodiments, the optics module further comprises one or more mirrors. In certain embodiments, the optics is placed within the optics module in a longitudinal direction of the optics module. In some embodiments, the sensor module includes an imaging sensor, sensor electronics, a processing unit, and one or more light sources for illumination.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

The foregoing and other features, aspects, and advantages of the present inventions are described in detail below with reference to the drawings of various embodiments, which are intended to illustrate and not to limit the inventions. The drawings comprise the following figures in which.

DETAILED DESCRIPTION

Figure 1:
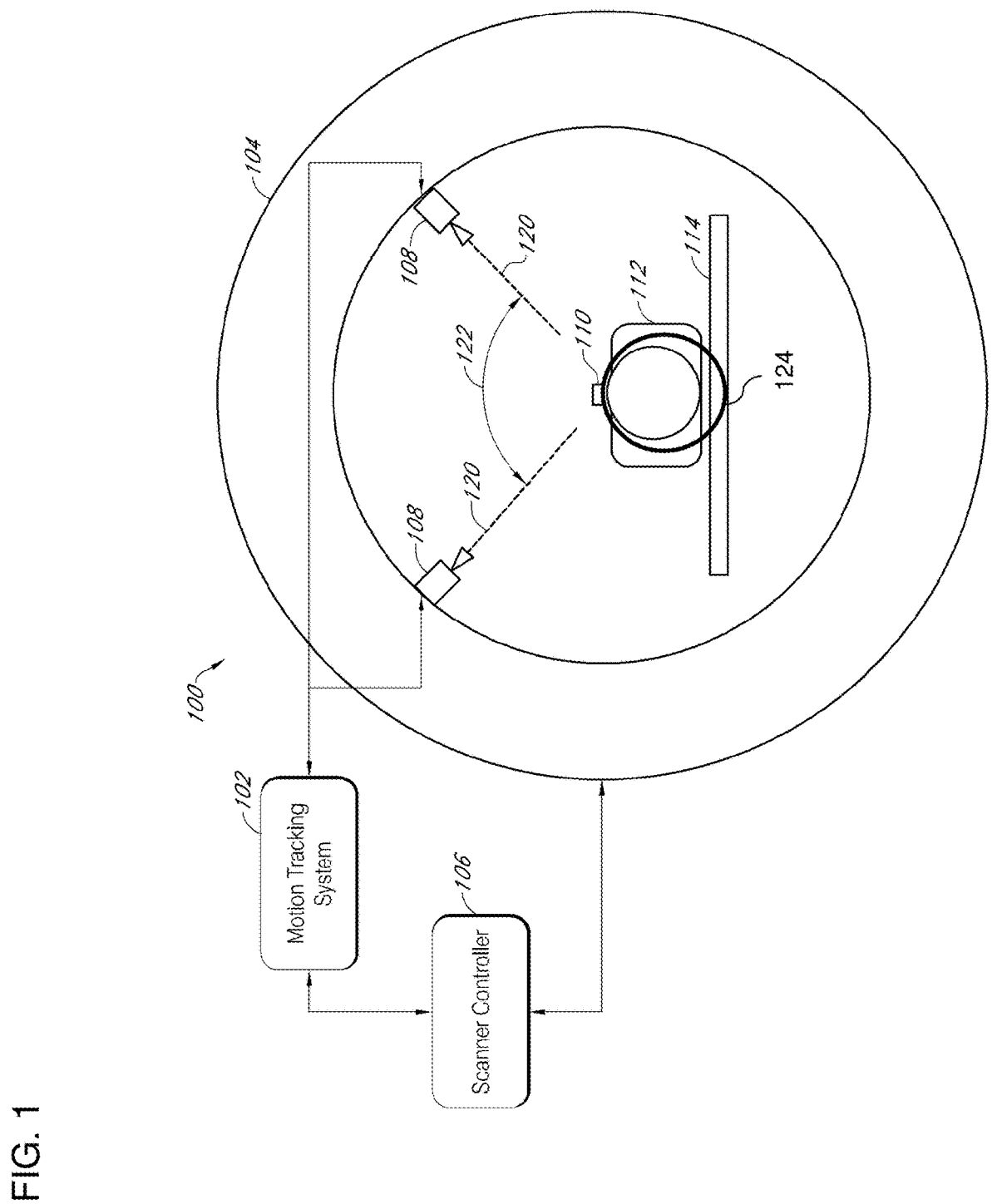
FIG. 1 is a schematic diagram illustrating a front view of an embodiment of a medical imaging scanner or therapeutic device as a part of a motion tracking and/or correction system.

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

With the use of diagnostic technologies and therapeutic technologies, it can be advantageous to track for patient movement with a high degree of accuracy. Such high accuracy tracking can improve the imaging quality obtained and produced by diagnostic equipment, such as imaging technologies. Further, the use of high accuracy patient movement tracking technology can improve the application of patient therapies, such as radiation treatment, proton treatment, and the like. By accounting for patient movement with a high degree of accuracy, therapeutic technologies can apply therapies only to the targeted tissue and avoid healthy surrounding tissue.

U.S. Pat. No. 8,121,361, issued Feb. 21, 2012, entitled "MOTION TRACKING SYSTEM FOR REAL TIME ADAPTIVE IMAGING AND SPECTROSCOPY," describes a system that adaptively compensates for subject motion, and the disclosure therein is hereby incorporated herein by reference. U.S. Pat. No. 9,305,365, issued Apr. 5, 2016, and entitled "SYSTEMS, DEVICES, AND METHODS FOR TRACKING MOVING TARGETS," U.S. patent application Ser. No. 14/762,583, filed Jul. 22, 2015, and entitled "MOTION TRACKING SYSTEM FOR REAL TIME ADAPTIVE MOTION COMPENSATION IN BIOMEDICAL IMAGING," U.S. patent application Ser. No. 13/594,563, filed Aug. 24, 2012, and entitled "METHODS, SYSTEMS, AND DEVICES FOR INTRA-SCAN MOTION CORRECTION," U.S. patent application Ser. No. 14/806,521, filed Jul. 22, 2015, and entitled "SYSTEMS, DEVICES, AND METHODS FOR TRACKING AND COMPENSATING FOR PATIENT MOTION DURING A MEDICAL IMAGING SCAN," U.S. patent application Ser. No. 14/762,581, filed Jul. 22, 2015, and entitled "SYSTEMS, DEVICES, AND METHODS FOR TRACKING AND COMPENSATING FOR PATIENT MOTION DURING A MEDICAL IMAGING SCAN," and U.S. patent application Ser. No. 14/666,049, filed Mar. 23, 2015, and entitled "SYSTEMS, METHODS, AND DEVICES FOR REMOVING PROSPECTIVE MOTION CORRECTION FROM MEDICAL IMAGING SCANS," are also incorporated herein by reference in their entirety.

The embodiments disclosed herein relate to a patient motion tracking and/or correction systems, devices, and methods. In some embodiments, motion tracking and/or correction systems, devices, and methods can be adapted to track and/or correct motion of a subject of a medical imaging scan as to produce high quality medical image scans despite movement by the subject. Similarly, in certain embodiments, motion tracking and/or correction systems, devices, and methods can be adapted to track and/or correct motion of a subject of a therapeutic procedure as to better apply therapy to a targeted area of the body. The embodiments disclosed herein can track patient movement with translation accuracies of about 0.1 mm and angle accuracies of about 0.1 degrees in order to obtain high quality medical image scans correcting for subject movement and/or better apply radiation therapy, proton therapy, or any other therapy to the targeted tissue or area of the body.

More specifically, as disclosed herein, the system can be adapted to track patient movement in order to feed such movement data to an MRI scanner such that the MRI scanner can adjust the focus and position of the scanner in order to produce a clear MRI image of the patient. Further, the system can be adapted to connect to therapeutic technologies. For example, the system can be adapted to track patient movement in order to direct a therapeutic radiation beam at a diseased tissue region while avoiding surrounding healthy tissue.

There are various technologies for therapeutic radiation and other therapeutics. For example, it can be advantageous in radiation therapy, proton therapy, or other therapies to dynamically apply the radiation to a targeted area in order to account for patient movement. Patient movement can include respiration, twitches or any other voluntary or involuntary movements of the patient. By dynamically and automatically tracking patient movement, radiation therapy, proton therapy, and any other kind of therapy can be applied in a more targeted way, thereby allowing surrounding healthy tissue to be avoided and/or unharmed.

Further, the patient movement tracking system, as disclosed herein, can be utilized to track periodic involuntary movement of the patient, such as breathing. By tracking the periodic patient movement with a high degree of accuracy, the system can be adapted to apply a radiation therapy, a proton therapy, or the like during strategic moments when the target tissue is in a certain position while the patient's involuntary movements continue. Additionally, the system can be adapted to track not only normal breathing movement of the patient, but also the system can be adapted to track irregular movement of the patient caused by patient activity or based on diseased tissue of the patient. For example, when a patient is running, the ribs of the patient have a larger egression that the system can track in order to continuously identify a target tissue area. In another example, the patient may be suffering from Chronic Obstructive Pulmonary Disease (COPD) or other breathing disorder or diagrammatic issues. For example, the patient could be suffering from theurofusion, which is water outside the lung that prevents the patient from breathing or a tumor is irritating a lung region thereby preventing normal breathing. The system can be adapted to track such irregular patient movements due to such conditions.

In certain embodiments, motion tracking and/or correction systems, devices, and methods can be integrated into one or more medical imaging scanners and/or therapeutic systems. In other embodiments, motion tracking and/or correction systems, devices, and methods can be adapted to be retrofitted into one or more pre-existing medical imaging scanners and/or therapeutic systems.

General Overview of Motion Tracking and/or Correction System

As discussed above, motion tracking and/or correction system, device, and/or methods described herein can be used in conjunction with a medical imaging scanner and/or a therapeutic system. FIG. 1 is a schematic diagram illustrating a front view of an embodiment of a medical imaging scanner or therapeutic device as a part of a motion tracking and/or correction system.

The motion tracking and/or correction system 100, as illustrated in FIG. 1, can be used to, for example, track the motion of a patient undergoing a medical imaging procedure to enable a medical imaging scanner to adjust or otherwise compensate for that motion, to reduce, or eliminate motion artifacts in the resulting medical images. The motion tracking and/or correction system 100 illustrated in FIG. 1 comprises a motion tracking system 102, a medical imaging scanner or therapeutic device 104, 124, a scanner controller 106, one or more camera modules or detectors 108, and an optical marker or target 110. In this embodiment, the optical marker 110 is shown attached to a patient 112 positioned on a table 114 of the medical imaging scanner 104. The scanner 104 can be, for example, a magnetic resonance imaging scanner. The device 124 can be, for example, a magnetic resonance head coil. The optical marker 110 can be configured as further described below.

In the illustrated embodiment, the optical marker 110 is configured to be viewable by each of the two camera modules or detectors 108. The camera modules or detectors 108 can be, for example, digital cameras capable of acquiring images of the optical marker 110 and transmitting those images to the motion tracking system 102. In this embodiment, each of the camera modules or detectors 108 is configured to view the optical marker 110 from along a different line of sight. This can be helpful, for example, to enable the motion tracking system 102 to analyze two dimensional images of the optical marker 110 from different vantage points to help in locating the optical marker 110 to estimate patient motion or pose. In the illustrated embodiment, the camera modules or detectors 108 each are configured to view the optical marker 110 along a line of sight 120 separated from each other by an angle 122. In this embodiment, the angle 122 is approximately 90 degrees. Other angles may be used, such as 30 degrees, 45 degrees, 60 degrees, 70 degrees, etc. In some embodiments, 90 degrees is an optimal angle to enable maximum differentiation of in plane and out of plane motion of the optical marker 110, as further described below. For example, if the optical marker 110 moves in a direction that is directly along the line of sight of one detector, that detector may have a harder time distinguishing motion of the optical marker 110 than the other detector. On the other hand, the other detector may relatively easily detect the motion of the optical marker 110, as the motion is perpendicular to that detector's line of sight.

In some embodiments, the angle 122 may be referred to as a scissor angle. In the embodiment illustrated in FIG. 1, the scissor angle is the angle at which the camera modules or detectors 108 are directly viewing the marker 110. However, in other embodiments, the scissor angle may be a virtual angle, as the lines of sight from the camera modules or detectors 108 to the marker 110 may be redirected by mirrors and/or other means, such as beam splitters, prisms, fiber optics, and/or the like. In that case, the scissor angle is the apparent angle at which the camera modules or detectors 108 are viewing the marker 110.

Mirrors or other devices used to redirect a line of sight can have both advantages and disadvantages. For example, disadvantages of mirrors include that they could potentially vibrate, potentially introducing error into the object orientation determination process. As another example, the further away a mirror is from a camera modules or detector, generally the larger the mirror needs to be to enable an equivalent range of vision. Accordingly, it can be advantageous to position a mirror relatively close to a camera modules or detector to enable the mirror to be relatively small. One advantage of using mirrors or other sight line redirection methods is that a virtual scissor angle can be configured to be closer to an optimal scissor angle of 90°, even when a particular medical imaging scanner configuration may not allow for camera modules or detectors that are positioned to directly view a marker using a 90° scissor angle. Further, some mirrors are not conductive, which can be advantageous in magnetic resonance imaging, because nonconductive mirrors will not introduce artifacts into MRI images. A digital camera, on the other hand, may include conductive components and/or a wire leading to the camera modules or detector may include conductive components. When a digital camera and/or its wire are within the medical imaging envelope, they may introduce artifacts into MRI images.

The embodiment of a motion tracking and/or correction system 100 illustrated in FIG. 1 is not shown to scale, but is rather show at a scale that helps facilitate illustration of the system. Other figures are also not shown to scale. Additionally, most embodiments illustrated in these figures and described in this specification comprise a motion tracking and/or correction system operating in real time or substantially in real time to correct a scanner for motion of a patient or object. However, in other embodiments, a motion tracking and/or correction system can be configured to operate by processing images using post-processing after they have been created by a scanner to remove any motion artifacts.

As discussed above, in some embodiments, a motion tracking and/or correction system can be integrated into a medical imaging scanner or therapeutic device or adapted to be retrofitted to a pre-produced and/or pre-existing medical imaging scanner or therapeutic device. More specifically, the one or more camera modules or detectors 108 can be integrated in a medical imaging scanner or therapeutic device in some embodiments, whereas the one or more camera modules or detectors 108 can be retrofitted to a medical imaging scanner or therapeutic device in other embodiments.

In general, MRI or other medical imaging scanners can be of different sizes. The embodiments of integrated and retrofitted motion tracking and/or correction systems disclosed herein can be applied to MRI scanners and/or other medical imaging scanners of various sizes, including MRI scanners with a diameter of about 70 cm and/or with a diameter of about 60 cm. Moreover, an integrated and/or retrofit motion tracking and/or correction system can be adapted to fit a medical imaging scanner or MRI scanner with a diameter of about 40 cm, 50 cm, 60 cm, 70 cm, 80 cm, 90 cm, 100 cm, 110 cm, 120 cm, 130 cm, 140 cm, 150 cm or between a range defined by any two of the values mentioned above. In certain embodiments, an MRI scanner, other medical imaging scanner, and/or therapeutic device can have a diameter of about 694.5 mm, about 685.5 mm, about 684.52 mm, about 694.24 mm, about 597 mm, about 595 mm, and/or about 596.34 mm.

Further, in some embodiments, a head coil 124 can be adapted to be used in conjunction with a medical imaging scanner. Head coils 124 of different configurations and/or sizes may be used. For example, in some embodiments, a head/neck 64-channel configuration coil and/or a head/neck 20-channel configuration coil may be used in conjunction with a medical imaging scanner and/or a motion tracking and/or correction system and/or device. In other embodiments, head/neck (HN) configurations of 2-, 4-, 6-, 8-, 10-, 12-, 14-, 16-, 18-, 22-, 24-, 26-28-, 30-, 32-, 34-, 36-, 38, 40-, 42-, 44-, 46-, 48-, 50-, 52-, 54-, 56-, 58-, 60-, 62-channels or configurations of a number of channels within a range defined by any of the two aforementioned values can be used. The above-identified number of channels and/or head/neck coil configurations can be related to the resolution of the coil.

Furthermore, in certain embodiments, one or more markers 110 can be adapted to be used in conjunction with a motion tracking and/or correction system and/or device. As shown in FIG. 1, in certain embodiments, one or more markers 110 can be adapted to be placed on the patient and/or portion of the body of the subject of interest. In some embodiments, the one or more markers 110 can be of different sizes and/or configurations. For example, in a certain embodiment, a marker with a size of 14×14 mm can be used.

A retrofit and/or integrated motion tracking and/or correction system can comprise one or more camera modules or detectors 108. For example, a retrofit and/or integrated motion tracking and/or correction system can comprise one, two, three, four, five, six, seven, eight, nine, or ten camera modules or detectors 108. In certain embodiments, all camera modules or detectors 108 installed can be adapted to detect, track, and/or collect motion data of the subject. In some embodiments, a subset of the total number of camera modules or detectors 108 installed can be configured to detect, track, and/or collect motion data of the subject depending on the line of sight of each camera modules or detector 108 at any given point in time. For example, in some embodiments, one of a total of two camera modules or detectors 108, one of a total of three camera modules or detectors 108, two of a total of three camera modules or detectors 108, one of a total of four camera modules or detectors 108, two of a total of four camera modules or detectors 108, three of a total of four camera modules or detectors 108, one of a total of five camera modules or detectors 108, two of a total of five camera modules or detectors 108, three of a total of five camera modules or detectors 108, four of a total of five camera modules or detectors 108, one of a total of six camera modules or detectors 108, two of a total of six camera modules or detectors 108, three of a total of six camera modules or detectors 108, four of a total of six camera modules or detectors 108, and/or five of a total of six camera modules or detectors 108 can be configured to detect, track, and/or collect motion data of the subject.

In certain embodiments, a motion tracking and/or correction system, whether integrated or retrofit, comprises dynamic switching capabilities such that the system is configured to identify which of the one or more camera modules or detectors 108 are actually in a position to view the target and utilize only those camera modules or detectors 108 to track, maintain tracking, and/or continuously track the target. Further, in some embodiments, the specific angles of each camera modules or detector 108 can be optimized for optimal collection of motion data of the subject. For example, a motion tracking and/or correction system, whether integrated or retrofit, can be configured to determine an optimal position of one or more camera modules or detectors 108 for viewing the subject and alter the position or angle or direction of the camera modules or detector 108 accordingly.

Viewing and/or Monitoring Subject

In some embodiments, a retrofit or integrated motion tracking and/or correction system can be configured to capture and/or detect the position and movement of a subject and transfer such data in real-time, near real-time, or substantially thereof to one or more computing systems to allow a user to view and/or monitor the subject. In certain embodiments, one or more computing systems can further be adapted to receive data collected by the retrofit or integrated motion tracking and/or correction system to generate one or more images and/or video feed of the subject viewable by a user in real-time, near real-time, or substantially thereof. For example, in some embodiments, the computing device can comprise one or more displays adapted to visually display the current position and/or motion of the subject to a user, such that a user can monitor the subject.

In certain embodiments, one or more camera modules or detectors 108 of a retrofit or integrated motion tracking and/or correction system can be adapted to capture and/or detect the position and movement of a subject, which can further be visually displayed to a user. For example, in some embodiments, a retrofit or integrated motion tracking and/or correction system can comprise a plurality of camera modules or detectors 108 configured to collect data. One or more computing devices and/or an image processing module of the retrofit or integrated motion tracking and/or correction system can be adapted to generate an image, video, composite image, and/or composite video of a subject, based on the collected data, in real-time, near real-time, or substantially thereof. In some embodiments, one or more computing devices and/or an image processing module of the retrofit or integrated motion tracking and/or correction system and/or software thereof can be configured to generate a composite view of a subject after virtually removing the head coil 124 from the displayed view to a healthcare provider to provide an unobstructed view of the subject without the head coil. For viewing other body portions of the subject other than the head, virtual removal of the head coil 124 may not be required.

In some embodiments, the same one or more camera modules or detectors 108 used for tracking and/or detecting motion data of a subject are used to collect data for generating a visual display of the subject. In other embodiments, one or more additional camera modules or detectors different from camera modules or detectors 108 used for tracking and/or detecting motion data of a subject are used to collect data for generating a visual display of the subject. For example, in certain embodiments, the one or more camera modules or detectors used to collect data for generating a visual display of the subject can comprise a larger field of view than the camera modules or detectors 108 used to detect and/or track subject movement.

In certain embodiments, the one or more camera modules or detectors 108 used to collect data for generating a visual display of the subject can be turned to one or more different light spectrums, for example visible light, infrared, or near infrared. For example, in certain embodiments, the one or more camera modules or detector 108 can be configured to collect data to produce a night vision-type display of the subject as to allow a user to view the subject even in a dark setting. In some embodiments, the one or more camera modules or detectors 108 can comprise an adjustable field of view, and can, for example, go narrower to view a marker or go wider to view the subject.

In some embodiments, the one or more camera modules or detectors 108 can be configured to view the subject with or without any subject motion. For example, in certain embodiments, the one or more detectors 108 can be adapted to collect data to generate a visual display of a subject even when the subject is not moving, as to allow a user to check on a subject. In other words, in certain embodiments, subject or patient viewing can be active even when motion tracking is not active.

In some embodiments, a retrofit or integrated motion tracking and/or correction system is adapted to automatically determine which of the one or more detectors 108 or camera/detector modules to utilize to view the patient, based on a detected pose and/or position of the subject. For example, in certain embodiments, if a subject turns left, the system can be configured to automatically collect data using one or more detectors or cameras 108 located on the left side of a medical imaging scanner in order to generate a visual display of the subject and/or collect motion tracking data. Similarly, in some embodiments, if a subject subsequently turns right, the system can be configured to automatically collect data using one or more camera modules or detectors 108 located on the right side of the medical imaging scanner in order to generate a visual display of the subject and/or collect motion tracking data.

Integrated Motion Tracking and/or Correction System

Figure 2:
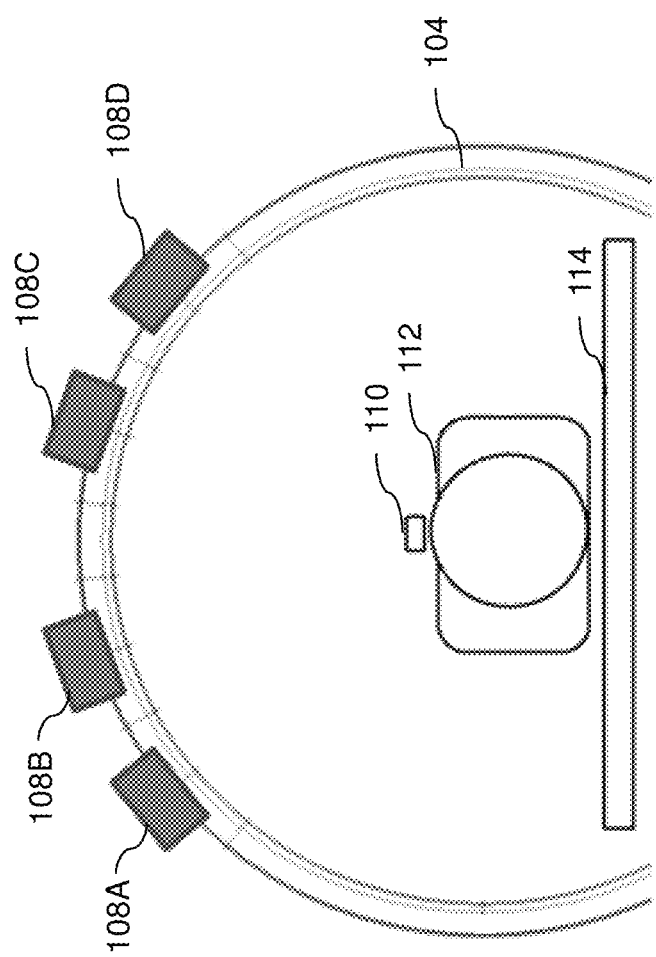
FIG. 2 is a schematic diagram illustrating a front view of an embodiment of an integrated motion tracking and/or correction system.

FIG. 2 is a schematic diagram illustrating a front view of an embodiment of an integrated motion tracking and/or correction system. As illustrated, in some embodiments, one or more camera modules or detectors 108 of a motion tracking and/or correction system and/or device can be integrated to the bore 104 of a medical imaging scanner or therapeutic device. In the illustrated embodiment, the integrated motion tracking and/or correction system comprises four camera modules or detectors 108A, 108B, 108C, 108D integrated to the bore 104 of the medical imaging scanner or therapeutic device. The one or more detectors 108 can be integrated to the bore 104 of the medical imaging scanner or therapeutic device by fixating or anchoring the one or more detectors 108 to the bore 104 or exterior surface thereof. It can be advantageous to attach one or more detectors 108 of a motion tracking and/or correction system and/or device to the exterior surface of the bore of a medical imaging scanner or therapeutic device in order to maximize space inside the bore of the medical imaging scanner or therapeutic device for the patient subject 112.

Figure 3B:
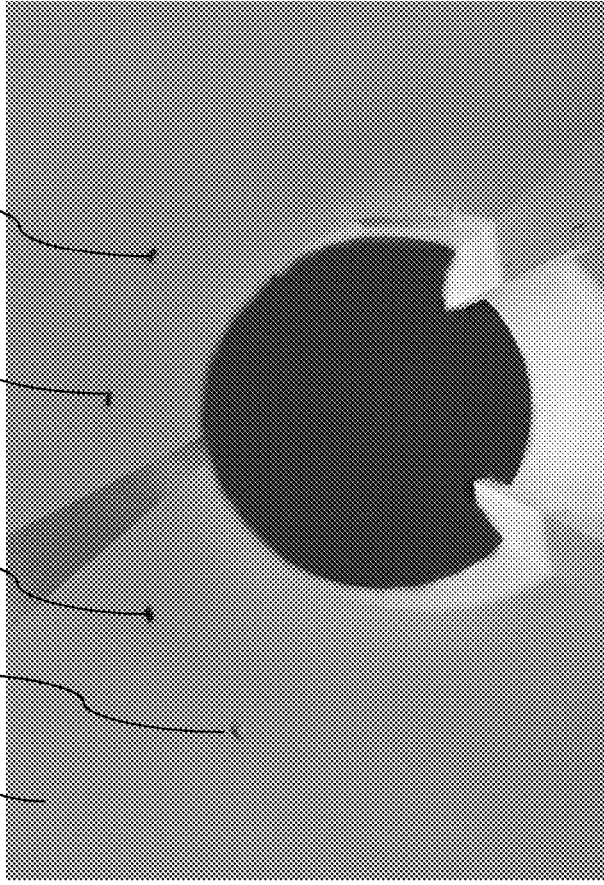
FIG. 3B is a prospective view of an embodiment of the interior of a bore of a medical imaging scanner or therapeutic device that is part of an integrated motion tracking and/or correction system.
Figure 3A:
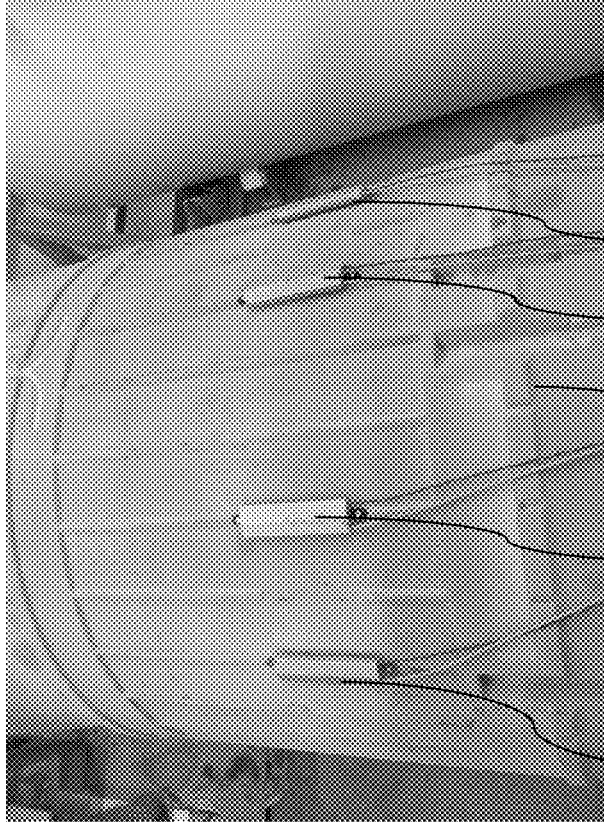
FIG. 3A is a prospective view of an embodiment of the exterior of a bore of a medical imaging scanner or therapeutic device that is part of an integrated motion tracking and/or correction system.

FIG. 3A is a prospective view of an embodiment of the exterior of a bore of a medical imaging scanner or a therapeutic device that is part of an integrated motion tracking and/or correction system. FIG. 3B is a prospective view of an embodiment of the interior of a bore of a medical imaging scanner or a therapeutic device that is part of an integrated motion tracking and/or correction system.

As illustrated in FIGS. 3A and 3B, one or more detectors 108 are integrated into the bore 104 of a medical imaging scanner or therapeutic device, such as an MRI scanner. In the illustrated embodiments, four camera modules or detectors 108A, 108B, 108C, 108D are installed.

In order to attach the camera modules or detectors 108, the bore 104 can comprise one or more through holes 302 for fixating the one or more camera modules or detectors 108 and allowing the same to view the interior of the bore 104. The number of through holes 302 in the bore 104 can be equal to the number of camera modules or detectors. For example, a system with four camera modules or detectors 108A, 108B, 108C, 108D can also have four through holes 302A, 302B, 302C, 303D in the bore. In other embodiments, the bore can comprise more through holes 302 than the number of camera modules or detectors 108 to allow for installation of additional camera modules or detectors 108.

The camera modules or detectors 108 can be fixated or anchored to the outside or exterior surface of the bore 104 in a manner such that the lens or optics of each of the camera module or detector 108 faces inwards towards the interior of the bore 104. By attaching the detectors 108 in a manner such that substantially all of the detectors 108 are located outside of the interior of the bore 104 can allow for maximization of space inside the bore 104 of the medical imaging scanner or MRI scanner or therapeutic device. Accordingly, in some embodiments of the integrated motion tracking and/or correction system, the total interior volume of the bore 104 is not changed due to installation of one or more camera modules or detectors 108 of the motion tracking and/or correction system.

Retrofit Motion Tracking and/or Correction System

However, integrating a motion tracking and/or correction system and/or device may not be possible for some pre-existing medical imaging scanners, for example for one or more compatibility issues. As such, in some embodiments, a retrofit motion tracking and/or correction system can be installed and used in conjunction with a medical imaging scanner, such as an MRI scanner.

Figure 4:
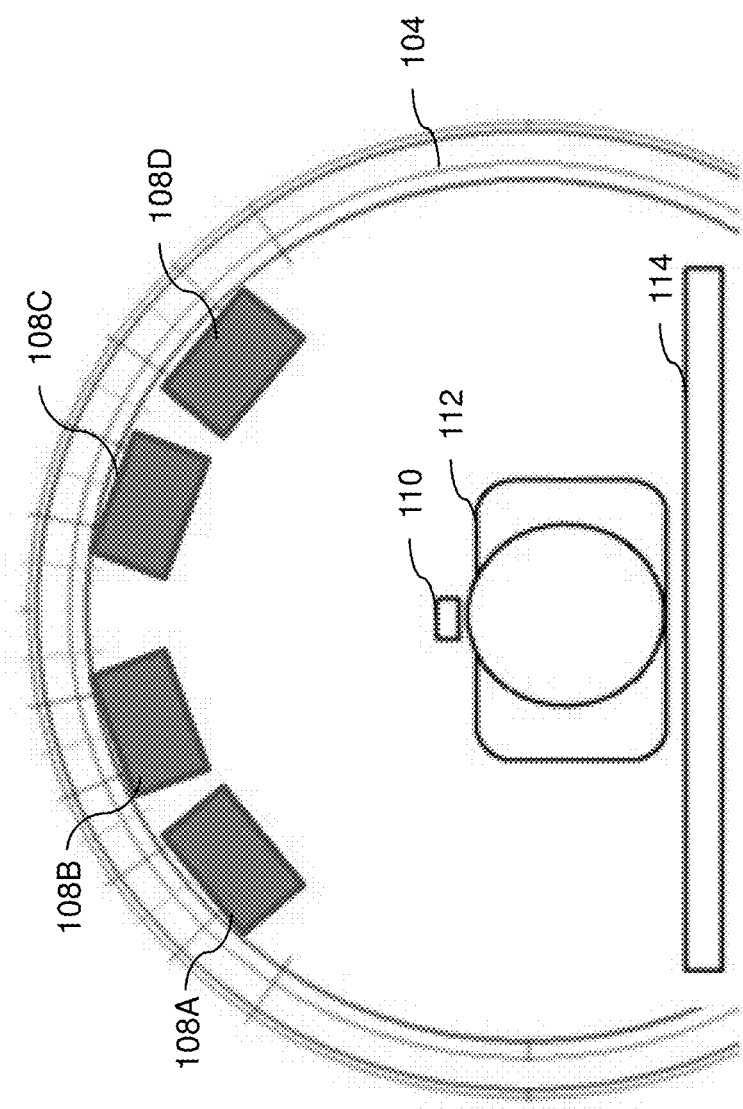
FIG. 4 is a schematic diagram illustrating a front view of an embodiment of a retrofit motion tracking and/or correction system.

FIG. 4 is a schematic diagram illustrating a front view of an embodiment of a retrofit motion tracking and/or correction system. As illustrated in FIG. 4, one or more camera modules or detectors 108 are integrated into the bore 104 of a medical imaging scanner, such as an MRI scanner, or therapeutic device. In the illustrated embodiment, four camera modules or detectors 108A, 108B, 108C, 108D are installed.

Contrary to the integrated system, however, one or more camera modules or detectors 108 can be anchored or fixated on the interior surface of the bore 104 in a retrofit system. Accordingly, the whole camera module or detector 108 can be located inside the bore 104 in a retrofit system. This configuration may decrease the total volume inside the bore 104 when compared to before installation of the one or more camera modules or detectors 108 of the retrofit motion tracking and/or correction system. As such, it can be advantageous in such embodiments to minimize the thickness of the one or more camera modules or detectors 108 and/or the motion correction device in order to maximize space inside the bore 104 of the medical imaging scanner or therapeutic device for the patient subject.

Further, retrofit motion tracking and/or correction systems may not require any through holes as described above in relation to the integrated system to be punctured in the bore 104. As such, while an integrated motion tracking and/or correction system may provide for a more permanent system, a retrofit motion tracking and/or correction system can provide a flexible system in which the motion correction device or one or more components thereof, such as one or more camera modules or detectors 108, may be installed and removed as needed. Further, without the need to puncture any relatively large through holes in the bore 104, as described above in relation to the integrated system, radiofrequency (RF) emissions may be controlled in a similar manner as originally designed for the medical imaging scanner or other therapeutic system to which the motion tracking and/or correction system is coupled to.

Figure 5:
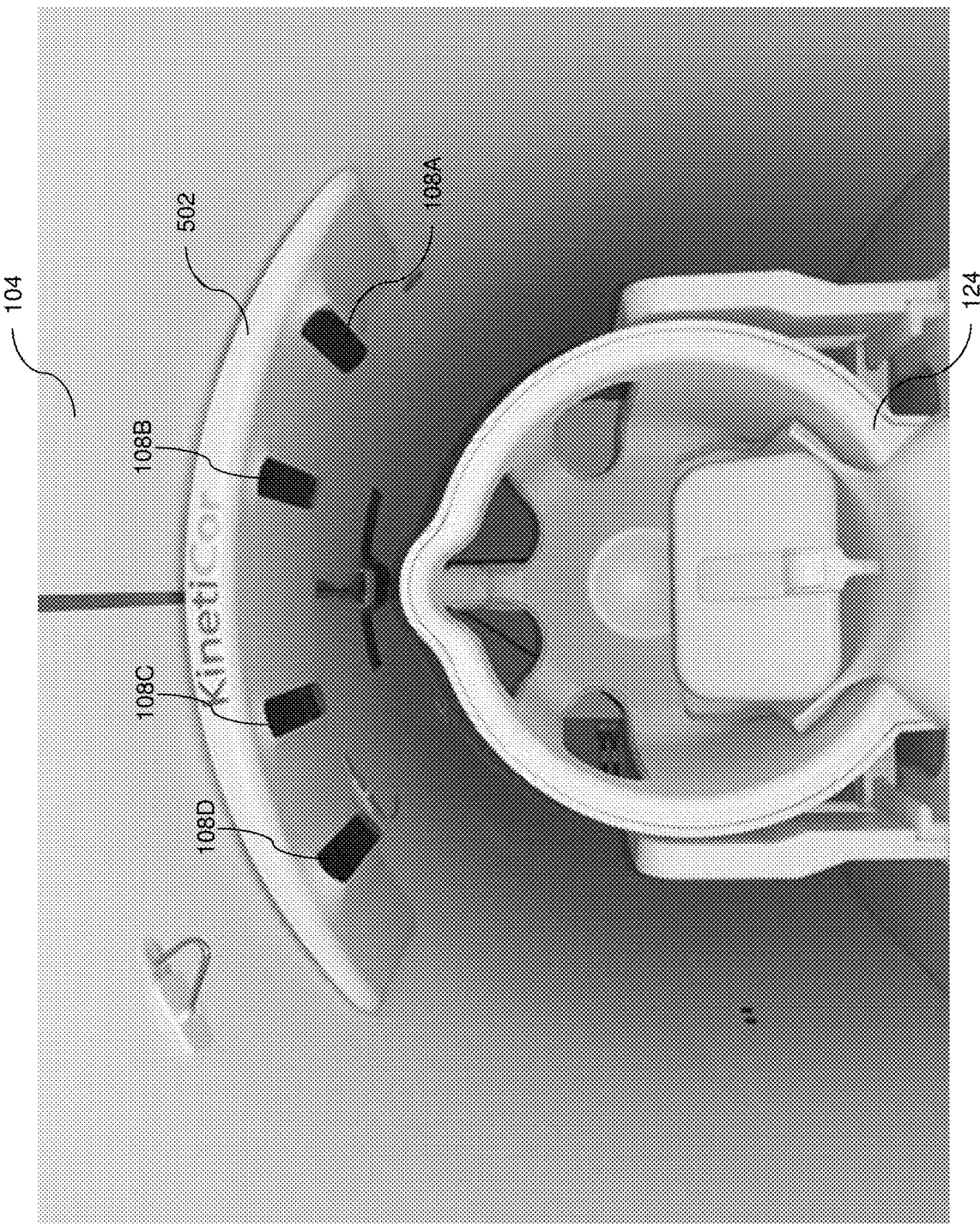
FIG. 5 is a prospective view of an embodiment of the interior of a bore of a medical imaging scanner or therapeutic device that is part of a retrofit motion tracking and/or correction system.
Figure 6:
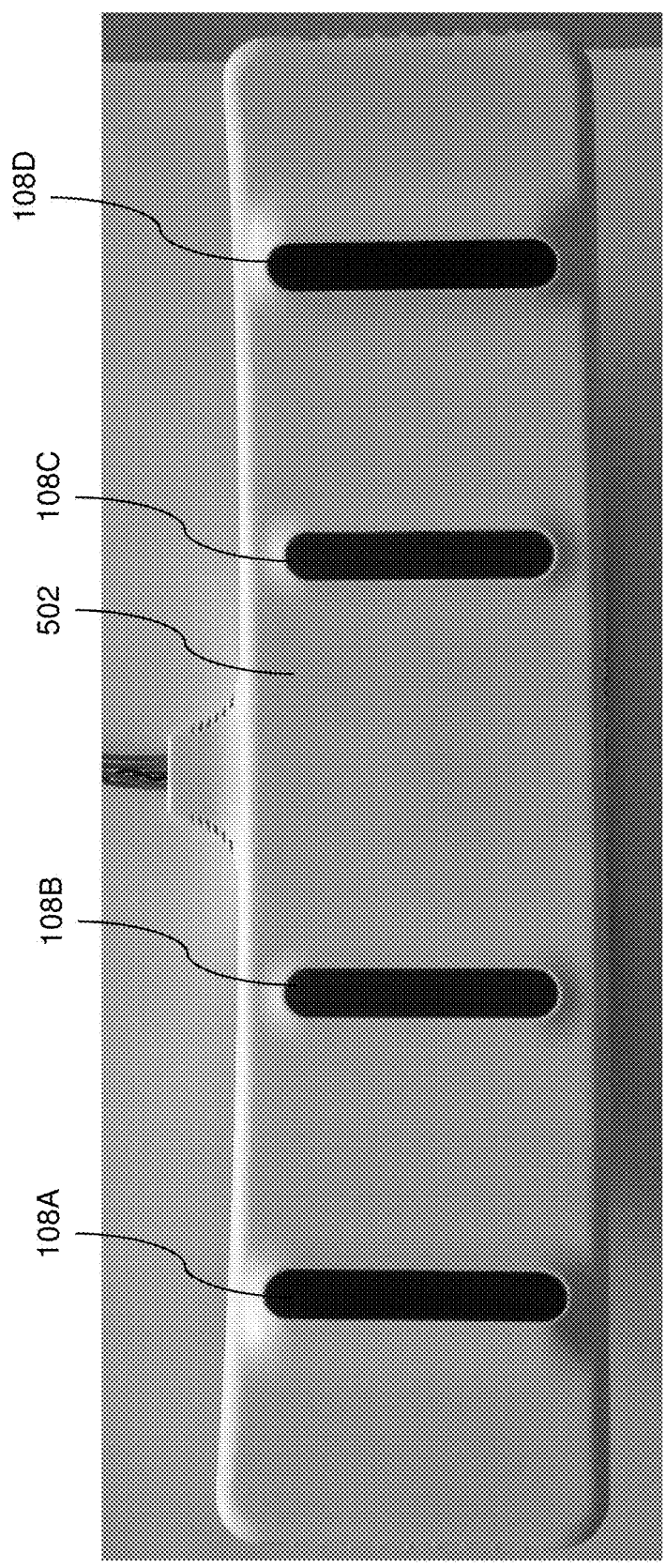
FIG. 6 is a bottom view of an embodiment of a motion correction device housing of a retrofit motion tracking and/or correction system.

FIG. 5 is a prospective view of an embodiment of the interior of a bore of a medical imaging scanner or therapeutic device that is part of a retrofit motion tracking and/or correction system. FIG. 6 is a bottom view of an embodiment of a motion correction device housing of a retrofit motion tracking and/or correction system.

As illustrated, a retrofit motion correction device is attached to the interior surface of the bore 104 at the top of a pre-existing medical imaging scanner and/or MRI scanner. The particular embodiment as illustrated also comprises a head coil 124. However, other embodiments may not comprise a head coil 124 or may comprise a head coil of a different shape, configuration or size.

The motion correction device can comprise a device housing 502. The device housing 502 can comprise a wing or curved shape. It can be advantageous to provide a housing 502 for the motion correction device. For example, when installing each camera module or detector 108 of a retrofit motion detection and/or correction system to a pre-existing medical imaging scanner or therapeutic device separately, one may need to alter or modify the positioning and/or angle of one or more camera modules or detectors 108 of the motion detection and/or correction system for optimal results every time the motion detection and/or correction system reinstalled. However, if these one or more camera or detector modules 108 are pre-formed or pre-configured in a particular position and/or angle within the housing, the motion detection and/or correction system can be installed, removed, and/or reinstalled without losing alignment or without substantially losing alignment of one or more camera or detector modules. As such, with a housing 502, calibration or recalibration process of the one or more camera modules or detectors 108 may not be necessary or may be simplified when attaching or reattaching a motion correction device to a medical imaging scanner, such as an MRI scanner, or therapeutic device. Further, by use of a device housing 502 and/or mounting configuration as described herein, the exact position of the device housing 502 and detector modules 108 thereof relative to the iso-center of the scanner or therapeutic device can be controlled and may eliminate a need for cross calibration between a plurality of detectors and scanner or therapeutic device. Cross calibration can refer to the calibration to ensure identical coordinate systems of the motion detection system and the scanner or therapeutic device.

The device housing 502 can comprise a bottom surface facing towards the subject of interest. The bottom surface can be arcuate. The bottom surface can be substantially parallel to the interior surface of the bore 104. The bottom surface can comprise an arcuate shape that is substantially equal to the arcuate shape or configuration of the interior surface of the bore 104. As such, the interior space within the bore 104 can be maximized.

The device housing 502 can also comprise one or more side portions or surfaces. The one or more side portions or surfaces can be substantially perpendicular to the bottom surface. The one or more side portions or surfaces can also be substantially perpendicular to the interior surface of the bore when the device housing 502 is installed or coupled to the bore 104.

The device housing 502 can comprise one or more optics openings on the bottom surface to allow for the one or more camera modules or detectors 108 to view the subject. The one or more openings can be RF shielded, for example by a dual layer comprising indium tin oxide (ITO) coated glass window and/or wire mesh. Other materials and/or configurations can be used for RF shielding as well. The one or more openings can be uncovered in certain embodiments. The one or more openings can include optical filters to protect the inside device housing 502, and block light emissions originating from inside or outside the scanner bore from affecting the image detection of the detector modules 108. The one or more optics openings can comprise an oblong shape. In other embodiments, the one or more optics openings can be substantially circular, rectangular, triangular, or any other shape. The optics openings can comprise a shape or configuration that is substantially similar or the same with the shape or configuration of a camera module or detector as described herein. In the illustrated embodiment, each of the one or more optics openings comprises two substantially straight sides and two arcuate sides connecting the two substantially straight sides.

In the illustrated embodiment, the device housing 502 comprises four optics openings. In other embodiments, the device housing 502 can comprise one, two, three, four, five, six, seven, eight, nine, or ten optics openings. The number of optics openings can be within a range defined by two of the aforementioned values. In certain embodiments, the number of optics openings can be equal to the number of camera modules or detectors 108 present in the device or system. In other embodiments, the number of optics openings can be greater than the number of camera modules or detectors 108 and can allow for installation of additional camera modules or detectors.

The one or more optics openings can be angled with respect to the bottom surface of the device housing 502. For example, the one or more openings can protrude at an angle from bottom surface of the device housing 502 at about 5°, about 10°, about 15°, about 20°, about 25°, about 30°, about 35°, about 40°, about 45°, about 50°, about 55°, about 60°, about 65°, about 70°, about 75°, about 80°, about 85°, about 90°, and/or within a range defined by two of the aforementioned angles. All of the optics openings can protrude from the bottom surface of the device housing 502 at a substantially equal angle. In certain embodiments, some of the optics openings can protrude from the bottom surface of the device housing 502 at a substantially equal angle while others protrude from the bottom surface at different angles. For example, in the illustrated embodiment, optics openings for top detector modules 108B and 108C can protrude from the bottom surface at a substantially equal angle but in opposite directions or mirror images with respect to a vertical plane drawn at the center of the device housing 502 along a longitudinal axis of the bore 104. Similarly, optics openings for side detector modules 108A and 108D can protrude from the bottom surface at a substantially equal angle but in opposite directions or mirror images with respect to a vertical plane drawn at the center of the device housing 502 along a longitudinal axis of the bore 104. In other embodiments, each of the plurality of optics openings can protrude from the bottom surface at different angles.

The angle of protrusion of the one or more optics openings can be made to optimize viewing by the one or more camera modules or detectors 108. The angle of protrusion of the one or more optics openings can be made to be optimal for viewing for a particular medical imaging scanner, such as an MRI scanner, or therapeutic device according to the shape of the interior of the bore 104. The angle of protrusion of the one or more optics openings can be made to be optimal for viewing for a plurality of medical imaging scanners, such as MRI scanners, or therapeutic devices.

In some embodiments, a single device housing 502, comprising one or more optics openings and one or more camera modules or detectors 108, can be installed or coupled to a medical imaging scanner or therapeutic device. In other embodiments, a plurality of device housings 502, each comprising one or more optics openings and one or more camera modules or detectors 108, can be installed or coupled to a medical imaging scanner or therapeutic device.

In some embodiments, the motion correction device housing 502 and/or a portion thereof is made of a material that does not affect the medical imaging scanner or therapeutic device. For example the motion correction device housing and/or a portion thereof, for example other than the optics openings, can 502 be made from a plastic material that is transparent to medical imaging scanners or therapeutic devices in general and/or to a particular medical imaging scanner, such as an MRI scanner, or therapeutic device. In some embodiments, the motion correction device housing 502 and/or a portion thereof, for example other than the optics openings, comprises ABS plastic.

Mounting Bracket

Figure 7:
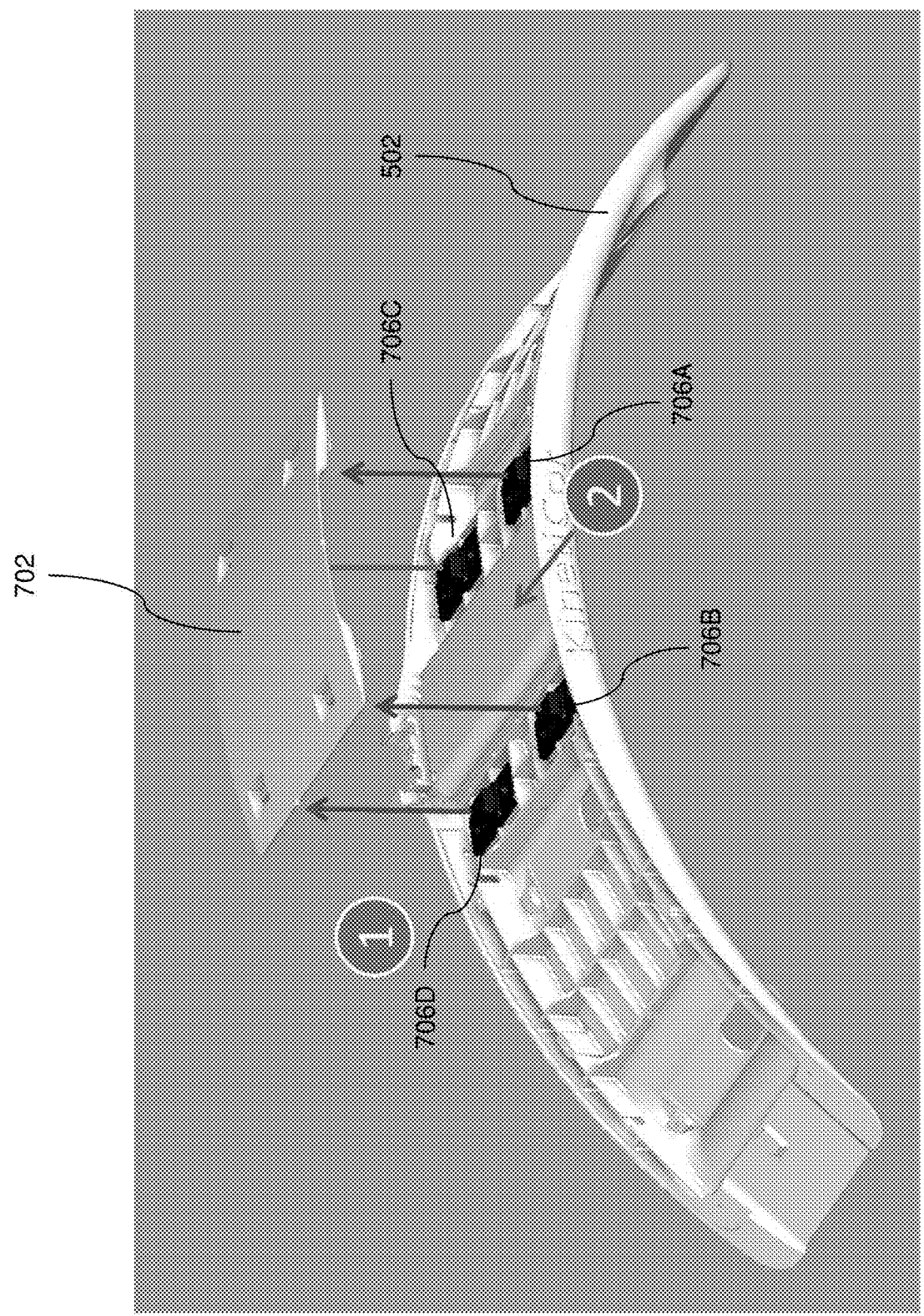
FIG. 7 is a schematic diagram illustrating a prospective view of an embodiment of a mount for a motion correction device housing of a retrofit motion tracking and/or correction system.

As discussed above, the device housing 502 can be attached or coupled to the top of the interior surface of the bore 104. More specifically, the device housing 502 can be attached mechanically using a mounting bracket and/or mounting clips. FIG. 7 is a schematic diagram illustrating a prospective view of an embodiment of a mount for a motion correction device housing of a retrofit motion tracking and/or correction system.

As illustrated, in some embodiments, a retrofit motion detection and/or correction system comprises one or more mounting brackets 702 for attaching a device housing 502 to a medical imaging scanner or therapeutic device. In certain embodiments, one or more mounting brackets 702 can be configured to be attached to the interior surface of the bore 104 of a medical imaging scanner or therapeutic device. For example, one or more mounting brackets 702 can be configured to be attached to the top, left, right, side, bottom, and/or diagonal position inside a bore 104 of a medical imaging scanner or therapeutic device along the interior wall of the bore 104. In some embodiments, one or more mounting brackets 702 can be configured to be attached to the bore 104 via one or more adhesives and/or one or more mechanical configurations.

In some embodiments, one or more mounting brackets 702 can be configured to be semi-permanently or permanently attached to the bore 104 of a medical imaging scanner or therapeutic device, and a motion correction device housing 502 can be configured to attach to the one or more mounting brackets 702. For example, in such embodiments, the motion correction device housing 502 can be configured to be easily attached and/or removed from the mounting bracket 702. In certain embodiments, one or more mounting brackets 702 can be configured to be attached to a device housing 502 via one or more adhesives and/or one or more mechanical configurations. For example, a mounting bracket 702 can be permanently or semi-permanently mounted to the top of an MRI bore 104 and a motion correction device housing 502 can be configured to attach to the mounting bracket 702 via a mechanical locking configuration.

The device housing 502 can comprise one or more mounting clips 706. In the illustrated embodiment, the device housing 502 comprises four mounting clips 706A, 706B, 706C, 706D. Similarly, the mounting bracket 702 can comprise four corresponding mechanical receivers for receiving the four mounting clips 706A, 706B, 706C, 706D. In some embodiments, the device housing 502 can comprise one, two, three, four, five, six, seven, eight, nine, or ten mounting clips 706. The number of mounting clips 706 of a device housing 502 can also be within a range defined by two of the aforementioned values. Similarly, in certain embodiments, the mounting bracket 702 can comprise one, two, three, four, five, six, seven, eight, nine, or ten receivers for receiving mounting clips 706 of the device housing 502. The number of receivers on the mounting bracket 702 for receiving mounting clips 706 of a device housing 502 can also be within a range defined by two of the aforementioned values The mechanical locking procedure for attaching the device housing 502 to the mounting bracket 702 can comprise a single step. For example, an operator may only need to push the device housing 502 in a generally upward direction towards the mounting bracket 702 to attach and fixate the device housing 502 to the mounting bracket 702. In other embodiments, the attachment procedure can be twofold. For example, an operator may first push the device housing 502 in a generally upward direction towards the mounting bracket 702 and then horizontally push or pull the device housing 502 in a longitudinal direction along the bore 104 to attach and fixate the device housing 502 to the mounting bracket 702. In certain embodiments, the procedure for attaching the device housing 502 to a mounting bracket 702 can comprise three or more steps.

Device Components

Figure 8A:
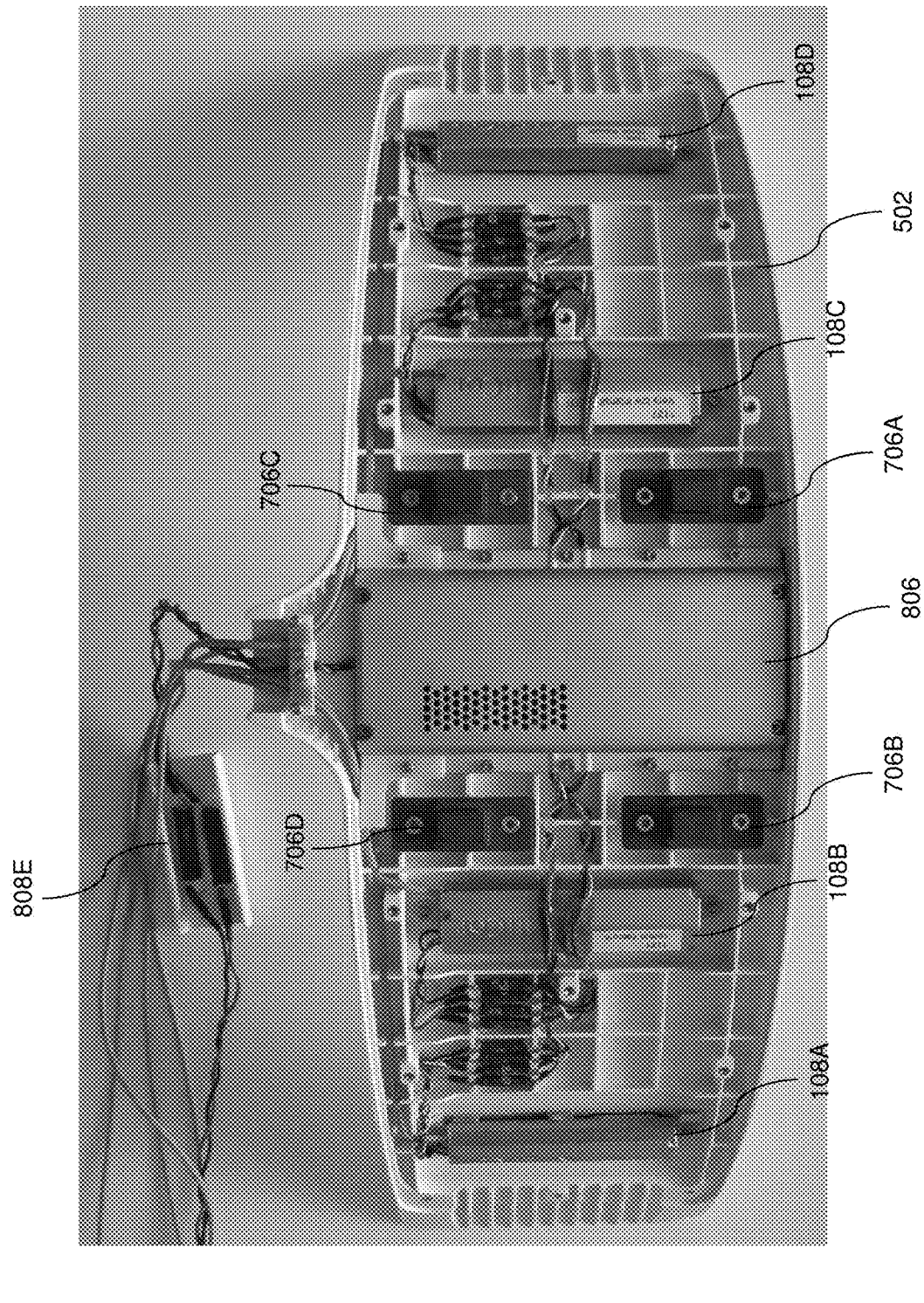
FIGS. 8A and 8B are top views of an embodiment of a motion correction device of a retrofit motion tracking and/or correction system.
Figure 8B:
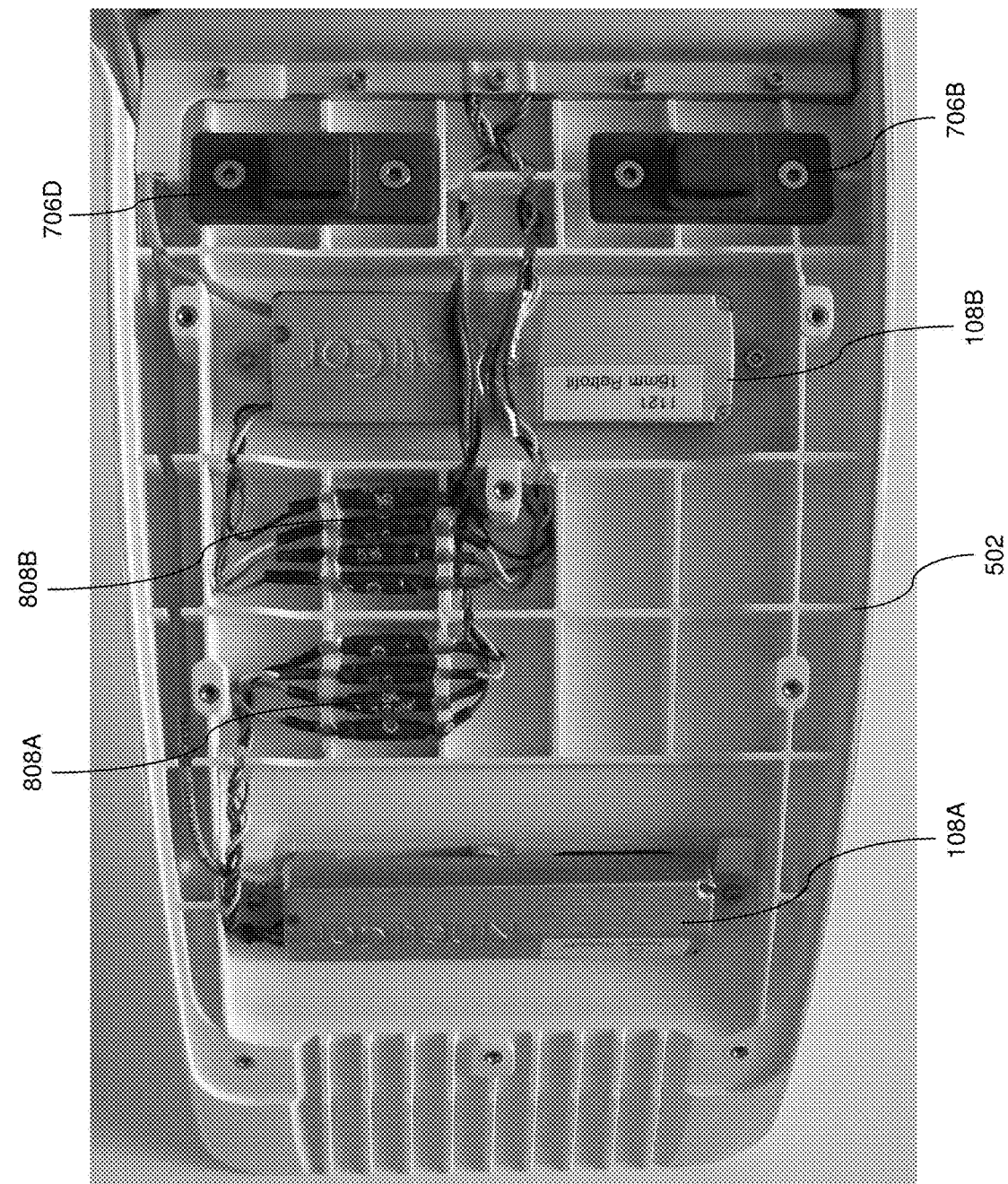

FIGS. 8A and 8B are top views of an embodiment of a motion correction device of a retrofit motion tracking and/or correction system. The device housing 502 may not include a top cover as the top of the device is configured to be covered by the bore 104 upon installation. The mounting bracket 702 may provide a top cover for the whole or portion of the top of the device in certain embodiments upon installation. In certain embodiments, the device housing 502 may include a separate top cover.

As illustrated, the device housing 502 can provide a cover for and/or comprise one or more device components. In some embodiments, as shown in FIGS. 8A and 8B, a motion correction device housing 502 comprises one or more camera modules or detectors 108A, 108B, 108C, 108D, a power unit 806, and one or more cables and/or wires. The device housing 502 can also comprise one or more allocated spaces to accommodate the one or more device components, including but not limited to the one or more camera modules or detectors 108A, 108B, 108C, 108D, a power unit 806, and one or more cables and/or wires.

In the embodiment shown in FIGS. 8A and 8B, a motion correction device housing 502 comprises a quad camera design or four camera modules 108A, 108B, 108C, 108D. In other embodiments, the device housing 502 can comprise fewer or additional camera modules or detectors 108 as described herein. In some embodiments, each of the one or more camera modules or detectors 108 can be connected to one or more RF chokes 808, for example through one or more wire or cable connections. RF chokes 808 can be advantageous for eliminating RF noise, including but not limited to digital RF noise. For example, in the illustrated embodiment, each camera module or detector 108A, 108B, 108C, 108D is connected to one or more RF chokes 808. More specifically, detector module 108A can be connected to four RF chokes 808A, and detector module 108B can be connected to four RF chokes 808B. In other embodiments, each detector module 108A, 108B, 108C, 108D can be connected to fewer or additional RF chokes 808.

Figure 9:
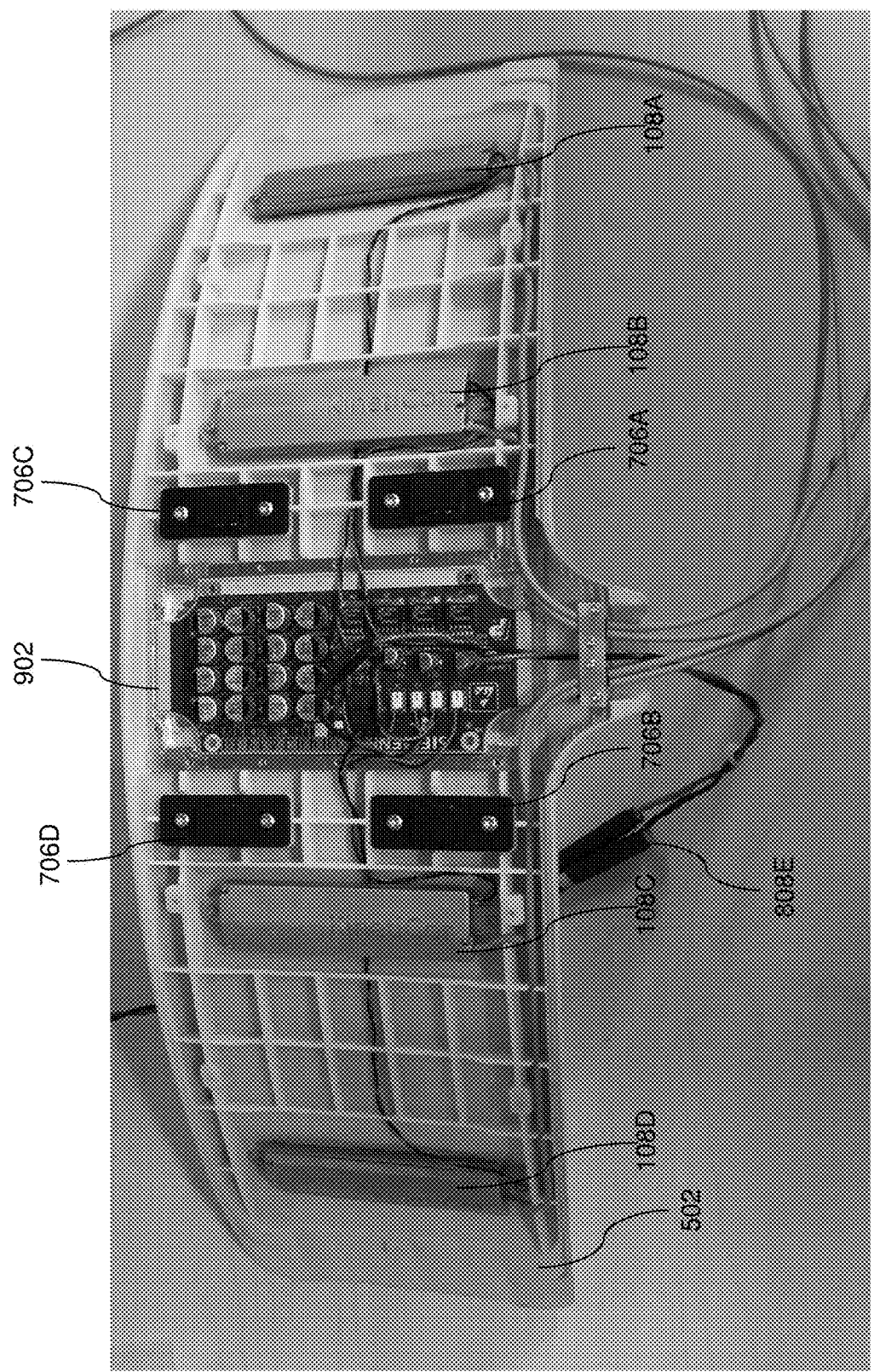
FIG. 9 is a top view of an embodiment of a motion correction device of a retrofit motion tracking and/or correction system.

FIG. 9 is a top view of an embodiment of a motion correction device of a retrofit motion tracking and/or correction system. As illustrated in FIG. 9, each camera or detector module 108 can be connected to a power unit 902, for example through one or more wire or cable connections. The power unit 902 can be removable, attachable, and/or removably attached or coupled. The power unit 902 can comprise a cover 806 in some embodiments as illustrated in FIG. 8A, for example to protect the components of the power unit 902. In certain embodiments, a power unit 902 comprises a power distribution board configured to send and regulate power to each of the one or more detector modules 108. This can be driven by a processing board. The processing board can be configured to be located remotely outside of the room where the medical imaging scanner is located, inside the room where the medical imaging scanner is located but not part of the device housing 502, as part of the medical imaging scanner, and/or as part of the motion correction device housing 502. The power unit 902 can be connected to one or more RF chokes 808E in a similar manner as the one or more camera or detector modules 108.

As discussed herein, in some embodiments, a motion correction device housing 502 can comprise one or more cables and/or wires to connect one or more device components. For example, the one or more cables and/or wires can comprise one or more power cables and/or signal transmission cables, such as fiber optics. The one or more power cables and/or one or more signal transmission cables can be configured to connect to an image processing unit. The image processing unit can be an image processing computer, digital signal processor (DSP), field-programmable gate array (FPGA), or others. In some embodiments, an FPGA on a sensor module is used for imaging processing, the results of which are transmitted to a Raspberry PI type processor (ARM) for further analysis. In certain embodiments, an image processing unit can be configured to send to the scanner data comprising recent or most recent head pose data in six degrees of freedom of the subject. In some embodiments, a motion correction device and/or system and/or medical imaging scanner is configured to utilize such data in order to alter the image acquisition plane.

Camera Module/Detector

As discussed above, a motion tracking and/or correction system and/or device can comprise one or more camera modules or detectors 108 configured to detect, track, and/or collect motion data of a subject.

Figure 10:
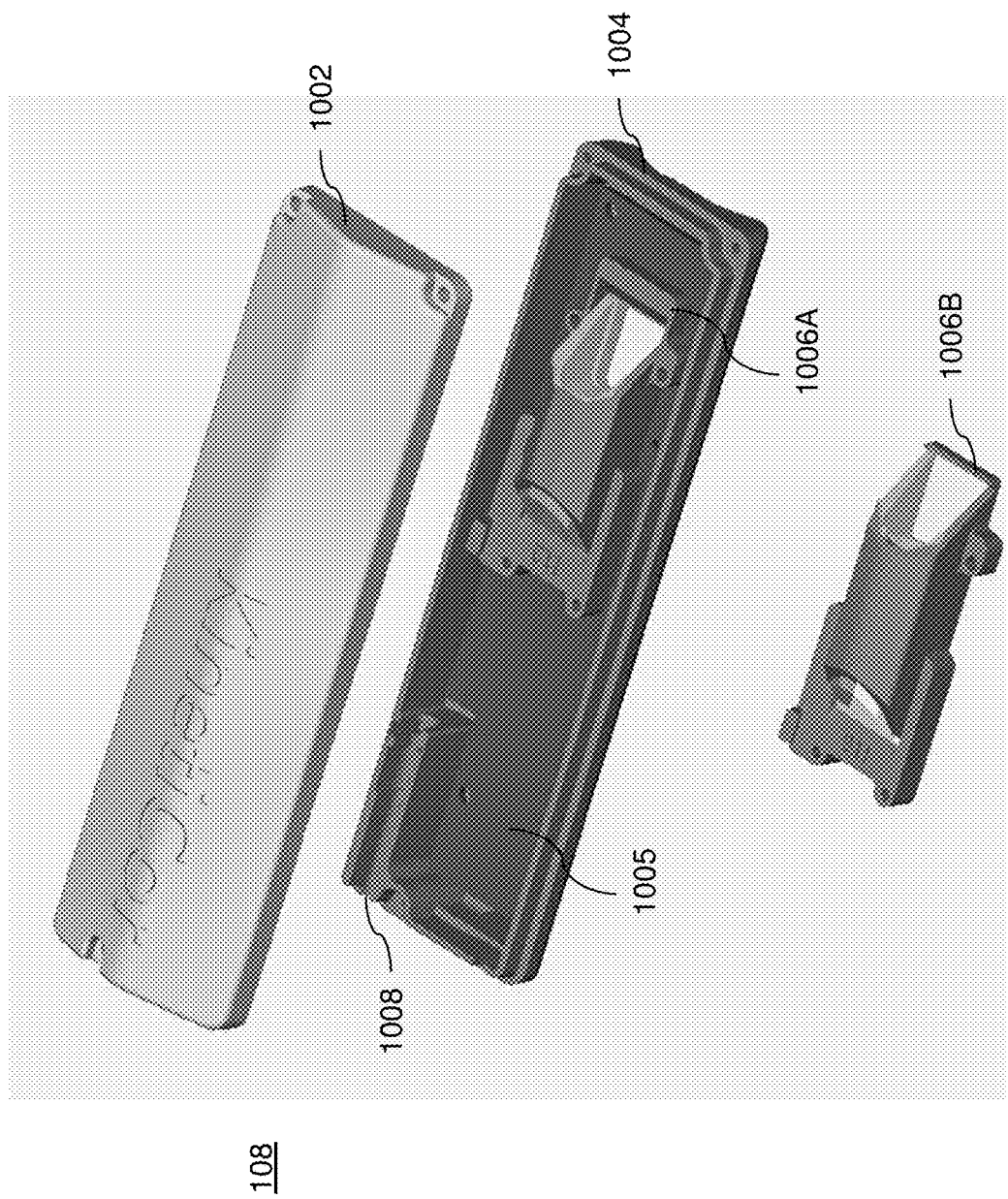
FIG. 10 is a schematic diagram illustrating a prospective view of an embodiment of a camera module or detector of a motion tracking and/or correction system.

FIG. 10 is a schematic diagram illustrating a prospective view of an embodiment of a camera module or detector of a motion tracking and/or correction system. As illustrated, in some embodiments, a camera module or detector 108 can comprise a substantially oblong shape or configuration. In other embodiments, a camera module or detector 108 can be substantially circular, square, rectangular, triangular, pentagonal, hexagonal, and/or elliptical in shape. In certain embodiments, a camera module or detector 108 can comprise a camera module or detector housing 1002, 1004 that is configured to house one or more sensor modules 1005. The sensor module can comprise a camera sensor (CMOS), sensor electronics, a processing FPGA, and one or more light sources, such as an LED. Each of the one or more sensor modules 1005 can comprise one or more optics modules 1006. The camera module or detector housing 1002, 1004 can comprise a top cover 1002 and a bottom cover 1004. The top cover 1002 and the bottom cover 1004 can be configured to be coupled or attached via screws, nuts, or the like. The top cover 1002 can be selectively removed from the bottom cover 1004, for example for maintenance and/or to switch out a sensor module 1005 and/or an optics module 1006.

In some embodiments, the top cover 1002 or other portion of the camera module or detector housing comprises one or more rounded corners to reduce RF emission. In certain embodiments, the top cover 1002, bottom cover 1004, and/or other portions of the camera module or detector housing comprises non-parallel walls to eliminate standing waves. In some embodiments, the top cover 1002, bottom cover 1004, optics module 1006, and/or any portion of the camera module or detector housing and/or optics module 1006 comprises ceramic material for rigidity and/or high thermal conductivity. Further, in some embodiments, the bottom cover 1004 and/or other portion of the camera module or detector housing comprises one or more waveguides 1008 to provide an exit for one or more wires, fiber-optics, and/or cables.

In some embodiments, the camera module or detector housing is configured such that one or more sensor modules 1005 and/or optics modules 1006 thereof can be switched. For example, it may be advantageous to easily replace one or more sensor modules 10056 and/or optics modules 1006 configured to be used in conjunction with and/or optimized for use with a particular medical image scanner with another sensor module 1005 and/or optics modules 1006 configured to be used in conjunction with and/or optimized for use with another particular medical image scanner. In some embodiments, to replace a sensor module 1005 and/or optics modules 1006, an operator can selectively remove a top cover 1002 from the bottom cover 1004 and replace the pre-installed sensor module 1005 comprising optics module 1006A with another sensor module comprising optics module 1006B. The sensor module 1005 and/or optics modules 1006 can be replaced for maintenance or repair reasons. Also or alternatively, a sensor module 1005 comprising optics module 1006A for use with a medical imaging scanner or therapeutic device with a 60 cm bore can be replaced with a sensor module comprising optics module 1006B for use with a medical imaging scanner or therapeutic device with a 70 cm bore.

Figure 11:
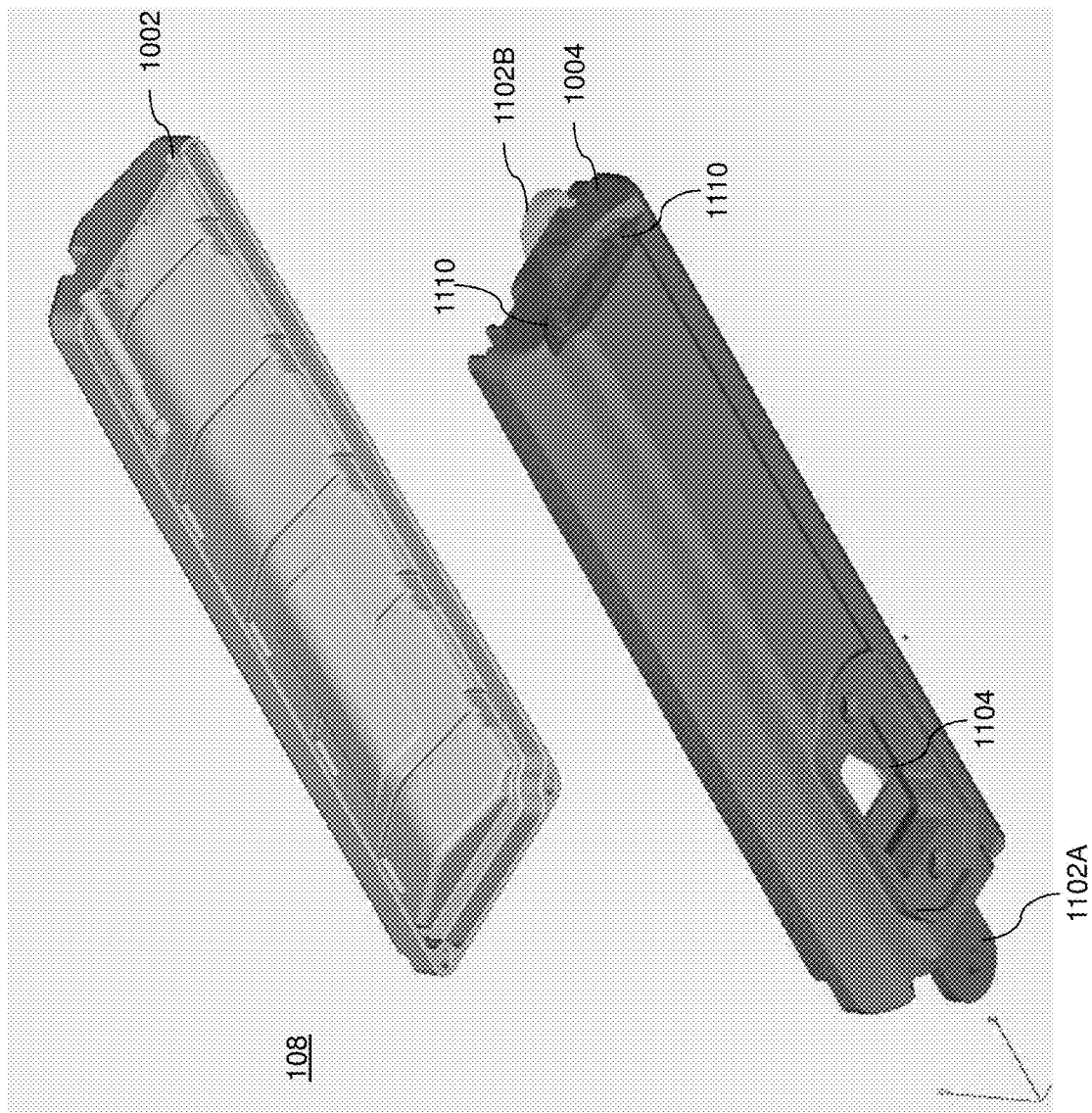
FIG. 11 is a schematic diagram illustrating a prospective view of an embodiment of the housing of a camera module or detector of a motion tracking and/or correction system.

FIG. 11 is a schematic diagram illustrating a prospective view of an embodiment of the housing of a camera module or detector of a motion tracking and/or correction system. In some embodiments, the inside and/or outside of the top cover 1002 and/or bottom cover 1004 can be plated with copper and/or optionally flash plated with nickel. For example, the top cover 1002 and/or bottom cover 1004 can be plated with 50 microns of copper, then flash plated with nickel. In certain embodiments, by having a ceramic top cover 1002 and/or bottom cover 1004 further coated and/or flash coated with copper and nickel any or substantially any electromagnetic interference (EMI) penetration can be prevented. The top cover 1002 and/or bottom cover 1004 can also or alternatively be flash plated with any other material to protect the copper from oxidation, such as but not limited to tin, silver, gold, and/or chrome. In addition, in certain embodiments, a camera module or detector housing, for example the bottom cover 1004, comprises one or more finger contacts 1102A, 1102B to assure connectivity to the retrofit device housing 502. The finger contacts 1102 can be integrated into top cover 1002 or bottom cover 1004 or may be separate components and connected to the top cover 1002 and/or bottom cover 1004 by means of screws 1110.

In some embodiments, the camera module or detector housing is goniometrically mounted to the device housing 502 to allow for optical alignment with the subject. Further, in certain embodiments, the camera module or detector housing comprises an optics opening 1104. The optics opening, in some embodiments, can be RF shielded by a dual layer comprising ITO coated glass window and/or wire mesh. Other materials and/or configurations can be used for RF shielding as well.

Figure 12:
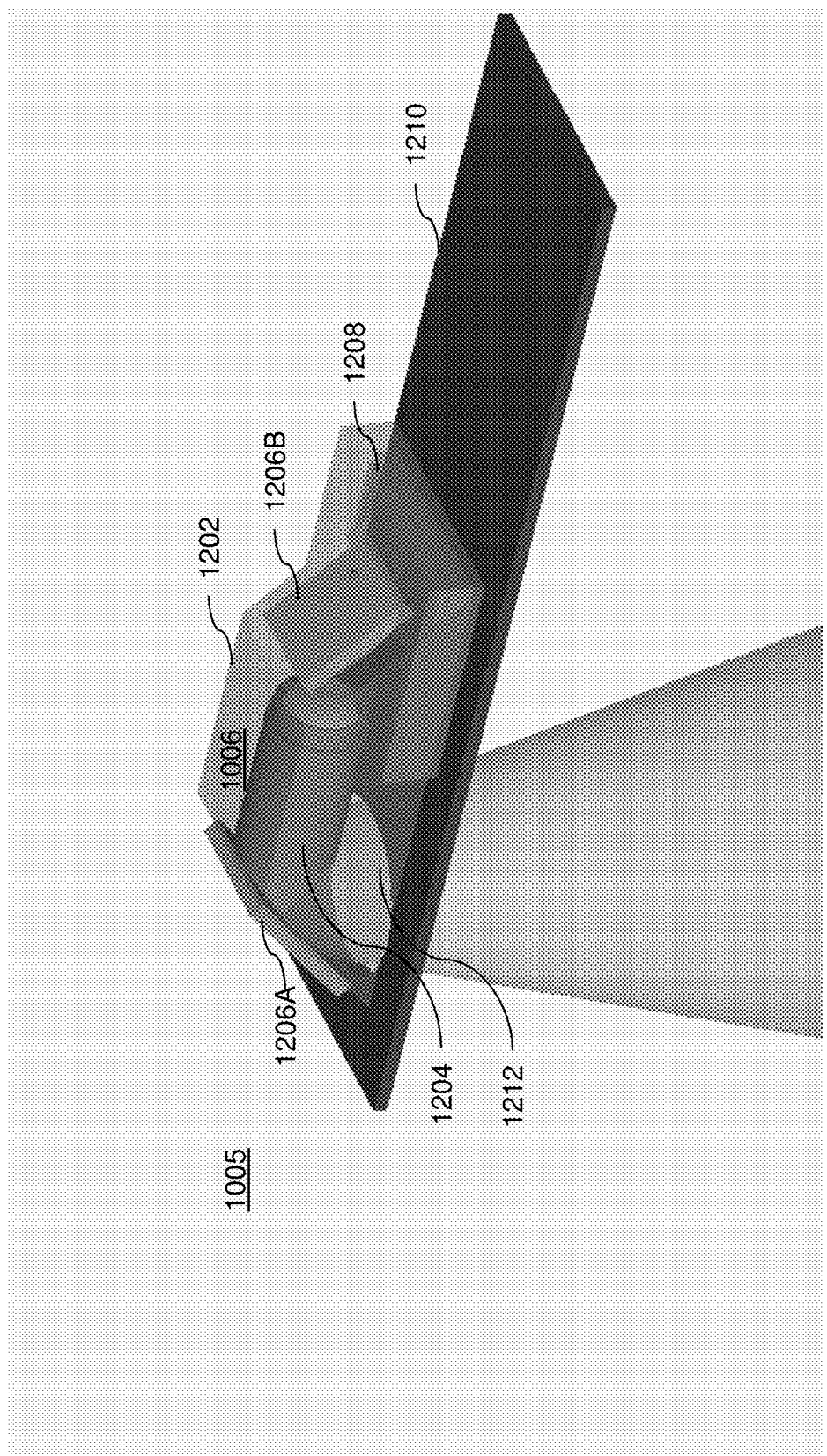
FIG. 12 is a schematic diagram illustrating a prospective view of an embodiment of a sensor module of a motion tracking and/or correction system.

FIG. 12 is a schematic diagram illustrating a prospective view of an embodiment of a sensor module of a motion tracking and/or correction system. The sensor module 1005 can comprise an imaging sensor, sensor electronics, an optics module 1006, and/or light source(s) for illumination. As illustrated, the optics module 1006 can comprise an optics housing 1202 positioned on a sensor module printed circuit board (PCB) 1210. The optics housing 1202 can form a top portion of the sensor module 1005. The sensor module PCB 1210 can comprise an opening 1212. The optics module housing 1202 can be configured to protect one or more components. For example, in some embodiments, the optics module housing 1202 can be configured to cover and/or provide protection for optics 1204, one or more mirrors 1206, a sensor 1208 on the sensor module PCB 1210, and one or more light sources, such as an Light Emitting Diode (LED).

The line of vision and/or visual field of the optics 1204 through a first end of the optics 1204 can be configured to be bent by a mirror 1206 and through the opening 1212 to view the subject. In other words, the first end of the optics 1204 and the opening 1212 can be configured in a perpendicular or angular configuration. Such configuration can be advantageous to allow for the optics 1204 to be placed horizontally along the longitudinal axis of the bore 104 of the medical imaging scanner, therapeutic device, and/or the sensor module 1005 to minimize space of the motion correction device. In other embodiments, the optics 1204 can be placed vertically perpendicular to the longitudinal axis of the bore 104 of the medical imaging scanner, therapeutic device, and/or the sensor module 1005 and may not require a mirror 1206A for the first end of the optics 1204 to view the subject through the opening 1212. In other words, the first end of the optics 1204 and the opening 1212 can generally be along a straight line. The mirror 1206A may also be configured to bend the light source towards the opening 1212. In certain embodiments, the light source may be configured to directly shine light through the opening 1212 without the light being bent through a mirror 1206A.

The motion data and/or visual data collected by the optics 1204 can then transmitted through a second end of the optics 1204 and be bent by another mirror 1206B to reach a sensor or imager 1208. In other words, the second end of the optics 1204 and the sensor 1208 can be configured in a perpendicular or angular configuration. Such configuration can be advantageous to allow for the optics 1204 to be placed horizontally along the longitudinal axis of the bore 104 of the medical imaging scanner, therapeutic device, and/or the sensor module to minimize space of the motion correction device. In other embodiments, the second end of the optics 1204 and the sensor 1208 can generally be along a straight line. For example, the sensor 1208 can be in a vertical configuration that is perpendicular or angular to the sensor module 1005. In the illustrated embodiment, the sensor 1208 is in a horizontal configuration and generally parallel to the sensor module 1005.

Figure 13:
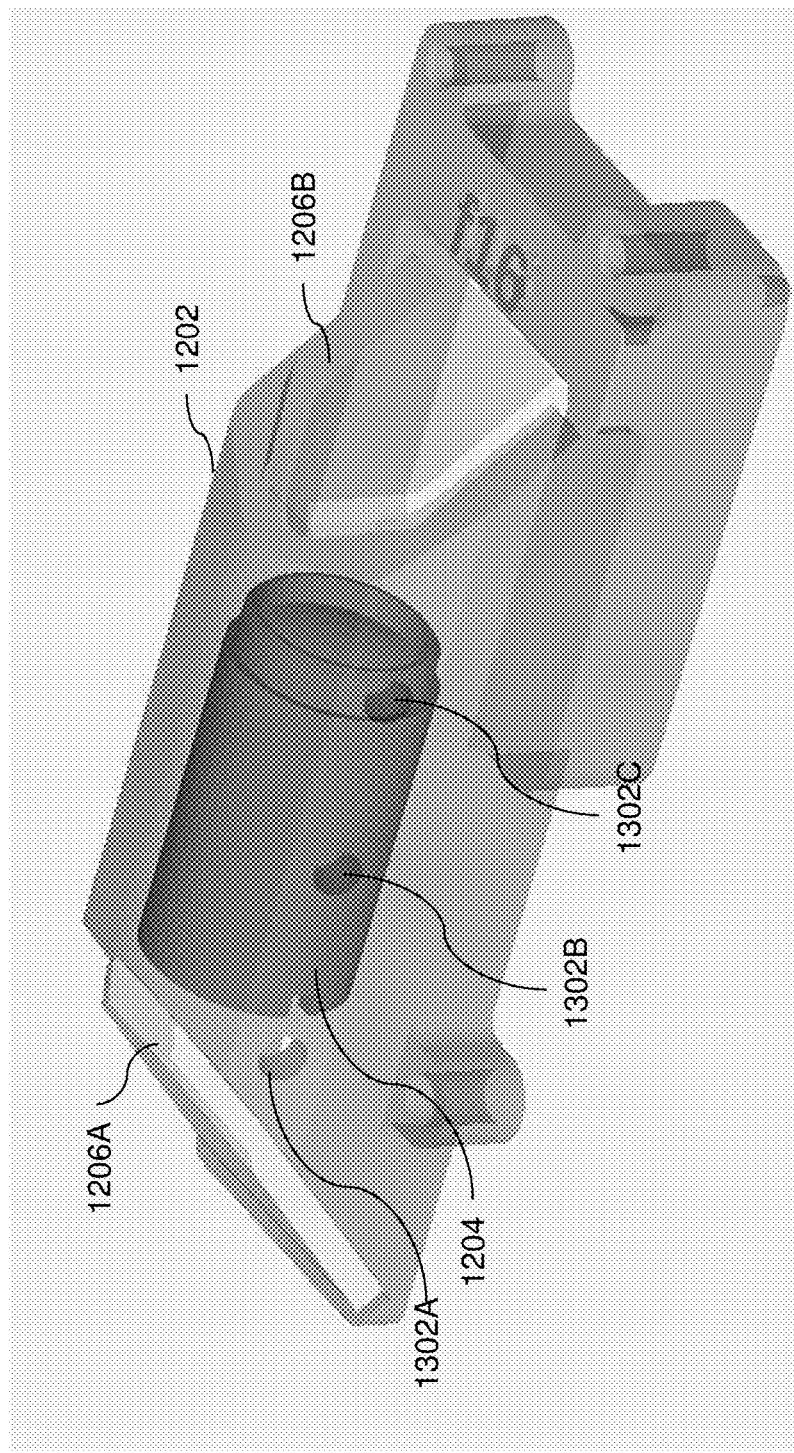
FIG. 13 is a schematic diagram illustrating a prospective view of an embodiment of an optics module of a motion tracking and/or correction system.

FIG. 13 is a schematic diagram illustrating a prospective view of an embodiment of an optics module of a motion tracking and/or correction system. As illustrated, optics 1204 can be placed within an optics module housing 1202. The optics 1202 can be fixated or anchored underneath the optics 1202 to provide stability. The optics module housing 1202 can comprise one or more holes 1302 for fixating the optics 1204 and/or other components underneath the optics module housing 1202. For example, in the illustrated embodiment, the optics module housing 1202 comprises three holes 1302A, 1302B, 1302C. In other embodiments, the optics module housing 1202 can comprise fewer or additional holes 1302.

In some embodiments, screws, nuts, or the like can be used to mechanically fixate the optics 1204 within the optics module housing 1202. For example, one or more screws, nuts, or the like can be placed through one or more holes 1302 to fixate the optics 1204. In the illustrated embodiment with three holes 1302A, 1302B, 1302C, screws, nuts, or the like can be placed through one, two, or all three holes 1302A, 1302B, 1302C to fixate the optics 1204. In some embodiments, the optics 1204 can be fixated by use of a single screw through a single hole 1302B. The optics 1204 can be fixated by use of glue or other chemical compound.

The optics 1204 can be 16 mm optics, for example for a large medical imaging scanner or therapeutics device with a diameter of about 70 cm. In addition or alternatively, the optics 1204 can be 12 mm optics, for example for a small medical imaging scanner or therapeutics devices with a diameter of about 60 cm. In certain embodiments, wider angle optics, such as 10 mm optics or 8 mm optics, can also or alternatively be used. To ensure appropriate focus distance to the patient subject, the position of the optics 1204 can be aligned through one or more of the holes 1302, prior to fixating the optics 1204.

Parameters

As discussed above, in some embodiments, one or more camera modules or detectors of a motion tracking and/or correction system and/or device can be optimally located in order to maximize the quality of motion data that is collected of a subject. Some of the following parameters are defined and/or described in the context of obtaining motion data of a head of a subject. However, it is to be understood that similar parameters can also be defined for other body portions of a subject that are of interest in a medical imaging scan and/or therapeutic procedure.

Figure 14B:
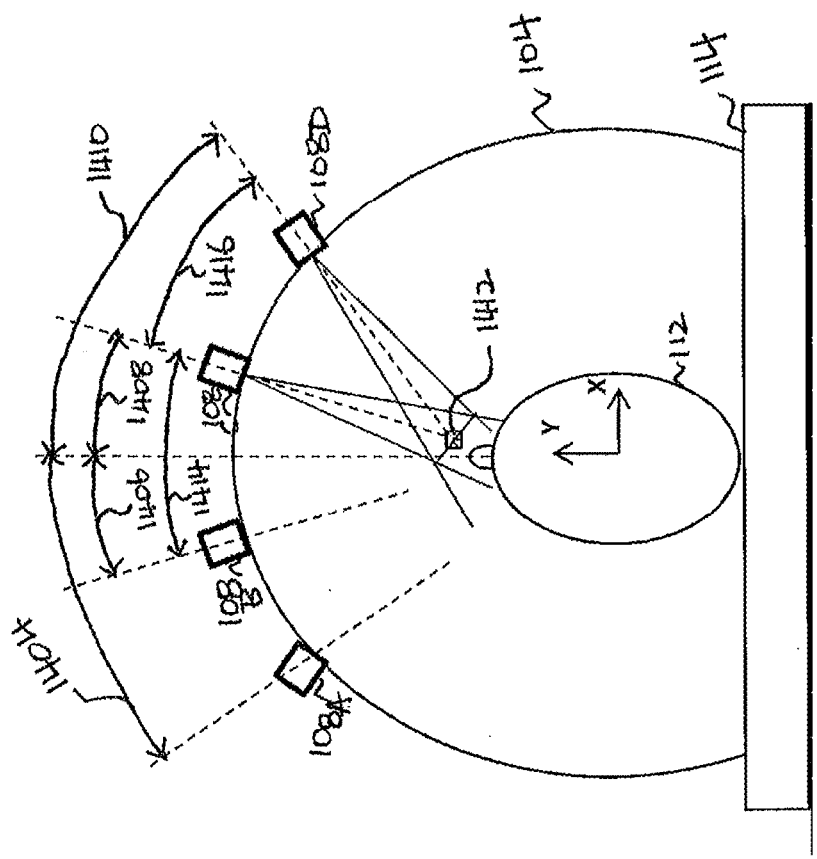
FIG. 14B is a schematic diagram illustrating a front view of an embodiment of a medical imaging scanner or therapeutic device as a part of a motion tracking and/or correction system with details of the detector position(s) and direction(s)
Figure 14A:
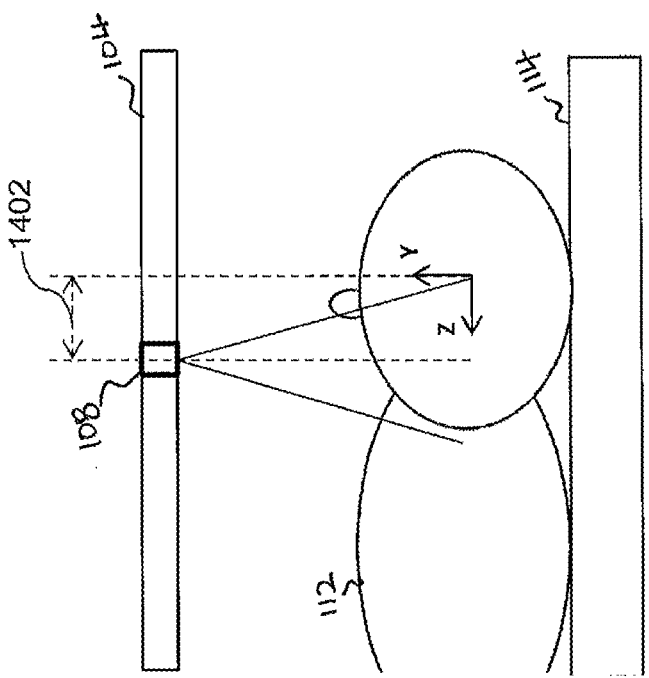
FIG. 14A is a schematic diagram illustrating a side view of an embodiment of a medical imaging scanner or therapeutic device as a part of a motion tracking and/or correction system with details of the camera position(s) and direction(s)

FIG. 14A is a schematic diagram illustrating a side view of an embodiment of a medical imaging scanner or therapeutic device as a part of a motion tracking and/or correction system with details of the camera position(s) and direction(s). FIG. 14B is a schematic diagram illustrating a front view of an embodiment of a medical imaging scanner or therapeutic device as a part of a motion tracking and/or correction system with details of the detector position(s) and direction(s).

As illustrated, a subject of interest 112 can lie on a bed 114 of a medical imaging scanner and/or therapeutic device. One or more detectors or cameras 108 can be placed on or along the bore 104 of the scanner or therapeutic device.

A longitudinal detector position 1402 along the Z-axis between the center of the MRI scanner or therapeutic device and the camera module or detector 108 can exist for different detectors used in conjunction with different medical imaging scanners and/or therapeutic devices. In some embodiments, the longitudinal detector position 1402 can be about +/−0 mm, about +/−10 mm, about +/−20 mm, about +/−30 mm, about +/−40 mm, about +/−50 mm, about +/−60 mm, about +/−70 mm, about +/−80 mm, about +/−90 mm, about +/−100 mm, about +/−150 mm, about +/−200 mm, about +/−250 mm, about +/−300 mm, about +/−350 mm, about +/−400 mm, about +/−450 mm, about +/−500 mm, about +/−550 mm, about +/−600 mm, about +/−650 mm, about +/−700 mm, about +/−750 mm, about +/−800 mm, about +/−850 mm, about +/−900 mm, about +/−950 mm, about +/−1000 mm, and/or in a range defined by any of the two aforementioned values.

Similarly, a transversal detector position 1404, 1406 on the X-Y plane as defined herein can exist for different detectors used in conjunction with different medical imaging scanners and/or therapeutic devices. In certain embodiments, the transversal detector position 1404, 1406 can be about 0°, about 10°, about 20°, about 30°, about 40°, about 50°, about 60°, about 70°, about 80°, about 90°, about 110°, about 120°, about 130°, about 140°, about 150°, about 160°, about 170°, about 180°, and/or in a range defined by any of the two aforementioned values.

A transversal detector direction 1408, 1410 on the X-Y plane as defined herein can exist for different detectors used in conjunction with different medical imaging scanners and/or therapeutic devices, as the direction of a detector can be different from the position thereof. In some embodiments, the transversal detector direction 1408, 1410 can be about 0°, about 10°, about 20°, about 30°, about 40°, about 50°, about 60°, about 70°, about 80°, about 90°, about 110°, about 120°, about 130°, about 140°, about 150°, about 160°, about 170°, about 180°, and/or in a range defined by any of the two aforementioned values.

A transversal detector offset on the X-Y plane as defined herein can exist for different detectors used in conjunction with different medical imaging scanners and/or therapeutic devices, in which the transversal detector offset can be defined as the difference between the transversal detector position and the transversal detector direction. In certain embodiments, the transversal camera offset can be about 0°, about 10°, about 20°, about 30°, about 40°, about 50°, about 60°, about 70°, about 80°, about 90°, about 110°, about 120°, about 130°, about 140°, about 150°, about 160°, about 170°, about 180°, and/or in a range defined by any of the two aforementioned values.

An overlap point 1412 between the field of view of the different detectors can exist on the X-Y plane as defined herein for different detectors used in conjunction with different medical imaging scanners and/or therapeutic devices. In some embodiments, x-y coordinates for the overlap point 1412 can each comprise about 0 mm, about 10 mm, about 20 mm, about 30 mm, about 40 mm, about 50 mm, about 60 mm, about 70 mm, about 80 mm, about 90 mm, about 100 mm, about 110 mm, about 120 mm, about 130 mm, about 140 mm, about 150 mm, about 160 mm, about 170 mm, about 180 mm, about 190 mm, about 200 mm, and/or in a range defined by any of the two aforementioned values.

Lastly, a scissor angle 1414, 1416 can exist between two detectors on the X-Y plane as defined herein for different detectors used in conjunction with different medical imaging scanners and/or therapeutic devices. In certain embodiments, a larger scissor angle can result in increased accuracy of tracking. In some embodiments, the scissor angle can be about 0°, about 10°, about 20°, about 30°, about 40°, about 50°, about 60°, about 70°, about 80°, about 90°, about 110°, about 120°, about 130°, about 140°, about 150°, about 160°, about 170°, about 180°, and/or in a range defined by any of the two aforementioned values.

Each of the above-identified parameters can be different from an integrated motion tracking and/or correction system, a retrofit motion tracking and/or correction system, and/or specific head coils. Some example values of the above-identified parameters are included below. However, other values are also possible for each of the parameters depending on the detector and/or specifics of the medical imaging scanner and/or therapeutic device.

TABLE 1

Camera Positions and Directions for a Medical Imaging Scanner with a Diameter of About 70 cm and an Integrated Motion Tracking and/or Correction System

| Diameter of Scanner | Detector System | Longitudinal Detector Position (Z) | Transversal Detector Position (X-Y) | Transversal Detector Direction (X-Y) | Transversal Camera Offset (X-Y) | Overlap Point (X; Y) | Scissor Angle |
|---|---|---|---|---|---|---|---|
| 694.5 mm | Detectors 108B and 108C | 44 mm (1402) | ±16.875° (1406) | ±16.875° (1408) | 0° | 33.5 mm; 110.4 mm (1412) | 33.750° (between 108B and 108C, 1414) |
| 694.5 mm | Detectors 108A and 108D | 44 mm (1402) | ±39.325° (1404) | ±49.250° (1410) | 9.925° | 33.5 mm; 110.4 mm (1412) | 32.375° (between 108C and 108D, 1416) |
| 684.24 mm | Detectors 108B and 108C | 44 mm (1402) | ±20.625° (1406) | ±22.125° (1408) | 1.5° | 33 mm; 108 mm (1412) | 44.25° (between 108B and 108C, 1414) |
| 684.24 mm | Detectors 108A and 108D | 44 mm (1402) | ±43.125° (1404) | ±54.125° (1410) | 11° | 33 mm; 108 mm (1412) | 32.00° (between 108C and 108D, 1416) |

TABLE 2

Camera Positions and Directions for a Medical Imaging Scanner with a Diameter of About 70 cm and a Retrofit Motion Tracking and/or Correction System

| Diameter of Scanner | Detector System | Longitudinal Detector Position (Z) | Transversal Detector Position (X-Y) | Transversal Detector Direction (X-Y) | Transversal Camera Offset (X-Y) | Overlap Point (X; Y) | Scissor Angle |
|---|---|---|---|---|---|---|---|
| 685.5 mm | Detectors 108B and 108C | <44 mm (1402) | ±16.875° (1406) | ±16.875° (1408) | 0° | 32 mm; 106 mm (1412) | 33.750° (between 108B and 108C, 1414) |

TABLE 2-continued

Camera Positions and Directions for a Medical Imaging Scanner with a Diameter of About 70 cm and a Retrofit Motion Tracking and/or Correction System

| Diameter of Scanner | Detector System | Longitudinal Detector Position (Z) | Transversal Detector Position (X-Y) | Transversal Detector Direction (X-Y) | Transversal Camera Offset (X-Y) | Overlap Point (X; Y) | Scissor Angle |
|---|---|---|---|---|---|---|---|
| 685.5 mm | Detectors 108A and 108D | <44 mm (1402) | ±39.385° (1404) | ±49.385° (1410) | 10° | 32 mm; 106 mm (1412) | 32.51° (between 108C and 108D, 1416) |
| 597 mm | Detectors 108B and 108C | 38 mm (1402) | ±13.50° (1406) | ±16.25° (1408) | 2.75° | 22 mm; 127.5 mm (1412) | 32.50° (between 108B and 108C, 1414) |
| 597 mm | Detectors 108A and 108D | 38 mm (1402) | ±32.00° (1404) | ±47.25° (1410) | 15.25° | 22 mm; 127.5 mm (1412) | 31.00° (between 108C and 108D, 1416) |

Figure 15:
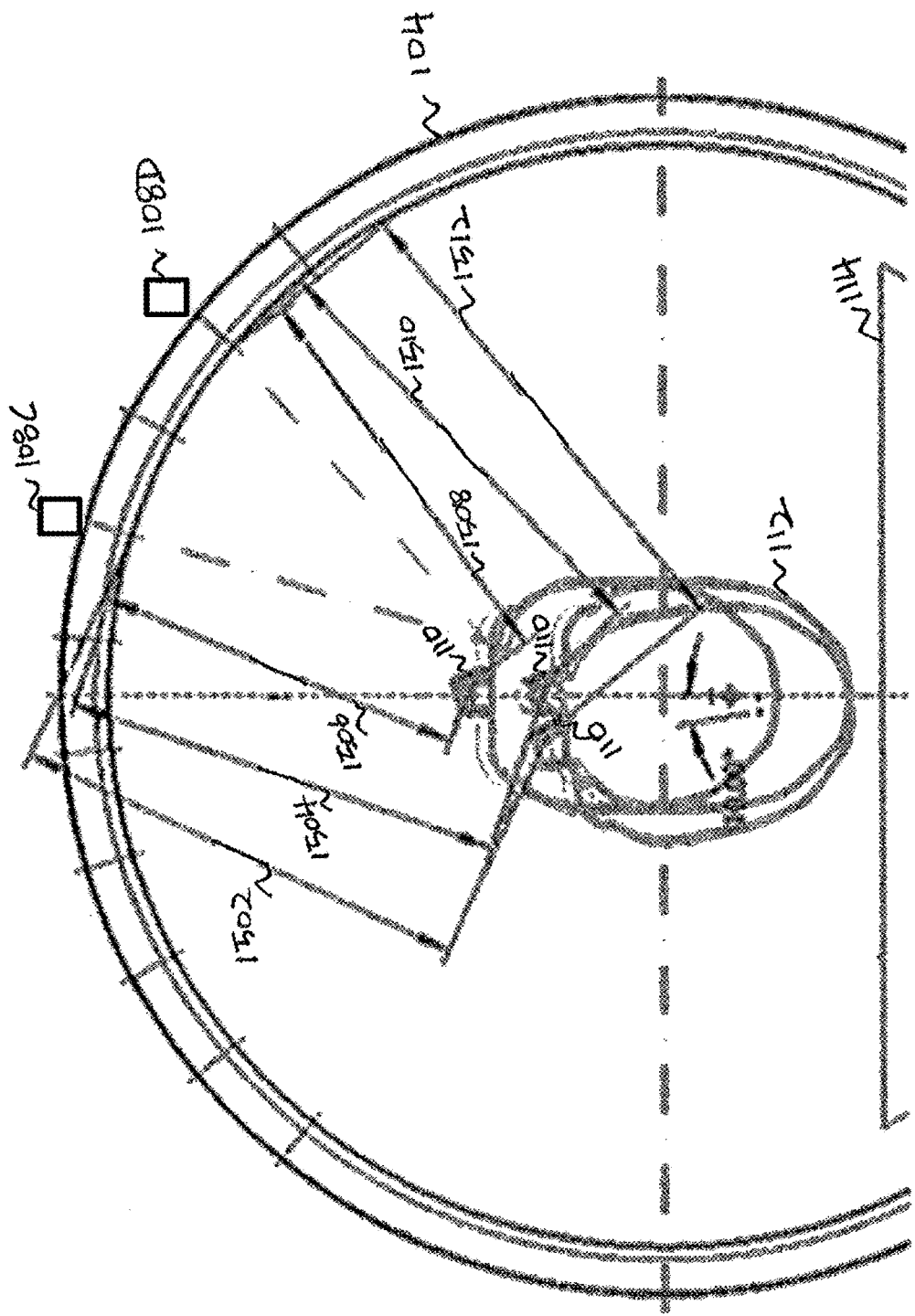
FIG. 15 is a schematic diagram illustrating a front view of an embodiment of a medical imaging scanner or therapeutic device as a part of a motion tracking and/or correction system with details of the distance between a body coil and a marker(s)

FIG. 15 is a schematic diagram illustrating a front view of an embodiment of a medical imaging scanner or therapeutic device as a part of a motion tracking and/or correction system with details of the distance between a body coil and a marker(s).

As illustrated, a subject of interest 112 can lie on a bed 114 of a medical imaging scanner and/or therapeutic device. A marker 110 as described herein may be placed on or near the nose of the subject 112. The head of the subject 112 may rotate, thereby rotating the marker 110 as well. As illustrated, a distance between the body coil and the marker 110 may be obtained.

More specifically, a minimum distance between the body coil and the marker 110 may be present, measured when the nose of the subject 112 is at the end of the head coil and/or is in contact with the head coil. A default distance between the body coil and the marker 110 may exist, measured when the head of subject 112 is at a default position in the center of the head coil facing straight up towards the center of the top of the bore 104. Lastly a maximum distance between the body coil and the marker 110 can be measured, for example when the head of the subject 112 is rotated 10 degrees for certain head coils. For other head coils, smaller or larger rotations are also or alternatively possible. For example, in certain embodiments, the head of the subject 112 can be rotated about 5 degrees, about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, about 90 degrees, and/or within a range defined by two of the aforementioned values.

The minimum distance, default distance, and maximum distance between the body coil and the marker 110 can each be about 100 mm, about 110 mm, about 120 mm, about 130 mm, about 140 mm, about 150 mm, about 160 mm, about 170 mm, about 180 mm, about 190 mm, about 200 mm, about 210 mm, about 220 mm, about 230 mm, about 240 mm, about 250 mm, about 260 mm, about 270 mm, about 280 mm, about 290 mm, about 300 mm, about 310 mm, about 320 mm, about 330 mm, about 340 mm, about 350 mm, about 360 mm, about 370 mm, about 380 mm, about 390 mm, about 400 mm, and/or within a range defined by two of the aforementioned values.

A range of the distance between the body coil to the marker 110 can be obtained based on the above-identified parameters. Further, based on this range of the distance between the body coil to the marker 110, an alignment distance, defined as the distance between the detector module 108C, 108D to the marker 110 can be obtained, accounting for a range of +10 mm and rounded by −2/+4 mm.

Each of the above-identified parameters can be different from an integrated motion tracking and/or correction system and a retrofit motion tracking and/or correction system. Further, each of the above-identified parameters can be different for different head coils being used, for example a head coil with a 64 head-neck (HN64) configuration or a 20 head-neck (HN20) configuration.

Some example values of the above-identified parameters are included below. However, other values are also possible for each of the parameters depending on the detector and/or specifics of the medical imaging scanner and/or therapeutic device.

TABLE 3

Distance Between Body Coil and Marker for a Medical Imaging Scanner with a Diameter of About 684.52 mm and an Integrated Motion Tracking and/or Correction System

| | HN 64 (mm) | | HN 20 (mm) | |
|---|---|---|---|---|
| Marker Position | Detector 108C | Detector 108D | Detector 108C | Detector 108D |
| Minimum (nose at head coil) | 230 (1506) | 259 (1508) | 230 (1506) | 259 (1508) |
| Default | 272 (1504) | 285 (1510) | 276 (1504) | 289 (1510) |
| Maximum (rotated 10°) | 288 (1502) | 312 (1512) | 292 (1502) | 315 (1512) |
| Range | | 230~315 (272.5 +/− 42.5) | | |
| Alignment Distance | | 240~325 (280 +/− 45) | | |

TABLE 4

Distance Between Body Coil and Marker for a Medical Imaging Scanner with a Diameter of About 694.5 mm and an Integrated Motion Tracking and/or Correction System

| Marker Position | HN 64 (mm) | | HN 20 (mm) | |
| --- | --- | --- | --- | --- |
| | Detector 108C | Detector 108D | Detector 108C | Detector 108D |
| Minimum (nose at head coil) | 233 (1506) | 258 (1508) | 232 (1506) | 258 (1508) |
| Default | 276 (1504) | 287 (1510) | 281 (1504) | 291 (1510) |
| Maximum (rotated 10°) | 289 (1502) | 313 (1512) | 294 (1502) | 316 (1512) |
| Range | | 232~316 (274 +/− 45) | | |
| Alignment Distance | | 240~330 (285 +/− 45) | | |

TABLE 5

Distance Between Body Coil and Marker for a Medical Imaging Scanner with a Diameter of About 685.5 mm and a Retrofit Motion Tracking and/or Correction System

| Marker Position | HN 64 (mm) | | HN 20 (mm) | |
| --- | --- | --- | --- | --- |
| | Detector 108C | Detector 108D | Detector 108C | Detector 108D |
| Minimum (nose at head coil) | 228 (1506) | 254 (1508) | 228 (1506) | 253 (1508) |
| Default | 271 (1504) | 283 (1510) | 276 (1504) | 286 (1510) |
| Maximum (rotated 10°) | 285 (1502) | 308 (1512) | 289 (1502) | 311 (1512) |
| Range | | 228~311 (269.5 +/− 41.5) | | |
| Alignment Distance | | 205~295 (250 +/− 45) | | |

TABLE 6

Distance Between Body Coil and Marker for a Medical Imaging Scanner with a Diameter of About 597 mm and a Retrofit Motion Tracking and/or Correction System

| Marker Position | HN 64 (mm) | | HN 20 (mm) | |
| --- | --- | --- | --- | --- |
| | Detector 108C | Detector 108D | Detector 108C | Detector 108D |
| Minimum (nose at head coil) | 154 (1506) | 181 (1508) | 154 (1506) | 181 (1508) |
| Default | 198 (1504) | 212 (1510) | 203 (1504) | 215 (1510) |
| Maximum (rotated 10°) | 211 (1502) | 236 (1512) | 215 (1502) | 239 (1512) |
| Range | | 154~239 (196.5 +/− 42.5) | | |
| Alignment Distance | | 130~220 (175 +/− 45) | | |

Figure 16:
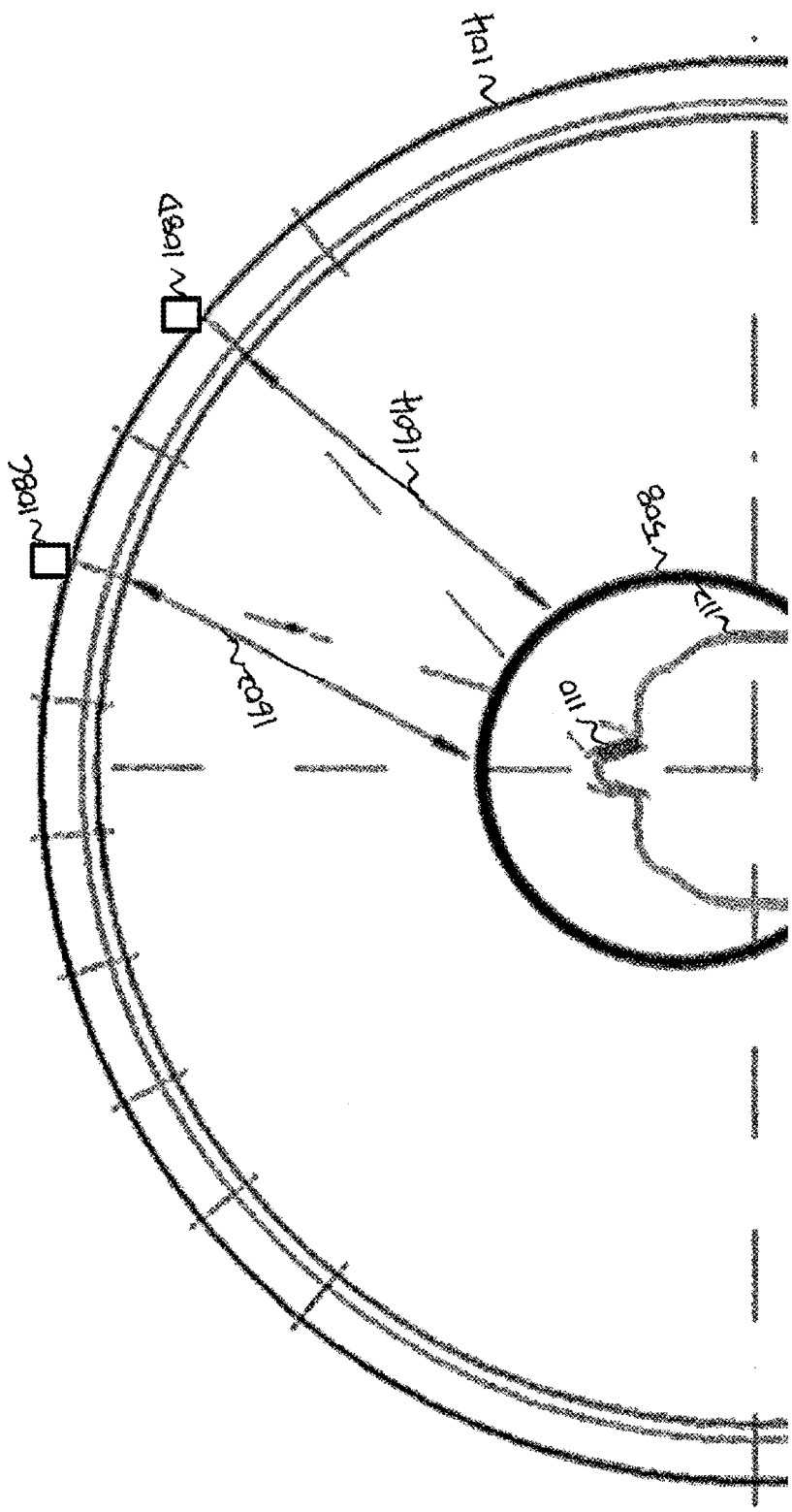
FIG. 16 is a schematic diagram illustrating a front view of an embodiment of a medical imaging scanner or therapeutic device as a part of a motion tracking and/or correction system with details of the distance between a body coil and a head coil.

FIG. 16 is a schematic diagram illustrating a front view of an embodiment of a medical imaging scanner or therapeutic device as a part of a motion tracking and/or correction system with details of the distance between a body coil and a head coil. As illustrated, a distance 1602, 1604 between the exterior surface of the head coil 508 and one or more detectors 108C, 108D can be measured. For example, a first minimum distance 1602 between the exterior surface of the head coil 508 and a first detector 108C can be obtained. Similarly, a second minimum distance 1604 between the exterior surface of the head coil 508 and a second detector 108D can be obtained. A minimum distance 1602, 1604 between a body coil and a head coil 508 can be deemed a minimum distance that must be maintained for the safety of the subject from illumination, for example from an LED light source.

In certain embodiments, the minimum distance 1602, 1604 between a body coil and a head coil 508 can be about 0 mm, about 10 mm, about 20 mm, about 30 mm, about 40 mm, about 50 mm, about 60 mm, about 70 mm, about 80 mm, about 90 mm, about 100 mm, about 110 mm, about 120 mm, about 130 mm, about 140 mm, about 150 mm, about 160 mm, about 170 mm, about 180 mm, about 190 mm, about 200 mm, about 210 mm, about 220 mm, about 230 mm, about 240 mm, about 250 mm, and/or within a range defined by two of the aforementioned values.

Each of the above-identified parameters can be different from an integrated motion tracking and/or correction system and a retrofit motion tracking and/or correction system. Further, each of the above-identified parameters can be different for different head coils being used, for example a head coil with a 64 head-neck configuration or a 20 head-neck configuration.

Some example values of the above-identified parameters are included below. However, other values are also possible for each of the parameters depending on the detector and/or specifics of the medical imaging scanner and/or therapeutic device.

TABLE 7

Distance between Body Coil and Head Coil for a Medical Imaging Scanner with a Diameter of About 694.5 mm and an Integrated Motion Tracking and/or Correction System

| | HN-64 Head Coil (mm) | | HN-20 Head Coil (mm) | |
| --- | --- | --- | --- | --- |
| | Detector 108C (1602) | Detector 108D (1604) | Detector 108C (1602) | Detector 108D (1604) |
| Distance Between Body Coil and Head Coil | 205 | 206 | 202 | 190 |
| Minimum | | 205 | | 190 |
| Minimum | | | 190 | |

TABLE 8

Distance between Body Coil and Head Coil for a Medical Imaging Scanner with a Diameter of About 684.52 mm and an Integrated Motion Tracking and/or Correction System

| | HN-64 Head Coil (mm) | | HN-20 Head Coil (mm) | |
| --- | --- | --- | --- | --- |
| | Detector 108C (1602) | Detector 108D (1604) | Detector 108C (1602) | Detector 108D (1604) |
| Distance Between Body Coil and Head Coil | 204 | 203 | 201 | 186 |
| Minimum | | 203 | | 186 |
| Minimum | | | 186 | |

TABLE 9

Distance between Body Coil and Head Coil for a Medical Imaging Scanner with a Diameter of About 685.5 mm and a Retrofit Motion Tracking and/or Correction System

| | HN-64 Head Coil (mm) | | HN-20 Head Coil (mm) | |
|---|---|---|---|---|
| | Detector 108C (1602) | Detector 108D (1604) | Detector 108C (1602) | Detector 108D (1604) |
| Distance Between Body Coil and Head Coil | 200 | 203 | 197 | 186 |
| Minimum | 200 | | 186 | |
| Minimum | | 186 | | |

TABLE 10

Distance between Body Coil and Head Coil for a Medical Imaging Scanner with a Diameter of About 597 mm and an Integrated Motion Tracking and/or Correction System

| | HN-64 Head Coil (mm) | | HN-20 Head Coil (mm) | |
|---|---|---|---|---|
| | Detector 108C (1602) | Detector 108D (1604) | Detector 108C (1602) | Detector 108D (1604) |
| Distance Between Body Coil and Head Coil | 127 | 134 | 124 | 118 |
| Minimum | 127 | | 118 | |
| Minimum | | 118 | | |

Tables 11-14 below list parameters of various distances and fields of view of four embodiments of camera modules or detectors. More specifically, Tables 11 and 12 list parameters of various distances and fields of view of two embodiments of camera modules or detectors of an integrated motion tracking and/or correction system. Tables 13 and 14 list parameters of various distances and fields of view of two embodiments of camera modules or detectors of a retrofit motion tracking and/or correction system.

In Tables 11-14, the optics value refers to the field of view, depth of field, and resolution for tracking. The marker distance refers to the distance between the body coil and the marker. The lens working distance refers to the distance between the marker and the front lens of the detector module. The lens center distance refers to the distance between the marker and the center of the lens of the detector module. The camera alignment distance refers to the distance between the front of the detector module to the marker. The back focal length refers to the lens data at the lens working distance. The field of view radius refers to the distance between the optics center and the scanner center. The field of view (half angle) and field of view at marker refer to lens data. The body coil to head coil distance refers to the distance between the body coil and the exterior of the head coil. The LED hazard distance refers to the distance between the LED source and the head coil. The LED illumination distance refers to the distance between the LED source to the marker.

TABLE 11

Distances and Fields of View of Detector Modules of an Integrated Motion Tracking and/or Correction System for a Medical Imaging Scanner with a Diameter of About 694.5 mm

| Description | Value |
|---|---|
| Body Coil Radius, r(BC) | 347.25 mm |
| Gradient Coil Radius, R(GC) | 376.5 mm |
| Optics | 16 mm, F5.6 |
| Marker Distance | 274 +/− 42 mm |
| Lens Working Distance (WD) | ~301 mm |
| Lens Center Distance | ~307 mm |
| Camera Alignment Distance | 284 mm |
| Back Focal Length (BFL) | 12.07 mm |
| Field of View Radius | ~376.5 |
| Field of View (half angle) | 10.3° × 8.3° |
| Field of View at Marker | 112 × 90 mm |
| Body Coil to Head Coil Distance | 190 mm |
| LED Hazard Distance | 200 mm |
| LED Illumination Distance | ~290 mm |

TABLE 12

Distances and Fields of View of Detector Modules of an Integrated Motion Tracking and/or Correction System for a Medical Imaging Scanner with a Diameter of About 684.52 mm

| Description | Value |
|---|---|
| Body Coil Radius, r(BC) | 342.25 mm |
| Gradient Coil Radius, R(GC) | 376.5 mm |
| Optics | 16 mm, F5.6 |
| Marker Distance | 272.5 +/− 42.5 mm |
| Lens Working Distance (WD) | ~300 mm |
| Lens Center Distance | ~307 mm |
| Camera Alignment Distance | 284 mm |
| Back Focal Length (BFL) | 12.07 mm |
| Field of View Radius | ~376.5 |
| Field of View (half angle) | 10.3° × 8.3° |
| Field of View at Marker | 112 × 90 mm |
| Body Coil to Head Coil Distance | 190 mm |
| LED Hazard Distance | 200 mm |
| LED Illumination Distance | ~290 mm |

TABLE 13

Distances and Fields of View of Detector Modules of a Retrofit Motion Tracking and/or Correction System for a Medical Imaging Scanner with a Diameter of About 685.5 mm

| Description | Value |
|---|---|
| Body Coil Radius, r(BC) | 342.75 mm |
| Optics | 16 mm, F5.6 |
| Marker Distance | 270 mm |
| Lens Working Distance (WD) | 265 mm |
| Lens Center Distance | 270 mm |
| Camera Alignment Distance | ~250 mm |
| Back Focal Length (BFL) | 12.17 mm |
| Field of View Radius | ~342.75 |
| Field of View (half angle) | 10.3° × 8.3° |
| Field of View at Marker | 100 × 80 mm |
| Body Coil to Head Coil Distance | 186 mm |
| LED Hazard Distance | 165 mm |
| LED Illumination Distance | ~250 mm |

TABLE 14

Distances and Fields of View of Detector Modules of a Retrofit Motion Tracking and/or Correction System for a Medical Imaging Scanner with a Diameter of About 597 mm

| Description | Value |
| --- | --- |
| Body Coil Radius, r(BC) | 298.5 mm |
| Optics | 12 mm, F5.6 |
| Marker Distance | 200 mm |
| Lens Working Distance (WD) | 195 mm |
| Lens Center Distance | 200 mm |
| Camera Alignment Distance | ~180 mm |
| Back Focal Length (BFL) | ~9.07 mm |
| Field of View Radius | ~298.5 |
| Field of View (half angle) | 13.5° × 10.9° |
| Field of View at Marker | 96 × 77 mm |
| Body Coil to Head Coil Distance | 118 mm |
| LED Hazard Distance | 100 mm |
| LED Illumination Distance | 160 mm |

Figure 17B:
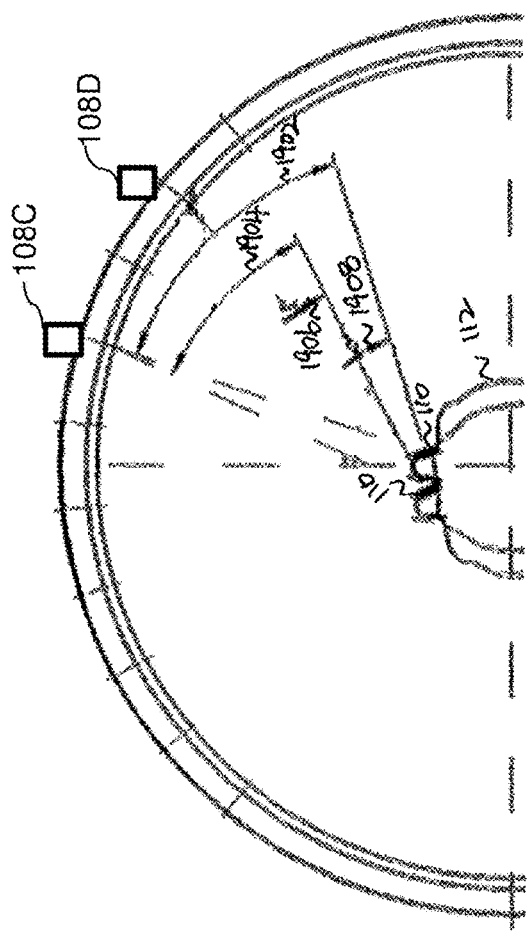
FIG. 17B is a schematic diagram illustrating entrance angles of an embodiment of camera modules or detectors of a motion tracking and/or correction system.
Figure 17A:
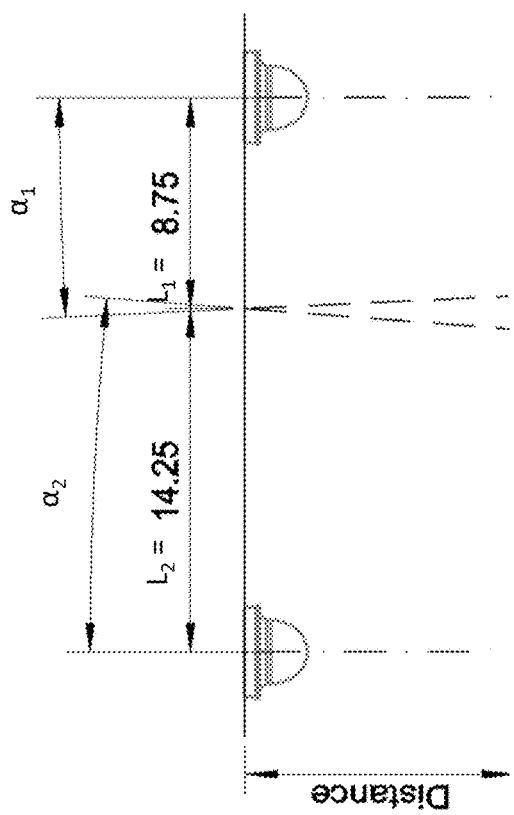
FIG. 17A is a schematic diagram illustrating observation angles of an embodiment of camera modules or detectors of a motion tracking and/or correction system.

FIG. 17A is a schematic diagram illustrating observation angles of an embodiment of camera modules or detectors of a motion tracking and/or correction system. FIG. 17B is a schematic diagram illustrating entrance angles of an embodiment of camera modules or detectors of a motion tracking and/or correction system. As illustrated, D refers to a distance between an LED or other light source, which can be attached to sensor module 1005 or the interior surface of the bore 104 of a scanner or therapeutic device for example, and a marker. In some embodiments, a distance between an LED or other light source and a marker can be about 100 mm, about 110 mm, about 120 mm, about 130 mm, about 140 mm, about 150 mm, about 160 mm, about 170 mm, about 180 mm, about 190 mm, about 200 mm, about 210 mm, about 220 mm, about 230 mm, about 240 mm, about 250 mm, about 260 mm, about 270 mm, about 280 mm, about 290 mm, about 300 mm, about 310 mm, about 320 mm, about 330 mm, about 340 mm, about 350 mm, about 360 mm, about 370 mm, about 380 mm, about 390 mm, about 400 mm, and/or within a range defined by two of the aforementioned values.

L can refer to a length between the center of an optics opening or opening of the camera or detector module and the LED or other light source. In some embodiments, the length between the center of an optics opening or opening of the camera or detector module and the LED or other light source can be about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, about 20 mm, and/or within a range defined by two of the aforementioned values.

An observation angle of the camera or detector module, denoted α, can be calculated according to the following formula:

$$a = \tan^{-1}\left(\frac{L}{D}\right)$$

In some embodiments, the observation angle of the camera or detector module can be about 1.0°, about 1.2°, about 1.4°, about 1.6°, about 1.8°, about 2.0°, about 2.2°, about 2.4°, about 2.6°, about 2.8°, about 3.0°, about 3.2°, about 3.4°, about 3.6°, about 3.8°, about 4.0°, about 4.2°, about 4.4°, about 4.6°, about 4.8°, about 5.0°, and/or within a range defined by two of the aforementioned values.

The observation angle can be different with respect to a particular LED or other light source for a particular camera or detector module. For example, the observation angle with respect to a first LED or light source on the right side of FIG. 17A can be denoted $\alpha_1$, wherein a distance between the first LED or light source and the optics opening or opening of the detector module is denoted $L_1$. Similarly, the observation angle with respect to a second LED or light source on the left side of FIG. 17A can be denoted $\alpha_2$, wherein a distance between the second LED or light source and the optics opening or opening of the detector module is denoted $L_2$. For additional LEDs or light sources, additional distances $L_n$ and angles $\alpha_n$, where n is number of LEDs or light sources (n=3, 4, 5, 6, 7, 8, 9, 10, etc.), can be determined. Further, the observation angle can be different for an integrated motion tracking and/or correction system and a retrofit motion tracking and/or correction system.

Some example values of the above-identified parameters are included below. The following example values are for embodiments in which $L_1$ is about 8.75 mm and $L_2$ is about 14.25 mm. However, other values are also possible for each of the parameters depending on the particular positioning and/or distance of the LED or other light source relative to the detector module and/or specifics of the medical imaging scanner and/or therapeutic device.

TABLE 15

Observation Angles of Detector Modules of an Integrated Motion Tracking and/or Correction System

| | Distance LED to Marker | Observation Angle, $\alpha_1$ | Observation Angle, $\alpha_2$ |
| --- | --- | --- | --- |
| Medical Imaging Scanner with Diameter of About 694.5 mm | 290 mm | 1.7° | 2.8° |
| Medical Imaging Scanner with Diameter of About 684.52 mm | 290 mm | 1.7° | 2.8° |

TABLE 16

Observation Angles of Detector Modules of a Retrofit Motion Tracking and/or Correction System

| | Distance LED to Marker | Observation Angle, $\alpha_1$ | Observation Angle, $\alpha_2$ |
| --- | --- | --- | --- |
| Medical Imaging Scanner with Diameter of About 685.5 mm | 250 mm | 2.0° | 3.3° |
| Medical Imaging Scanner with Diameter of About 597 mm | 230 mm | 3.3° | 4.9° |

FIG. 17B is a schematic diagram illustrating entrance angles of an embodiment of camera modules or detectors of a motion tracking and/or correction system. As illustrated, the entrance angle of a marker for a particular detector module 108C, 108D can depend on the rotational position of the marker 110. At a default position when the head of the subject is vertically aligned with the center of the bore of a scanner when viewed from a front view, the marker 110 can be naturally positioned at about 17° with reference to a vertical plane, for example if the marker is attached to the side of the nose of the subject. Similarly, if the marker is attached to a nose mount over the nose of the subject, the marker 110 can be naturally positioned at about 45° with reference to a vertical plane at a default position when the head of the subject is vertically aligned with the center of the bore of a scanner when viewed from a front view.

The entrance angle can also depend on the rotational configuration of the head of the subject. When the head of the subject is tiled, for example by 10°, the entrance angle can be varied. Further, the entrance angle can be different for an integrated motion tracking and/or correction system and a retrofit motion tracking and/or correction system. The entrance angle can also depend on the particular size of a medical imaging scanner or therapeutic device. Further, the entrance angle can be different for different head coils being used, for example a head coil with a 64 head-neck configuration or a 20 head-neck configuration. This can be because the entrance angle of the marker may be blocked by the particular shape or configuration of the head coil.

In some embodiments, the entrance angle can be about −90°, about −85°, about −80°, about −75°, about −70°, about −65°, about −60°, about −55°, about −50°, about −45°, about −40°, about −35°, about −30°, about −25°, about −20°, about −15°, about −10°, about −5°, about 0°, about 5°, about 10°, about 15°, about 20°, about 25°, about 30°, about 35°, about 40°, about 45°, about 50°, about 55°, about 60°, about 65°, about 70°, about 75°, about 80°, about 85°, about 90°, and/or within a range defined by two of the aforementioned values.

Some example values of the entrance angle are included below. However, other values are also possible for the entrance angle depending on the detector and/or specifics of the medical imaging scanner and/or therapeutic device.

TABLE 17

Entrance Angles of a Marker for Detector Modules of an Integrated Motion Tracking and/or Correction System for a Medical Imaging Scanner with a Diameter of About 694.5 mm

| Head Position | Entrance Angle (HN64) | | Entrance Angle (HN 20) | |
| --- | --- | --- | --- | --- |
| | Detector 108C | Detector 108D | Detector 108C | Detector 108D |
| Marker at 17° | Range: +7 to +54° | | | |
| Default | 54° (1902) | 26° (1908) | 54° (1902) | 27° (1908) |
| Head Rotated 10° | 38° (1904) | 12° (1906) | 31° (1904) | 7° (1906) |
| Marker at 45° | Range: −21° to +26° | | | |
| Default | 26° (1902) | −2° (1908) | 26° (1902) | −1° (1908) |
| Head Rotated 10° | 10° (1904) | −16° (1906) | 3° (1904) | −21° (1906) |

TABLE 18

Entrance Angles of a Marker for Detector Modules of an Integrated Motion Tracking and/or Correction System for a Medical Imaging Scanner with a Diameter of About 684.52 mm

| Head Position | Entrance Angle (HN64) | | Entrance Angle (HN 20) | |
| --- | --- | --- | --- | --- |
| | Detector 108C | Detector 108D | Detector 108C | Detector 108D |
| Marker at 17° | Range: +3 to +50° | | | |
| Default | 49° (1902) | 22° (1908) | 50° (1902) | 27° (1908) |
| Head Rotated 10° | 33° (1904) | 8° (1906) | 23° (1904) | 3° (1906) |
| Marker at 45° | Range: −25° to +21° | | | |
| Default | 21° (1902) | −6° (1908) | 22° (1902) | −1° (1908) |
| Head Rotated 10° | 5° (1904) | −20° (1906) | −5° (1904) | −25° (1906) |

TABLE 19

Entrance Angles of a Marker for Detector Modules of a Retrofit Motion Tracking and/or Correction System for a Medical Imaging Scanner with a Diameter of About 685.5 mm

| Head Position | Entrance Angle (HN64) | | Entrance Angle (HN 20) | |
| --- | --- | --- | --- | --- |
| | Detector 108C | Detector 108D | Detector 108C | Detector 108D |
| Marker at 17° | Range: +6 to +54° | | | |
| Default | 54° (1902) | 26° (1908) | 54° (1902) | 27° (1908) |
| Head Rotated 10° | 37° (1904) | 12° (1906) | 30° (1904) | 6° (1906) |
| Marker at 45° | Range: −22° to +26° | | | |
| Default | 26° (1902) | −2° (1908) | 26° (1902) | −1° (1908) |
| Head Rotated 10° | 9° (1904) | −16° (1906) | 2° (1904) | −22° (1906) |

TABLE 20

Entrance Angles of a Marker for Detector Modules of a Retrofit Motion Tracking and/or Correction System for a Medical Imaging Scanner with a Diameter of About 597 mm

| Head Position | Entrance Angle (HN64) | | Entrance Angle (HN 20) | |
| --- | --- | --- | --- | --- |
| | Detector 108C | Detector 108D | Detector 108C | Detector 108D |
| Marker at 17° | Range: +4 to +59° | | | |
| Default | 55° (1902) | 27° (1908) | 56° (1902) | 28° (1908) |
| Head Rotated 10° | 36° (1904) | 12° (1906) | 28° (1904) | 6° (1906) |
| Marker at 45° | Range: −22° to +28° | | | |
| Default | 27° (1902) | −1° (1908) | 28° (1902) | 0° (1908) |
| Head Rotated 10° | 8° (1904) | −16° (1906) | 0° (1904) | −22° (1906) |

Figure 18B:
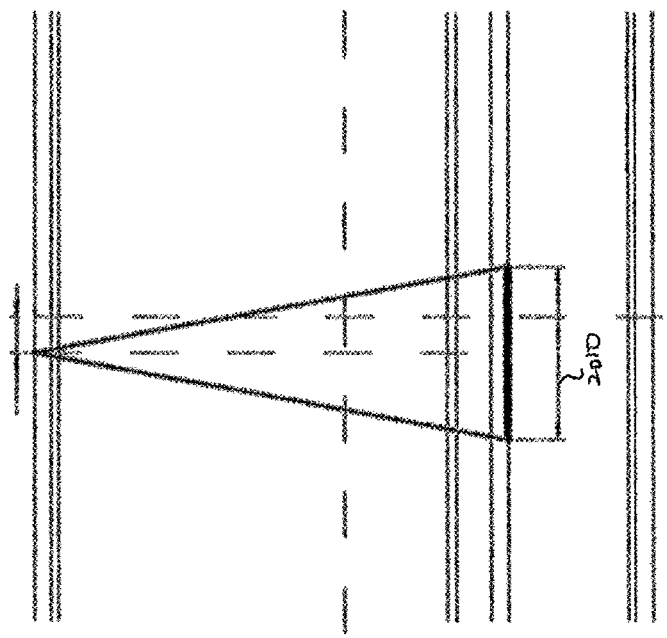
FIG. 18B is a schematic diagram illustrating a side view of camera or detector overlap of an embodiment of camera modules or detectors of a motion tracking and/or correction system.
Figure 18A:
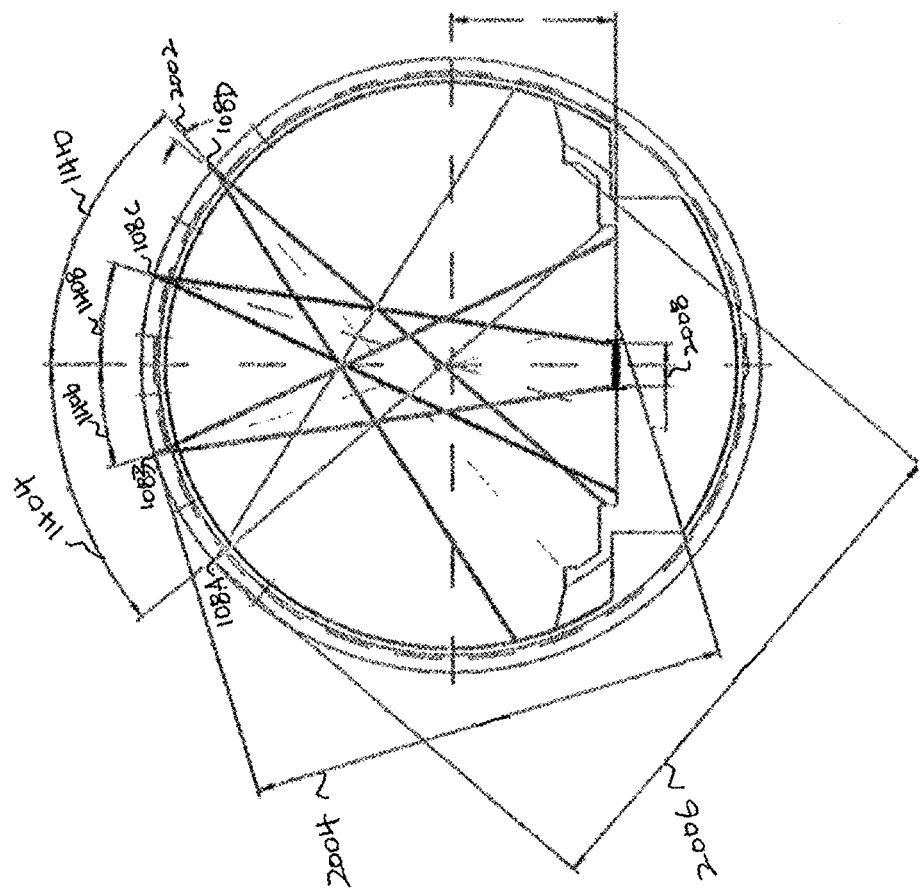
FIG. 18A is a schematic diagram illustrating a front view of camera or detector overlap of an embodiment of camera modules or detectors of a motion tracking and/or correction system.

FIG. 18A is a schematic diagram illustrating a front view of camera or detector overlap of an embodiment of camera modules or detectors of a motion tracking and/or correction system. FIG. 18B is a schematic diagram illustrating a side view of camera module or detector overlap of an embodiment of camera module or detector of a motion tracking and/or correction system.

As illustrated, in embodiments comprising one or more detector modules, the line of sight or visual field of the detector modules may overlap. For example, the visual field of one or more detectors 108A, 108B, 108C, 108D may overlap with the visual field of one or more other detectors 108A, 108B, 108C, 108D. The visual field of two top-positioned detectors 108B, 108C may overlap. A horizontal distance of overlap 2008 between the two top detectors 108B, 108C, when viewed from a front view into the bore of the medical imaging scanner or therapeutic device, can be formed on the bottom or bed of the scanner or device. Similarly, a horizontal distance of overlap 2010 between the two top detectors 108B, 108C, when viewed from a side view into the bore of the medical imaging scanner or therapeutic device, can be formed on the bottom or bed of the scanner or device. These two distances 2008, 2010 can form the dimensions of the overlap in visual field between two top detectors 108B, 108C.

The motion tracking and/or correction system may have a tracking working distance, which can be defined as a range of distances in which the motion tracking is functional or operative. In some embodiments, the tracking working distance can be about 100 mm, about 110 mm, about 120 mm, about 130 mm, about 140 mm, about 150 mm, about 160 mm, about 170 mm, about 180 mm, about 190 mm, about 200 mm, about 210 mm, about 220 mm, about 230 mm, about 240 mm, about 250 mm, about 260 mm, about 270 mm, about 280 mm, about 290 mm, about 300 mm, about 310 mm, about 320 mm, about 330 mm, about 340 mm, about 350 mm, and/or within a range defined by two of the aforementioned values.

The motion tracking and/or correction system may also have a calibration target distance. The calibration target distance may be defined as a range of distance between a visual length 2004 of a top detector 108B, as limited by the particulars of the medical imaging scanner or therapeutic device, and a visual length 2006 of a side detector 108A, about 300 mm, and/or within a range defined by two of the aforementioned values.

Some values of the tracking working distance, calibration target distance, and detector overlap of the top detectors and/or side detectors are provided below. Each of the above-identified parameters can be different from an integrated motion tracking and/or correction system, a retrofit motion tracking and/or correction system, and/or size or particulars of the medical imaging scanner or therapeutic device. Other values are also possible for each of the parameters depending on the detector and/or specifics of the medical imaging scanner and/or therapeutic device.

TABLE 21

Calibration and Camera Overlap Values of Motion Tracking and/or Correction Systems

| Motion Tracking and/or Correction System | Detector Optics (mm) | Tracking Working Distance (mm) | Calibration Target Distance (mm) | Top Detector Overlap (108B, 108C) (mm × mm) | Side Detector Overlap (108A, 108D) (mm × mm) |
|---|---|---|---|---|---|
| Integrated System with 70 cm Bore Diameter | 16 | 285 +/− 45 | 580~650 | 50 × 210 | None |
| Integrated System with 70 cm Bore Diameter | 16 | 280 +/− 45 | 600~900 | 30 × 210 | None |
| Retrofit System with 70 cm Bore Diameter | 16 | 250 +/− 45 | 550~620 | 40 × 200 | None |
| Retrofit System with 60 cm Bore Diameter | 12 | 175 +/− 45 | 480~560 | 60 × 260 | None | similarly limited by the particulars of the medical imaging scanner or therapeutic device.

In certain embodiments, the calibration target distance can be about 100 mm, about 110 mm, about 120 mm, about 130 mm, about 140 mm, about 150 mm, about 160 mm, about 170 mm, about 180 mm, about 190 mm, about 200 mm, about 210 mm, about 220 mm, about 230 mm, about 240 mm, about 250 mm, about 260 mm, about 270 mm, about 280 mm, about 290 mm, about 300 mm, about 310 mm, about 320 mm, about 330 mm, about 340 mm, about 350 mm, about 360 mm, about 370 mm, about 380 mm, about 390 mm, about 400 mm, about 410 mm, about 420 mm, about 430 mm, about 440 mm, about 450 mm, about 460 mm, about 470 mm, about 480 mm, about 490 mm, about 500 mm, about 510 mm, about 520 mm, about 530 mm, about 540 mm, about 550 mm, about 560 mm, about 570 mm, about 580 mm, about 590 mm, about 600 mm, about 610 mm, about 620 mm, about 630 mm, about 640 mm, about 650 mm, about 660 mm, about 670 mm, about 680 mm, about 680 mm, about 700 mm, and/or within a range defined by two of the aforementioned values.

In certain embodiments, an area of overlap between two detectors, for example two top detectors or two side detectors, can be a rectangle. Each of the length and width of the area of overlap can be about 10 mm, about 20 mm, about 30 mm, about 40 mm, about 50 mm, about 60 mm, about 70 mm, about 80 mm, about 90 mm, about 100 mm, about 110 mm, about 120 mm, about 130 mm, about 140 mm, about 150 mm, about 160 mm, about 170 mm, about 180 mm, about 190 mm, about 200 mm, about 210 mm, about 220 mm, about 230 mm, about 240 mm, about 250 mm, about 260 mm, about 270 mm, about 280 mm, about 290 mm, Marker Position with Respect to Subject In some embodiments, one or more markers are configured to be used in conjunction with a motion tracking and/or correction system and/or device. The operation of a motion tracking and/or correction system can vary depending on the positioning of one or more markers, for example with respect to the subject.

Figures 19A, 19B, 19C:
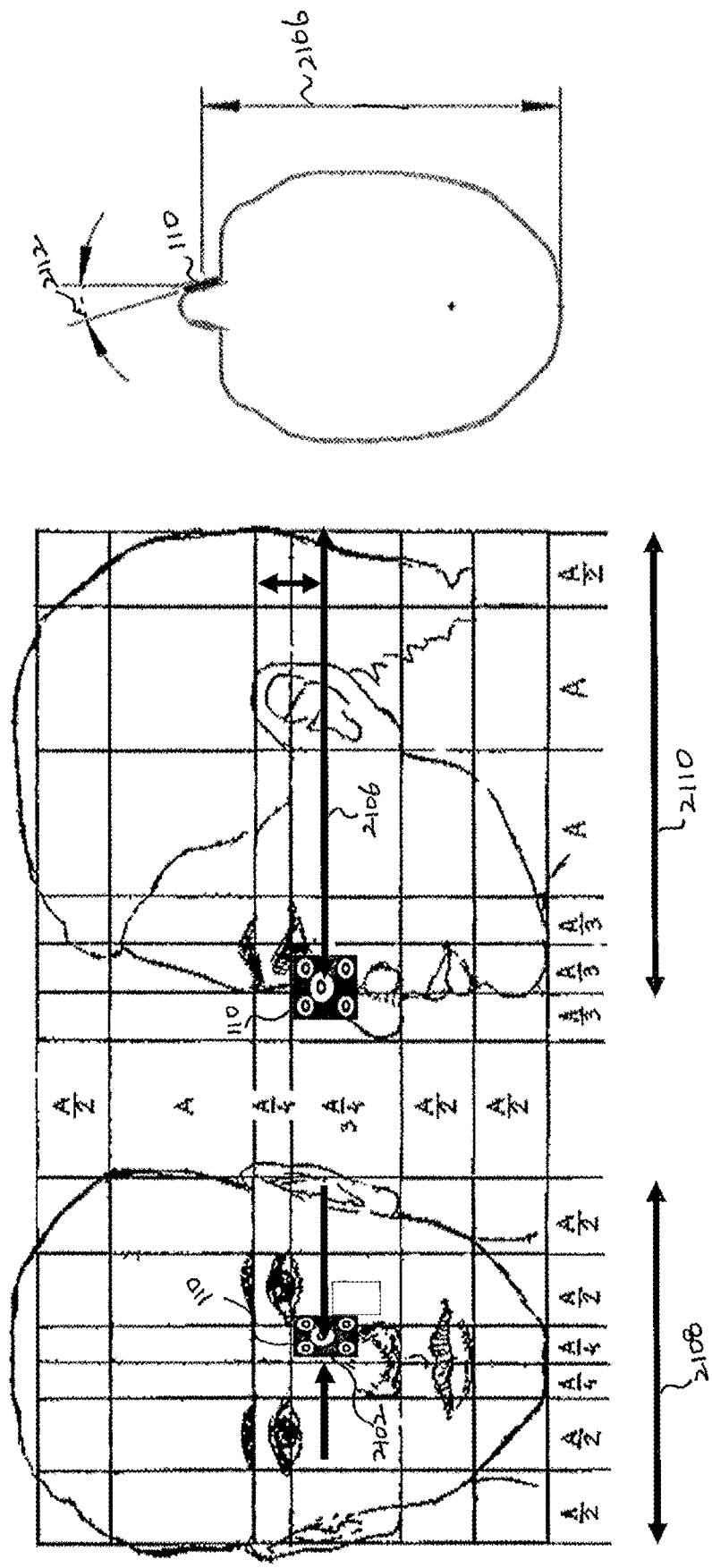
FIG. 19A is a schematic diagram illustrating a front view of an embodiment of a position of a marker of a motion tracking and/or correction system with respect to the subject.
FIG. 19B is a schematic diagram illustrating a side view of an embodiment of a position of a marker of a motion tracking and/or correction system with respect to the subject.
FIG. 19C is a schematic diagram illustrating a top view of an embodiment of a position of a marker of a motion tracking and/or correction system with respect to the subject.

FIG. 19A is a schematic diagram illustrating a front view of an embodiment of a position of a marker of a motion tracking and/or correction system with respect to the subject. FIG. 19B is a schematic diagram illustrating a side view of an embodiment of a position of a marker of a motion tracking and/or correction system with respect to the subject. FIG. 19C is a schematic diagram illustrating a top view of an embodiment of a position of a marker of a motion tracking and/or correction system with respect to the subject.

As illustrated in FIG. 19A, a cranial base width 2108 of a subject can be generally about 142 mm. For some subjects, the cranial base width 2108 can be as wide as about 150 mm and can be as narrow as about 136 mm. Further, as illustrated, in some embodiments, one or more markers 110 can be configured to be placed on the side of the subject's nose. More specifically, by placing a marker 110 on the side of a subject's nose, a horizontal distance 2102 along the cranial width between the center of the subject's nose and the center of the marker 110 can be specified to pinpoint the position of the marker 110. This horizontal distance 2102 along the cranial width can be about 11 mm in some embodiments. In certain embodiments, this horizontal distance 2102 along the cranial width can be about 5 mm, about 6 mm, about 7 mm, about 8 mm, about 9 mm, about 10 mm, about 11 mm, about 12 mm, about 13 mm, about 14 mm, about 15 mm, and/or within a range defined by two of the aforementioned values.

As illustrated in FIG. 19B, a cranial length 2110 of a subject can be generally about 191 mm. For some subjects, the cranial length 2110 can be as wide as about 200 mm and can be as narrow as about 184 mm. In some embodiments, by placing a marker 110 on the side of a subject's nose, a horizontal distance 2106 along the cranial length between the back of the head or back end of the cranial length and the center of the marker 110 can be specified to pinpoint the position of the marker 110. This horizontal distance 2106 along the cranial length can be about 188 mm in some embodiments. In certain embodiments, this horizontal distance 2106 along the cranial length can be about 170 mm, about 175 mm, about 180 mm, about 185 mm, about 190 mm, about 195 mm, about 200 mm, and/or within a range defined by two of the aforementioned values.

As illustrated in FIG. 19C, placement of a marker 110 on the side of a subject's nose can result in an angle 2112 between the surface of the marker 110 and a vertical line when viewed from the top of the subject's head. This angle 2112 can be further used to pinpoint the configuration or position of a marker 110. The angle 2112 between a line extended along the surface of the marker 110 and a vertical line when viewed from the top of the subject's head as illustrated in FIG. 19C can be about 17°. In certain embodiments, this angle 2112 can be about 10°, about 11°, about 12°, about 13°, about 14°, about 15°, about 16°, about 17°, about 18°, about 19°, about 20°, about 21°, about 22°, about 23°, about 24°, about 25°, about 26°, about 27°, about 28°, about 29°, about 30°, and/or within a range defined by two of the aforementioned values. This angle 2112 can depend on the shape or configuration of a subject's nose.

In addition or as an alternative to positioning one or more markers 110 on the side of the nose for motion compensation of head movement, one or more markers 110 can be also positioned anywhere on the subject's head and within the field of view of the detector or camera systems. Such positions include but are not limited to the forehead, the cheeks, the chin, the upper lip, and the mouth, for example using a mouth guard or holder.

One or more markers 110 can also be positioned on other body portions for motion compensation of movements of the other body portions. As for head movements, one or more markers 110 can be positioned on the body portion and within the field of view of the detector or camera systems.

Figure 20B:
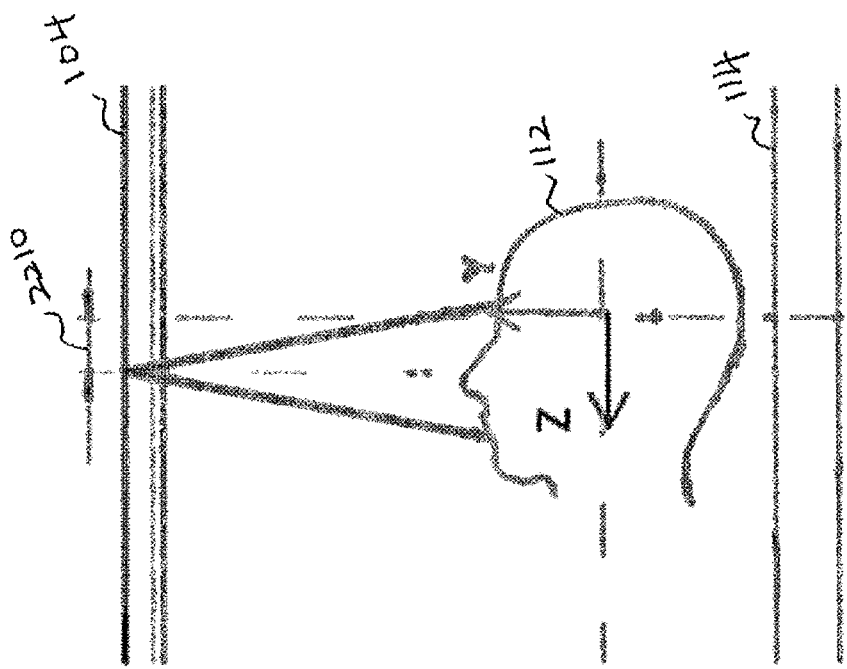
FIG. 20B is a schematic diagram illustrating a side view of an embodiment of rotation of a marker of a motion tracking and/or correction system with respect to a medical imaging scanner or therapeutic device.
Figure 20A:
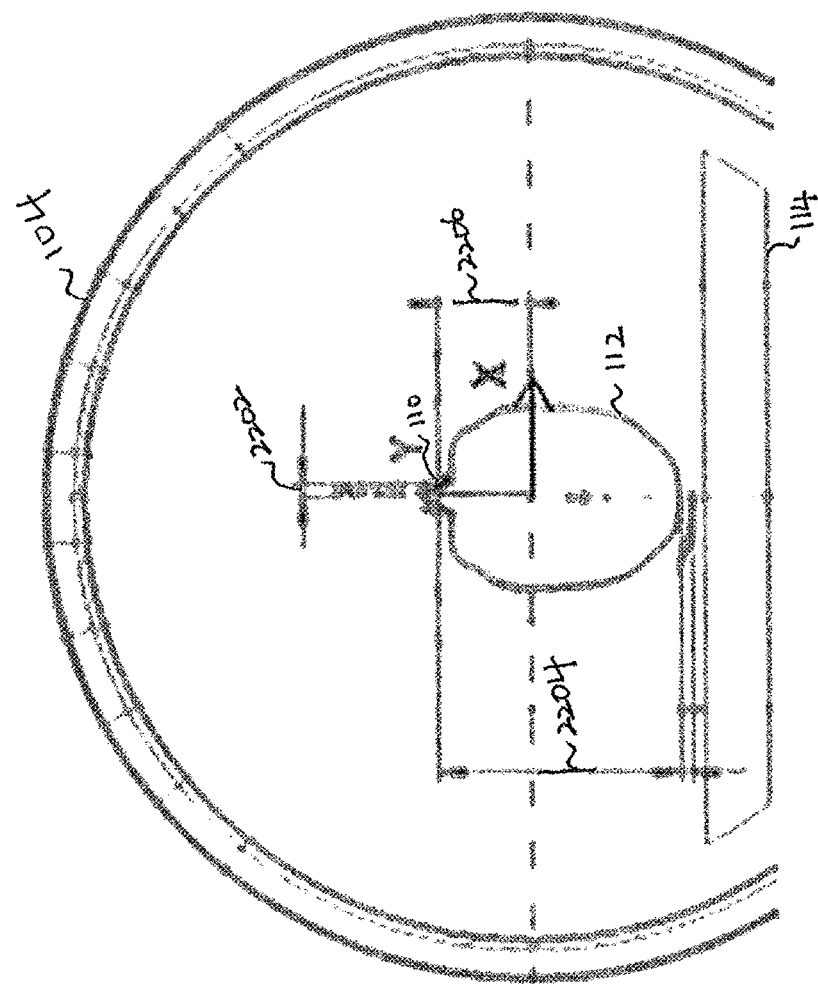
FIG. 20A is a schematic diagram illustrating a front view of an embodiment of rotation of a marker of a motion tracking and/or correction system with respect to a medical imaging scanner or therapeutic device.

Marker Position with Respect to Medical Imaging Scanner and/or Therapeutic Device The operation of a motion tracking and/or correction system can also or alternatively vary depending on the positioning of one or more markers, for example with respect to the medical imaging scanner and/or therapeutic device. FIG. 20A is a schematic diagram illustrating a front view of an embodiment of the position of a marker of a motion tracking and/or correction system with respect to a medical imaging scanner or therapeutic device. FIG. 20B is a schematic diagram illustrating a side view of an embodiment of the position of a marker of a motion tracking and/or correction system with respect to a medical imaging scanner or therapeutic device.

The particular position of a marker with respect to a medical imaging scanner and/or therapeutic device can be ascertained. For example, when viewed in a front view as illustrated in FIG. 20A, a first horizontal distance 2202 along the x axis between the center of a marker 110 and a vertical line along the center of the subject and/or bore 104 can be determined. In some embodiments, the first horizontal distance 2202 can be about 5 mm, about 6 mm, about 7 mm, about 8 mm, about 9 mm, about 10 mm, about 11 mm, about 12 mm, about 13 mm, about 14 mm, about 15 mm, and/or within a range defined by two of the aforementioned values.

Further, a first vertical distance 2204 along the y axis between the back or bottom of the subject's head and the center of the marker can be determined. In certain embodiments, the first vertical distance 2204 can be about 150 mm, about 160 mm, about 170 mm, about 180 mm, about 190 mm, about 200 mm, about 210 mm, about 220 mm, about 230 mm, about 240 mm, about 250 mm, and/or within a range defined by two of the aforementioned values.

Similarly, a second vertical distance 2206 along the y axis between the center of the subject's head and the center of a marker 110 can be determined. In some embodiments, the second vertical distance 2206 can be about 50 mm, about 60 mm, about 70 mm, about 80 mm, about 90 mm, about 100 mm, about 110 mm, about 120 mm, about 130 mm, about 140 mm, about 150 mm, and/or within a range defined by two of the aforementioned values.

Further, when viewed in a side view as illustrated in FIG. 20B, a second horizontal distance 2210 along the z axis between the center of a marker 110 and center of the medical imaging scanner or therapeutic device can be determined. The horizontal distance 2210 and the distance 1402 can be substantially the same in some embodiments. In certain embodiments, the second horizontal distance 2210 can be about 30 mm, about 31 mm, about 32 mm, about 33 mm, about 34 mm, about 35 mm, about 36 mm, about 37 mm, about 38 mm, about 39 mm, about 40 mm, about 41 mm, about 42 mm, about 43 mm, about 44 mm, about 45 mm, about 46 mm, about 47 mm, about 48 mm, about 49 mm, about 50 mm, and/or within a range defined by two of the aforementioned values.

Some values of the first horizontal distance 2202, first vertical distance 2204, and second vertical distance 2206, and second horizontal distance 2210 are provided below. Each of the above-identified parameters can be different for an integrated motion tracking and/or correction system, a retrofit motion tracking and/or correction system, particulars of the head coil, and/or size or particulars of the medical imaging scanner or therapeutic device. Other values are also possible for each of the parameters depending on the detector and/or specifics of the medical imaging scanner and/or therapeutic device.

TABLE 22

Marker Position with respect to Scanner or Therapeutic Device

| Bore Diameter and Integrated/Retrofit System | Location and Angle of Marker on Subject | First Horizontal Distance 2202 for HN 64/HN 20 Head Coil | Second Vertical Distance 2206 for HN 64/HN 20 Head Coil | Second Horizontal Distance 2210 for HN 64/HN 20 Head Coil |
|---|---|---|---|---|
| 694.5 mm/ Integrated | Side of nose/17° | 11 mm/11 mm | 71.5 mm/66.5 mm | 44 mm/44 mm |

TABLE 22-continued

Marker Position with respect to Scanner or Therapeutic Device

| Bore Diameter and Integrated/Retrofit System | Location and Angle of Marker on Subject | First Horizontal Distance 2202 for HN 64/HN 20 Head Coil | Second Vertical Distance 2206 for HN 64/HN 20 Head Coil | Second Horizontal Distance 2210 for HN 64/HN 20 Head Coil |
|---|---|---|---|---|
| 684.52 mm/ Integrated | Side of nose/17° | 11 mm/11 mm | 71.5 mm/66.5 mm | 44 mm/44 mm |
| 685.5 mm/ Retrofit | Side of nose/17° | 11 mm/11 mm | 71.5 mm/66.5 mm | 38 mm/38 mm |
| 597 mm/ Retrofit | Side of nose/17° | 11 mm/11 mm | 101.5 mm/96.5 mm | 38 mm/38 mm |

As discussed herein, in certain embodiments, one or more markers 110 can also be positioned on other body portions for motion compensation of movements of the other body portions. One or more of the above-identified distances may be different in embodiments for one or other body portions.

Marker Rotation

Figure 21B:
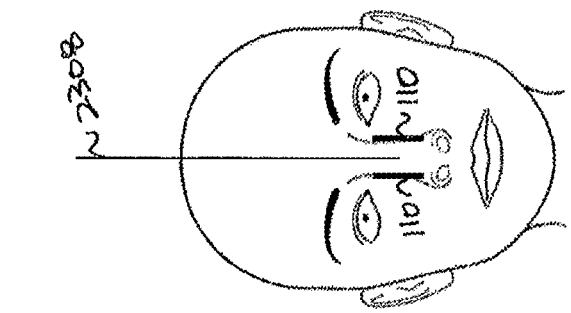
FIG. 21B is a schematic diagram illustrating a front view of an embodiment of rotation of a marker of a motion tracking and/or correction system with respect to the subject.
Figure 21B:
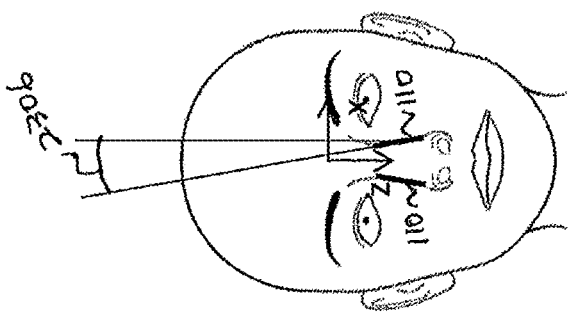
Figure 21A:
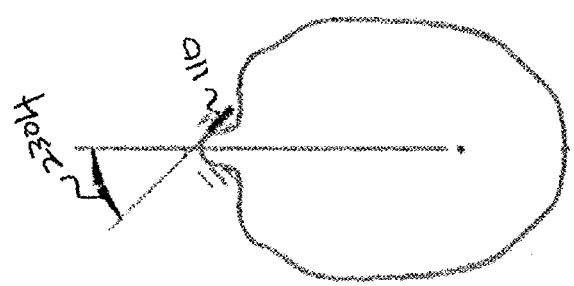
FIG. 21A is a schematic diagram illustrating a top view of an embodiment of rotation of a marker of a motion tracking and/or correction system with respect to the subject.
Figure 21A:
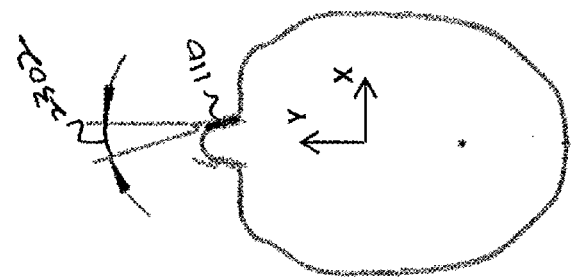

In some embodiments, an optimal rotation of one or more markers and/or a range thereof can exist for optimal motion detection and correction by a motion tracking and/or correction system. FIG. 21A is a schematic diagram illustrating a top view of an embodiment of rotation of a marker of a motion tracking and/or correction system with respect to the subject. FIG. 21B is a schematic diagram illustrating a front view of an embodiment of rotation of a marker of a motion tracking and/or correction system with respect to the subject.

As illustrated in FIG. 21A, in some embodiments, a marker 110 can be attached directly or indirectly to the side of a subject's nose. In such embodiments, when viewed from the top of the subject's head, the marker 110 can be angled in line with the physiological angle of the subject's nose. More specifically, an angle 2302 can exist between a vertical line drawn along the y axis, as illustrated in FIG. 21A, and a line extending along the marker 110. This angle 2302 can be about 17° for example. In such embodiments, a camera or detector entrance angle viewing the subject from the top of the subject's head as illustrated in FIG. 23A may range between about +3° to about +59°.

In certain embodiments, each of the angle 2302 and a camera or detector entrance angle viewing the subject from the top of the subject's head as illustrated in FIG. 23A can be about 0°, about 5°, about 10°, about 15°, about 20°, about 25°, about 30°, about 35°, about 40°, about 45°, about 50°, about 55°, about 60°, about 65°, about 70°, about 75°, about 80°, about 85°, about 90°, and/or within a range defined by two of the aforementioned values. Further, in such embodiments, retroreflection may be poor and/or asymmetric across one or more camera or detectors for viewing the subject in the illustrated direction of FIG. 23A. Accordingly, the quality of motion tracking may be relatively poor.

In other embodiments, a marker 110 can be attached to a nose mount instead of being attached to the side of a subject's nose. By attaching a marker 110 to a nose mount, the angle 2304 between the vertical line along the y axis, as illustrated in FIG. 23A, and a line extending from the surface of the marker 110 can be manipulated. For example, the angle 2304 may be about 45° in some embodiments. Due to such configuration, the camera or detector entrance angle viewing the subject from the top of the subject's head as illustrated in FIG. 23A may range between −25° to +31° in some embodiments.

In certain embodiments, each of the angle 2304 and the camera or detector entrance angle viewing the subject from the top of the subject's head as illustrated in FIG. 23A can be about −90°, about −85°, about −80°, about −75°, about −70°, about −65°, about −60°, about −55°, about −50°, about −45°, about −40°, about −35°, about −30°, about −25°, about −20°, about −15°, about −10°, about −5°, about 0°, about 5°, about 10°, about 15°, about 20°, about 25°, about 30°, about 35°, about 40°, about 45°, about 50°, about 55°, about 60°, about 65°, about 70°, about 75°, about 80°, about 85°, about 90° and/or within a range defined by two of the aforementioned values.

Further, due to such configuration, retroreflection on one or more cameras or detectors may be improved and/or be symmetric or more symmetric compared to an embodiment in which a marker 110 is attached to the side of the nose for viewing the subject in the illustrated direction of FIG. 23A. As such, tracking quality may also be improved compared to an embodiment in which a marker 110 is attached to the side of the nose.

Similarly, in embodiments in which a marker 110 is attached to the side of a nose, an angle 2306 may be exist between an extended line along the marker 110 and a vertical line along the z axis when viewed from a front view as illustrated in FIG. 23B. For example, the angle 2306 may be about 10°. In such embodiments, a camera or detector entrance angle viewing the subject from above the subject's face as illustrated in FIG. 23B may be about 10°.

In certain embodiments, each of the angle 2306 and camera or detector entrance angle viewing the subject from above the subject's face as illustrated in FIG. 23B can be about 0°, about 5°, about 10°, about 15°, about 20°, about 25°, about 30°, about 35°, about 40°, about 45°, about 50°, about 55°, about 60°, about 65°, about 70°, about 75°, about 80°, about 85°, about 90°, and/or within a range defined by two of the aforementioned values. Further, in such embodiments, retroreflection may be at acceptable levels and may be generally symmetric for viewing the subject in the illustrated direction of FIG. 23B. Tracking quality may also be at acceptable levels.

In other embodiments, by attaching a marker 110 to a nose mount, the angle 2308 between an extended line along the marker 110 and a vertical line along the z axis when viewed from a front view as illustrated in FIG. 23B can be manipulated. For example, the angle 2308 may be about 0° in some embodiments. Due to such configuration, the camera or detector entrance angle viewing the subject from above the subject's face as illustrated in FIG. 23B may be about 0° in some embodiments.

In certain embodiments, each of the angle 2308 and the camera or detector entrance angle viewing the subject from the top of the subject's head as illustrated in FIG. 23B can be about −90°, about −85°, about −80°, about −75°, about −70°, about −65°, about −60°, about −55°, about −50°, about −45°, about −40°, about −35°, about −30°, about −25°, about −20°, about −15°, about −10°, about −5°, about 0°, about 5°, about 10°, about 15°, about 20°, about 25°, about 30°, about 35°, about 40°, about 45°, about 50°, about 55°, about 60°, about 65°, about 70°, about 75°, about 80°, about 85°, about 90° and/or within a range defined by two of the aforementioned values.

Further, due to such configuration, retroreflection on one or more cameras or detectors may be improved and/or be symmetric or more symmetric compared to an embodiment in which a marker 110 is attached to the side of the nose for viewing the subject in the illustrated direction of FIG. 23B. As such, tracking quality may also be improved compared to an embodiment in which a marker 110 is attached to the side of the nose.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus 100. Further, the disclosure herein of any particular feature, aspect, method, property, characteristic, quality, attribute, element, or the like in connection with an embodiment can be used in all other embodiments set forth herein. For all of the embodiments described herein the steps of the methods need not be performed sequentially. Thus, it is intended that the scope of the present invention herein disclosed should not be limited by the particular disclosed embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 3 mm" includes "3 mm."

The headings provided herein, if any, are for convenience only and do not necessarily affect the scope or meaning of the devices and methods disclosed herein.

What is claimed is:

1. A motion correction device for a medical imaging scanner, the device comprising:
    a device housing, wherein the device housing comprises an arcuate surface, and wherein the device housing comprises:
        one or more optics openings on the arcuate surface;
        one or more detectors configured to detect motion of a subject of the medical imaging scanner through the one or more optics openings, wherein each of the one or more detectors further comprises:
            a detector housing; and
            a sensor module placed within the detector housing, wherein the sensor module is configured to be removably coupled to the detector module housing;
        a power unit configured to regulate power to the one or more detectors; and
        one or more wires configured to connect the one or more detectors to the power unit,
    wherein the device housing is configured to be removably coupled to a top inner surface of a bore of the medical imaging scanner.

2. The motion correction device of claim 1, wherein the device is configured to be removably coupled to a plurality of medical imaging scanners, wherein each of the plurality of medical imaging scanners comprises a bore of a different size.

3. The motion correction device of claim 1, wherein the device is configured to detect motion of the subject of the medical imaging scanner and transmit the detected motion to a motion tracking system for processing the detected motion.

4. The motion correction device of claim 1, wherein the device is configured to be removed and reattached to the medical imaging scanner without losing alignment of the one or more detectors.

5. The motion correction device of claim 1, wherein the one or more optics openings comprises indium tin oxide coated glass.

6. The motion correction device of claim 1, wherein the one or more optics openings protrude from the arcuate surface at an angle.

7. The motion correction device of claim 1, wherein the device housing further comprises one or more radiofrequency chokes.

8. The motion correction device of claim 1, wherein the device housing further comprises one or more mounting clips, wherein the one or more mounting clips are configured to be removably attached to a mounting bracket, wherein the mounting bracket is attached to the top inner surface of the bore.

9. The motion correction device of claim 1, wherein the detector housing is flash plated with a material configured to delay oxidation.

10. The motion correction device of claim 1, wherein the detector housing comprises a top cover and a bottom cover, wherein the top cover comprises one or more non-parallel walls to eliminate standing waves.

11. The motion correction device of claim 10, wherein the top cover comprises nickel.

12. The motion correction device of claim 1, wherein the sensor module comprises an imaging sensor, an optics module, and a light source.

13. The motion correction device of claim 12, wherein the optics module comprises a sensor and an optics.

14. The motion correction device of claim 12, wherein the optics is mechanically fixated within the optics module.

15. The motion correction device of claim 13, wherein the optics is placed within the optics module in a longitudinal direction of the optics module.

* * * * *